United States Patent
Birikh et al.

(10) Patent No.: US 10,246,696 B2
(45) Date of Patent: Apr. 2, 2019

(54) PECTINASES WITH IMPROVED THERMOSTABILITY

(71) Applicant: Metgen OY, Kaarina (FI)

(72) Inventors: Klara Birikh, Kaarina (FI); Anu Minna Maaret Suonpaa, Kaarina (FI)

(73) Assignee: Metgen OY, Kaarina (FI)

( * ) Notice: Subject to any disclaimer, the term of this patent is extended or adjusted under 35 U.S.C. 154(b) by 0 days.

(21) Appl. No.: 16/062,595

(22) PCT Filed: Dec. 8, 2016

(86) PCT No.: PCT/EP2016/080265
§ 371 (c)(1),
(2) Date: Jun. 14, 2018

(87) PCT Pub. No.: WO2017/102544
PCT Pub. Date: Jun. 22, 2017

(65) Prior Publication Data
US 2019/0002864 A1  Jan. 3, 2019

(30) Foreign Application Priority Data

Dec. 15, 2015 (EP) .................................. 15200250

(51) Int. Cl.
*C12N 9/88* (2006.01)
*C11D 3/386* (2006.01)
*C12N 15/70* (2006.01)

(52) U.S. Cl.
CPC .............. *C12N 9/88* (2013.01); *C11D 3/386* (2013.01); *C12N 15/70* (2013.01); *C12Y 402/02002* (2013.01)

(58) Field of Classification Search
None
See application file for complete search history.

(56) References Cited

FOREIGN PATENT DOCUMENTS

WO    2008138109    11/2008

OTHER PUBLICATIONS

Chiliveri et al., A Novel Thermostable, Alkaline Pectate Lyase from Bacillus Tequilensis SV11 with Potential in Textile Industry, Elsevier, Nov. 10, 2013, pp. 264-272.
Database UniProt [Online], "SubName: Full=Ptate lyase {ECO:0000313|EMBL:KIL52125.1}; EC=4.2.2.2 {ECO:0000313|EMBL:KIL52125.1};" retrieved from EBI accession No. UNIPROT:A0A0C2RPE1, Apr. 1, 2015, 2 pgs.
International Search Report and Written Opinion for International Application No. PCT/EP2016/080265, dated Feb. 15, 2017, 12 pgs.
Liang et al., Improving the Thermoactivity and Thermostability of Pectate Lyase from Bacillus Pumilus for Ramie Degumming, Appl Microbiol Biotechnol, Jul. 12, 2014, pp. 2673-2682.
Nakaniwa et al., An in vitro Evaluation of a Thermostable Pectate Lyase by Using Error-Prone PCR, Journal of Molecular Catalysis, Jul. 31, 2003, pp. 127-131.
Xiao et al., Improvement of the Thermostability and Activity of a Pectate Lyase by Single Amino Acid Substitutions, Using a Strategy Based on Melting-Temperature-guided Sequence Alignment, Applied and Environmental Microbiology, Feb. 2008, pp. 1183-1189, vol. 74 No. 4.

*Primary Examiner* — Suzanne M Noakes
(74) *Attorney, Agent, or Firm* — Patent Law Works LLP

(57) ABSTRACT

The invention is in the field of protein chemistry, in particular in the field of enzymology. It provides pectinases, i.e. polypeptides with pectin-degrading properties. In particular the invention provides polypeptides with pectate lyase activity (EC 4.2.2.2). Enzymes according to the invention have improved properties, such as improved thermostability and decreased calcium dependence.

Figure 1:
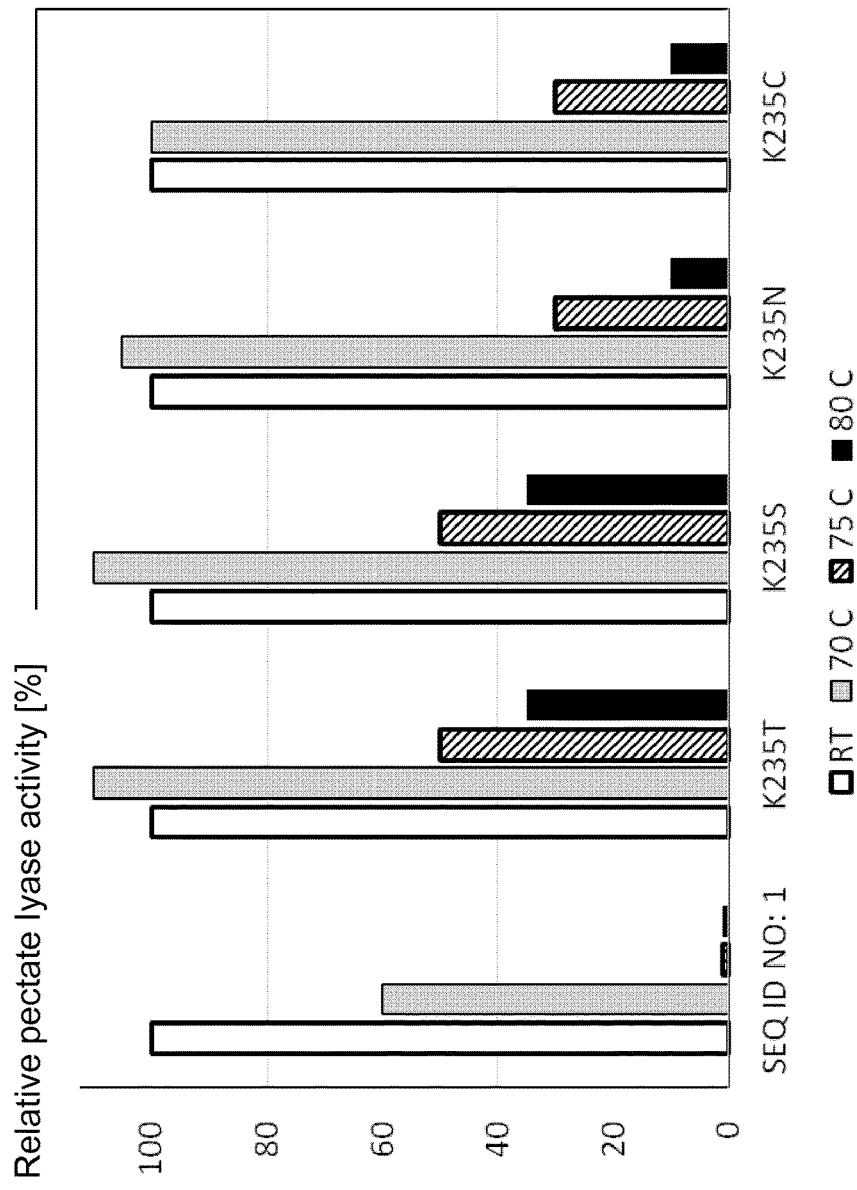

20 Claims, 6 Drawing Sheets
Specification includes a Sequence Listing.

US 10,246,696 B2

PECTINASES WITH IMPROVED THERMOSTABILITY

FIELD OF THE INVENTION

The invention is in the field of protein chemistry, in particular in the field of enzymology. It provides pectinases, i.e. polypeptides with pectin-degrading properties. In particular the invention provides polypeptides with pectate lyase activity (EC 4.2.2.2). Enzymes according to the invention have improved properties, such as improved thermostability.

BACKGROUND OF THE INVENTION

Plant cell wall degrading enzymes are carbohydrate-active enzymes that have been classified in different families based on homology criteria [http://www.cazy.org/, Cantarel et al., 2009, Nucleic Acids Res 37: D233-D238].

Pectate lyases (EC 4.2.2.2), are an important group of plant cell wall degrading enzymes. They cleave pectin using an eliminative cleavage of (1→4)-alpha-D-galacturonan yielding oligosaccharides with 4-deoxy-alpha-D-galact-4-enuronosyl groups at their non-reducing ends. They are mainly produced by plant pathogens and plant-associated organisms, and only rarely by animals. Pectate lyases are also commonly produced in bacteria, either by bacteria living in close proximity with plants or by gut bacteria that find plant material in the digestive tract of their hosts. [Hugouvieux-Cotte-Pattat et al., Environmental Microbiology reports (2014) doi 10, 1111/1758-2229, 12166].

Pectate lyases favor pectate, the anion, over pectin, the methylated ester, which is the preferred substrate of pectin lyase EC 4.2.2.10. Pectate lyases are also known under different names, such as alpha-1,4-D-endopolygalacturonic acid lyase, endo-alpha-1,4-polygalacturonic acid lyase, endogalacturonate transeliminase, endopectin methyltranseliminase, pectate transeliminase, pectic acid lyase, pectic acid transeliminase, pectic lyase, pectin trans-eliminase, PGA lyase, polygalacturonate lyase, polygalacturonic acid lyase, polygalacturonic acid trans-eliminase, polygalacturonic transeliminase and PPase-N.

When pectate lyases are used in industrial processes, it is often advantageous that they are stable at higher temperatures (thermostable) and resistant to alkaline conditions. Thermostable alkaline pectate lyases for instance have potential applications in the textile industry as an alternative to chemical-based ramie degumming processes. Such enzymes have been described, and have been isolated and characterized from bacterial sources, mainly Bacillus [Swarupa Rani Chiliveri et al., Carbohydrate Polymers (2014), 111: 264-272, Zhou et al., Appl Environ Microbiol (2015) 81: 5714-5723].

Cleavage by pectate lyases requires the presence of cations, such as manganese, nickel, iron, cobalt or calcium ions [Celia Marin-Rodriguez et al., J. Exp. Bot. (2002) 53: 2115-2119, Hugouvieux-Cotte-Pattat et al., Environmental Microbiology reports (2014) doi 10, 1111/1758-2229, 12166], with only rare exceptions [Kazemi-Pour et al., Proteomics (2004) 10: 3177-3186].

Recently, a thermostable pectate lyase was isolated from Bacillus, cloned, sequenced and characterized [Takao et al, Biosci. Biotechnol. Biochem. (2000) 64: 2360-2367, Takao et al., Biosci. Biotechnol. Biochem. (2001) 65: 322-329].

This enzyme was described to be thermostable when produced in a homologous expression system in Bacillus subtilis, and capable of resisting pre-incubation for 30 minutes at 70 degrees Celsius [Takao et al., Biosci. Biotechnol. Biochem. (2001) 65: 322-329]. However, pre-incubation at 80 degrees Celsius completely abolished the enzymatic activity. Because many industrial processes are preferably performed at temperatures above 70 degrees Celsius, there is a need in the art for even more thermostable or thermoresistant polypeptides with pectate lyase activity.

SUMMARY OF THE INVENTION

The present invention addresses this need in that it provides a pectate lyase with improved thermostable properties. More in particular, the invention provides a polypeptide with pectate lyase activity comprising an amino acid sequence that is at least 70% identical to the amino acid according to SEQ ID NO: 1, wherein the polypeptide comprises a small, polar, non-charged amino acid residue at an amino acid position corresponding to position 235 in SEQ ID NO: 1.

The invention also relates to a composition comprising a polypeptide as described above, a nucleic acid encoding a polypeptide as described above, a vector comprising such a nucleic acid and a composition comprising such a nucleic acid or a vector.

The invention also provides a recombinant host cell comprising a nucleic acid, a vector or a composition as described above.

Moreover, the invention relates to a method for producing a polypeptide as described above, comprising the steps of: culturing a recombinant host cell as described above, under conditions suitable for the production of the polypeptide, and recovering the polypeptide obtained, and optionally purifying the polypeptide.

In addition, the invention relates to a polypeptide as described above in an application selected from the group consisting of pulp delignification, degrading or decreasing the structural integrity of lignocellulosic material, textile dye bleaching, wastewater detoxifixation, xenobiotic detoxification, production of a sugar from a lignocellulosic material and recovering cellulose from a biomass.

The invention also relates to a method for improving the thermostability of a polypeptide with pectate lyase activity comprising an amino acid sequence that is at least 70% identical to the amino acid according to SEQ ID NO: 1, the method comprising the step of altering the amino acid at a position corresponding to position 235 in SEQ ID NO: 1 to a a small, polar, non-charged amino acid residue.

LEGEND TO THE FIGURES

FIG. 1: Diagram showing the relative pectate lyase activity of polypeptides according to SEQ ID NO: 1 (WT) and its K235 variants SEQ ID NO: 2 (K235T), SEQ ID NO: 3 (K235S), SEQ ID NO: 4 (K235N), and SEQ ID NO: 5 (K235C). Pectate lyase activity was determined after a pre-incubation of 10 minutes at elevated temperatures. RT=Room Temperature, 70 C is 70 degrees Celsius.

Figure 2:
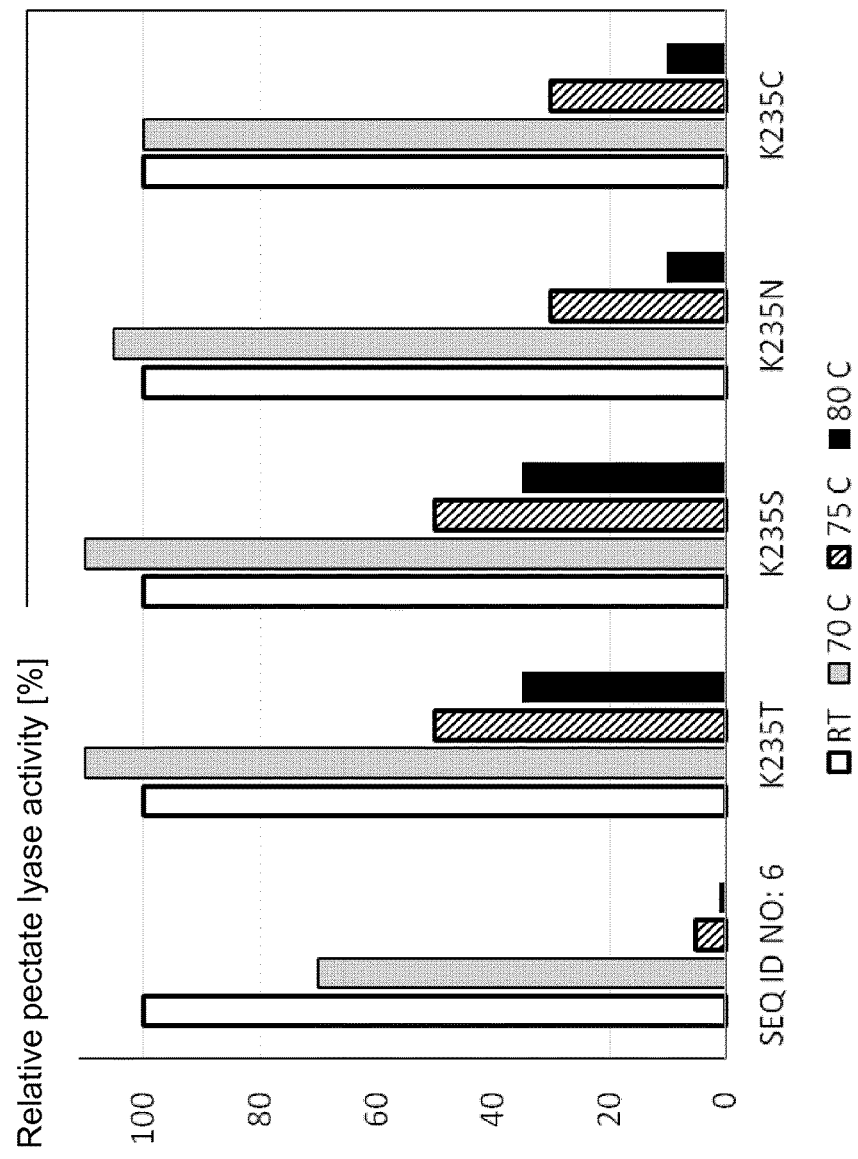

FIG. 2: Diagram showing the relative pectate lyase activity of polypeptides according to SEQ ID NO: 6 (93% identity with SEQ ID NO: 1), and its K235 variants SEQ ID NO: 7 (K235T), SEQ ID NO: 8 (K235S), SEQ ID NO: 9 (K235N), and SEQ ID NO: 10 (K235C). Pectate lyase activity was determined after a pre-incubation of 10 minutes at elevated temperatures. RT=Room Temperature, 70 C is 70 degrees Celsius.

Figure 3:
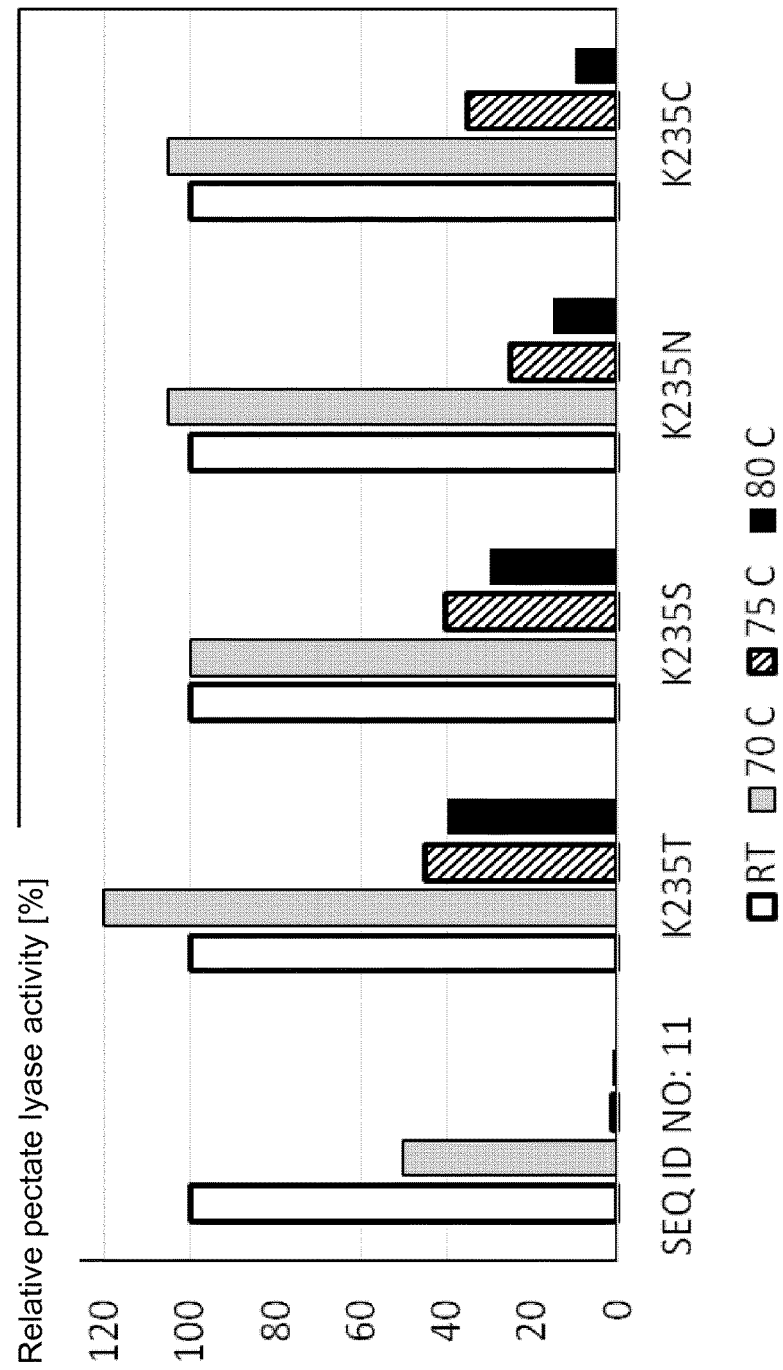

FIG. 3: Diagram showing the relative pectate lyase activity of polypeptides according to SEQ ID NO: 11 (89% identity with SEQ ID NO: 1), and its K235 variants SEQ ID NO: 12 (K235T), SEQ ID NO: 13 (K235S), SEQ ID NO: 14 (K235N), and SEQ ID NO: 15 (K235C). Pectate lyase activity was determined after a pre-incubation of 10 minutes at elevated temperatures. RT=Room Temperature, 70 C is 70 degrees Celsius.

Figure 4:
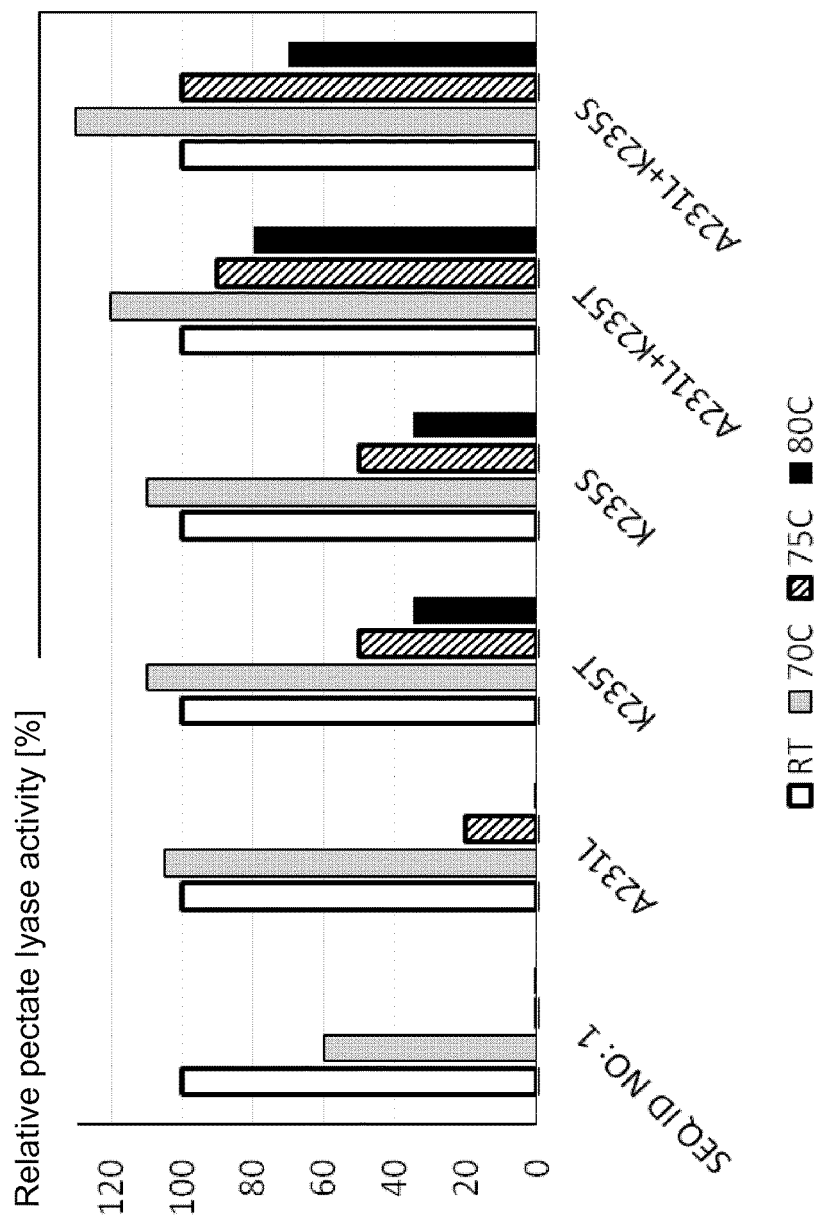

FIG. 4: Diagram showing the relative pectate lyase activity of polypeptides according to SEQ ID NO: 1 (WT) and its variants A231L, K235S, K235T, A231L+K235S and A231L+K235T. Pectate lyase activity was determined after a pre-incubation of 10 minutes at elevated temperatures. RT=Room Temperature, 70 C is 70 degrees Celsius.

Figure 5:
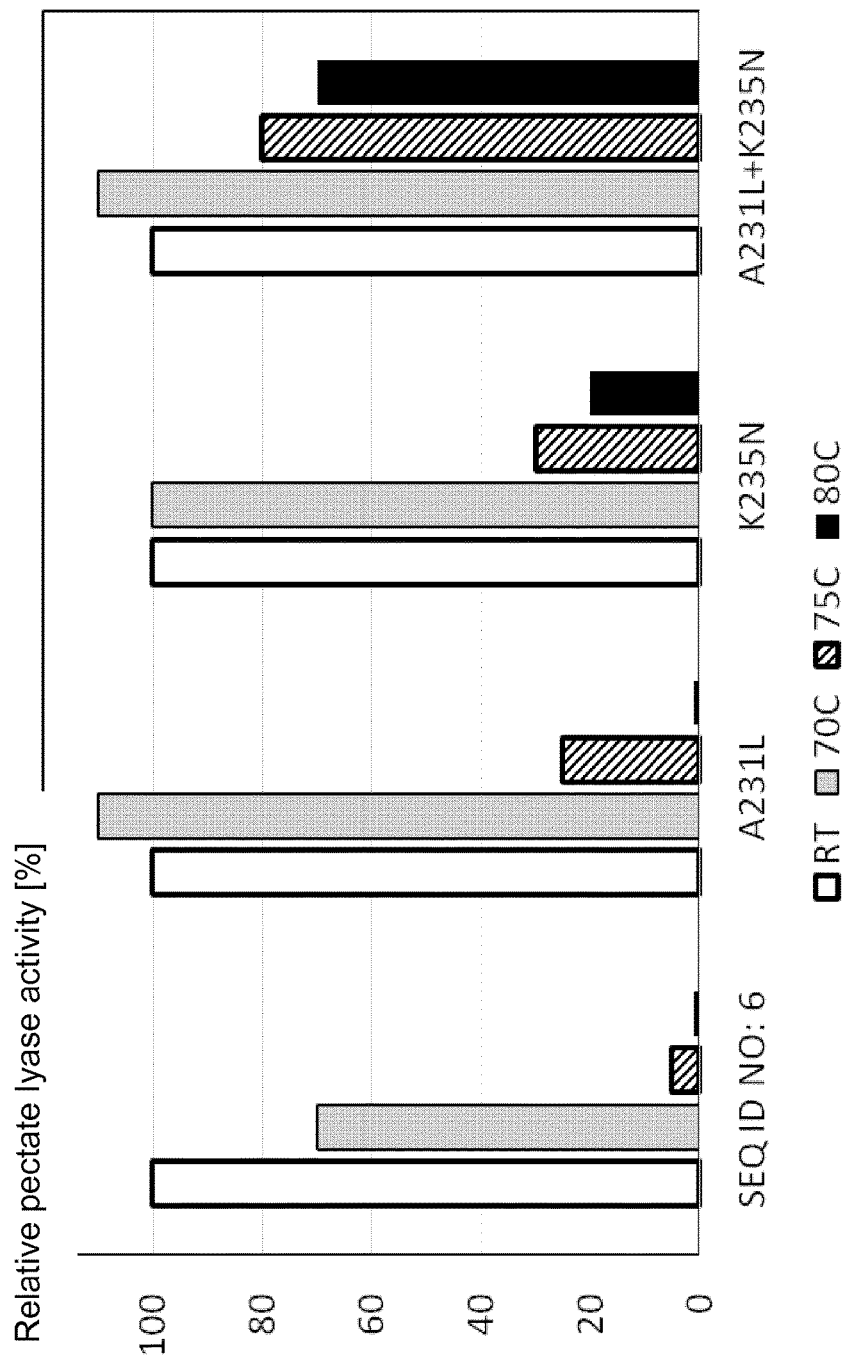

FIG. 5: Diagram showing the relative pectate lyase activity of polypeptides according to SEQ ID NO: 6 (93% identical with SEQ ID NO: 1) and its variants A231L, K235N and A231L+K235N. Pectate lyase activity was determined after a pre-incubation of 10 minutes at elevated temperatures. RT=Room Temperature, 70 C is 70 degrees Celsius.

Figure 6:
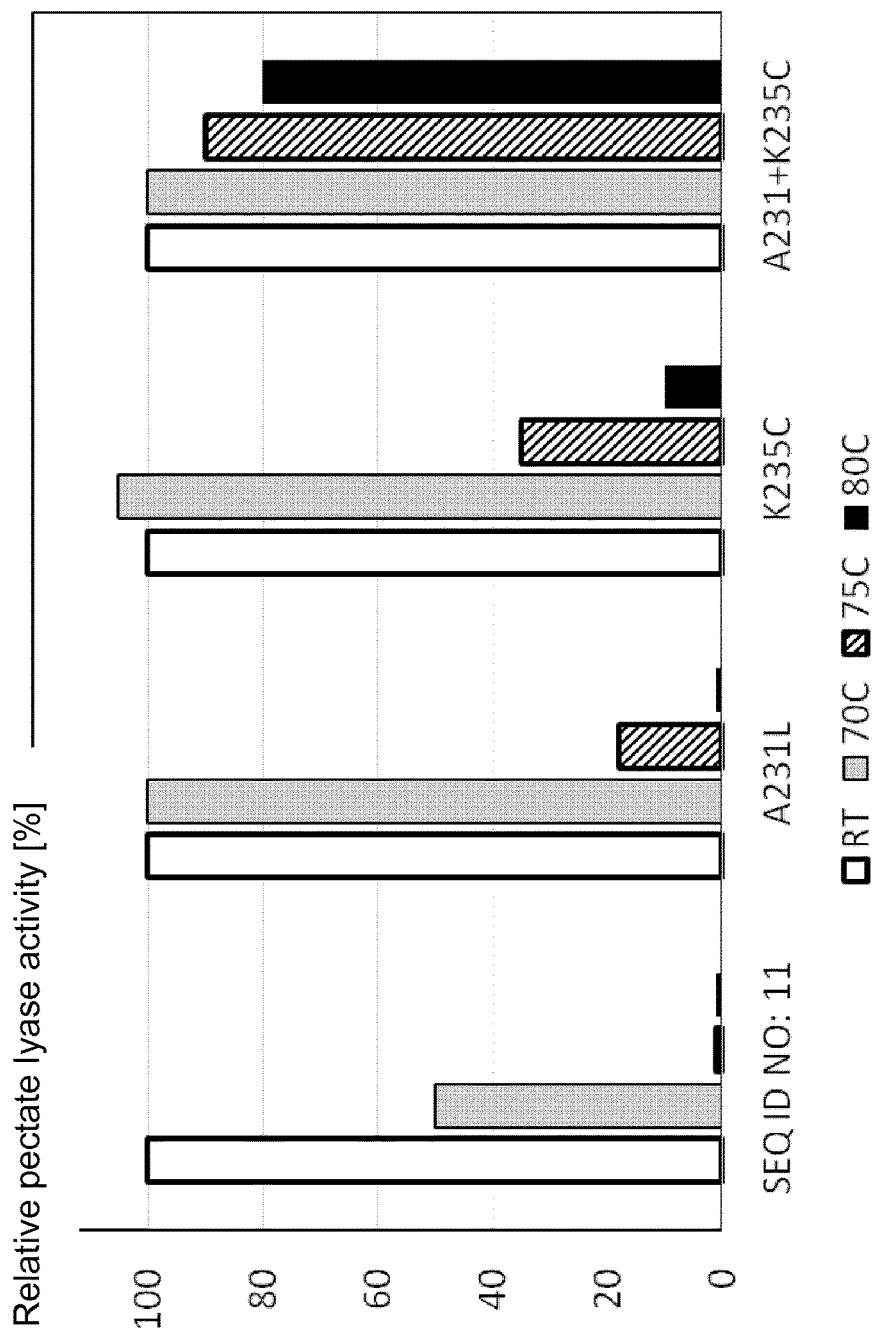

FIG. 6: Diagram showing the relative pectate lyase activity of polypeptides according to SEQ ID NO: 11 (89% identical with SEQ ID NO: 1) and its variants A231L, K235C and A231L+K235C. Pectate lyase activity was determined after a pre-incubation of 10 minutes at elevated temperatures. RT=Room Temperature, 70 C is 70 degrees Celsius.

DETAILED DESCRIPTION OF THE INVENTION

The present invention is based on our observation that a single amino acid substitution (K235 variant) in different pectate lyases improves their thermostability.

The term "amino acid substitution" is used herein the same way as it is commonly used, i.e. the term refers to a replacement of one or more amino acids in a protein with one or more other amino acids. Such an amino acid substitution may also be referred to as a mutation, a variation or a variant.

We observed the same phenomenon in pectate lyases that were homologous to the polypeptide with an amino acid sequence according to SEQ ID NO: 1. When the same amino acid variations were introduced at position 235 in polypeptides that were 93% and 89% identical to the polypeptide according to SEQ ID NO: 1, this also improved the thermostability of the homologous enzymes.

The invention thus relates to a polypeptide with pectate lyase activity comprising an amino acid sequence that is at least 70% identical to the amino acid according to SEQ ID NO: 1, wherein the polypeptide comprises a small, polar, non-charged amino acid residue at an amino acid position corresponding to position 235 in SEQ ID NO: 1.

Polypeptides with pectate lyase activity are also referred herein as pectate lyases, or pectate lyase enzymes.

The term "pectate lyase activity" is used herein to indicate the ability of a polypeptide to cleave pectin using an eliminative cleavage of (1→4)-alpha-D-galacturonan yielding oligosaccharides with 4-deoxy-alpha-D-galact-4-enuronosyl groups at their non-reducing ends.

The term "at least 70%" is used herein to include at least 71%, 72%, 73%, 74%, 75%, 76%, 77%, 78%, 79%, 80%, 82%, 83%,%, 85%, 88%, 87%, 88%, 89%, 90% or more, such as 91%, 92%, 93%, 94%, 95%, 99%, 97%, 98%, 99%, or even 100%.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2s eq&LINK_LOC=align2seq, Other commercial and open software such as Vector NTI are also suitable for this purpose, Introduction of a specific mutation in a recombinant gene is also among the routine skills of a molecular biologist. Specific guidance may be obtained from Methods in Molecular Biology Vol 182, "In vitro mutagenesis protocols", Eds Jeff Braman, Humana Press 2002. There are commercially available kits for performing site-directed mutagenesis (for example, QuikChange II XL Site-Directed Mutagenesis kit Agilent Technologies cat No 200521).

SEQ ID NO: 1 provides the amino acid sequence of a known polypeptide [Takao et al, Biosci. Biotechnol. Biochem. (2000) 64: 2360-2367, Takao et al., Biosci. Biotechnol. Biochem. (2001) 65: 322-329] with pectate lyase activity. We replaced the lysine residue at position 235 of SEQ ID NO: 1 with a small, polar, non-charged amino acid residue in order to obtain the K235 variants described herein. Exemplified herein are the variants K235T, K235C, K235S and K235N. This annotation is used herein to indicate a replacement of the amino acid residue corresponding to position 235 of SEQ ID NO: 1 with either one of the residues T (threonine), C (cysteine), S (serine) or N (asparagine), thereby obtaining the polypeptides according to SEQ ID NO: 2, SEQ ID NO: 3, SEQ ID NO: 4 and SEQ ID NO: 5, respectively. We found that the thermostability of the enzyme was thereby remarkably improved.

The term "mutant protein" or "mutation" is also used herein to refer to a polypeptide with pectate lyase activity as described herein, wherein the polypeptide comprises a small, polar, non-charged amino acid residue at an amino acid position corresponding to position 235 in SEQ ID NO: 1.

The term "wild type protein" is also used herein to indicate a polypeptide identical to the mutant protein, with the exception that it does not comprise a small, polar, non-charged amino acid residue at an amino acid position corresponding to position 235 in SEQ ID NO: 1.

The term "improved thermostability" in reference to a mutant polypeptide, as used herein, means that the mutant polypeptide has a higher residual pectate lyase activity than the corresponding wild type protein, after incubation for 10 minutes in 50 mM Tris-HCl pH 8.0 at a suitable temperature.

The term "suitable temperature" as used in this context refers to a temperature at which the wild type protein loses part of its pectate lyase activity after 10 minutes of incubation in 50 mM Tris-HCl pH 8.0. In other words, the term "suitable temperature" refers to a temperature chosen from a temperature range between temperatures X and Y, wherein X is the lowest temperature at which a wild type polypeptide shows a detectable loss of activity after 10 minutes of incubation in 50 mM Tris-HCl pH 8.0 and wherein temperature Y is the lowest temperature at which a wild type polypeptide loses all activity after 10 minutes of incubation in 50 mM Tris-HCl pH 8.0.

More specifically, in the thermostability assay, the polypeptides were heated to 70, 75 or 80 degrees Celsius for 10 minutes in 50 mM Tris-HCl at pH 8.0. The residual activity was measured at 60 degrees Celsius at pH 8.0 as described in example 5 and compared to the residual activity of the same polypeptides after preincubation at room temperature for 10 minutes. The results are shown in FIGS. 1-3.

In more detail, we measured the residual relative pectate lyase activity after heat treatment of polypeptides with an amino acid sequence according to SEQ ID NO: 2, SEQ ID NO: 3, SEQ ID NO: 4 and SEQ ID NO: 5 and compared this activity to that of a polypeptide with an amino acid sequence of SEQ ID NO: 1 after the same pre-treatment. We found that the introduction of the K235 mutation improved the thermostability of the pectate lyase enzyme.

This phenomenon appeared not to be restricted to the polypeptide with an amino acid sequence according to SEQ ID NO: 1, but was also observed in polypeptides homologous to the polypeptide according to SEQ ID NO: 1. Accordingly, we found that this amino acid position 235 could be changed in polypeptides with an amino acid sequence homologous to the sequence according to SEQ ID NO: 1 with the same effect. We constructed two pectate lyases that were 93% (SEQ ID NO: 6) and 89% (SEQ ID NO: 11) identical with the amino acid sequence according to SEQ ID NO: 1 and found that these two homologous enzymes also had an improved thermostability when the amino acid corresponding to position 235 in SEQ ID NO: 1 was changed to small, polar, non-charged amino acid residue.

Whereas the wild type sequence (SEQ ID NO: 1) only displayed 60% of its activity when pre-incubated at 70 degrees Celsius for 10 minutes, the variant polypeptides with the 235 mutation (K235T, K235S, K235N and K235C) were all at least as active as when pre-incubated at room temperature (table 1 and FIG. 1).

TABLE 1

Thermostability of SEQ ID NO: 1 and its K235 variants (Residual relative pectate lyase activity after pre-incubation at elevated temperatures).

| Temp | SEQ ID NO: 1 | K235T | K235S | K235N | K235C |
|---|---|---|---|---|---|
| RT | 100% | 100% | 100% | 100% | 100% |
| 70 C. | 60% | 110% | 110% | 105% | 100% |
| 75 C. | 1% | 50% | 50% | 30% | 30% |
| 80 C. | 1% | 35% | 35% | 10% | 10% |

Moreover, whereas the wild-type enzyme (WT, SEQ ID NO: 1) was not active anymore after pre-incubation at 75 degrees Celsius for 10 minutes, the K235 variants where active, even up to a level of 50% of the activity of the same enzyme, pre-incubated at room temperature for 10 minutes (FIG. 1).

Even more surprisingly, we found that the K235 variants were all able to resist pre-incubation at 80 degrees Celsius for 10 minutes, even up to a level of 35% of the activity of the same enzyme, pre-incubated at room temperature for 10 minutes (FIG. 1).

The expression "the amino acid corresponding to position 235 in SEQ ID NO: 1" is to be understood as follows. If such a position is to be determined in a given amino acid sequence that is at least 70% identical with the amino acid sequence according to SEQ ID NO: 1, then the two sequences are first to be aligned. That may be done by routine methods and software available in the art. The amino acid in the given amino acid sequence corresponding to amino acid 235 in SEQ ID NO: 1 is then the amino acid aligning with the lysine residue at position 235 in SEQ ID NO: 1.

We performed a homology search for proteins homologous to SEQ ID NO: 1 using SEQ ID NO: 1 as the query sequence in the "Standard protein BLAST" software, available at http://blast.ncbi.nlm.nih.gov/Blast.cgi?PROGRAM=blastp&PAGE_TYPE=BlastSearch&LINK_LOC=blasthome. More information on the software and database versions is available at the National Center for Biotechnology Information at National library of Medicine at National institute of Health internet site www.ncbi.nlm.nih.gov. Therein, a number of molecular biology tools including BLAST (Basic Logical Alignment Search Tool) is to be found. BLAST makes use of the following databases: All non-redundant GenBank CDS translations+PDB+SwissProt+PIR+PRF excluding environmental samples from WGS projects.

There were no polypeptides found comprising an amino acid sequence that is at least 70% identical to the amino acid according to SEQ ID NO: 1.

The term "amino acid variant", "variant", "mutant" or "sequence variant" or equivalent has a meaning well recognized in the art and is accordingly used herein to indicate an amino acid sequence that has at least one amino acid difference as compared to another amino acid sequence, such as the amino acid sequence from which it was derived.

We also constructed homologous polypeptides, having 93% and 89% sequence identity to the wild type sequence according to SEQ ID NO: 1. These homologous polypeptides are referred to herein as polypeptides according to SEQ ID NO: 6 (93% identical) and SEQ ID NO: 11 (89% identical).

We found that K235 variants of these polypeptides also had an improved thermostability (tables 2 and 3 and FIGS. 2 and 3).

TABLE 2

Therrnostability of SEQ ID NO: 6 and its K235 variants (Residual relative pectate lyase activity after pre-incubation at elevated temperatures)

| Temp | SEQ ID NO: 6 | K235T | K235S | K235N | K235C |
|---|---|---|---|---|---|
| RT | 100% | 100% | 100% | 100% | 100% |
| 70 C. | 70% | 100% | 105% | 100% | 105% |
| 75 C. | 5% | 60% | 40% | 30% | 20% |
| 80 C. | 1% | 40% | 35% | 20% | 10% |

TABLE 3

Thermostability of SEQ ID NO: 11 and its K235 variants (Residual relative pectate lyase activity after pre-incubation at elevated temperatures).

| Temp | SEQ ID NO: 11 | K235T | K235S | K235N | K235C |
|---|---|---|---|---|---|
| RT | 100% | 100% | 100% | 100% | 100% |
| 70 C. | 50% | 120% | 100% | 105% | 105% |
| 75 C. | 1% | 45% | 40% | 25% | 35% |
| 80 C. | 1% | 40% | 30% | 15% | 10% |

The term "improved thermostability" as used herein means that the K235 variant polypeptides exhibited more pectate lysase activity after preincubation at elevated temperatures as compared to the activity of the same polypeptides without the mutation at position 235, such as the wild type sequence (SEQ ID NO: 1) or the two homologous polypeptides according to SEQ ID NO: 6 and SEQ ID NO: 11 as described herein.

Thermostable pectate lyases have been described to be produced by bacteria of the genus *Bacillus* [Takao et al, Biosci. Biotechnol. Biochem. (2000) 64: 2360-2367, Takao et al., Biosci. Biotechnol. Biochem. (2001) 65: 322-329, Swarupa Rani Chiliveri et al., Carbohydrate Polymers (2014), 111: 264-272, Zhou et al., Appl Environ Microbiol (2015) 81: 5714-5723], hence in a preferred embodiment the invention relates to a polypeptide as described herein wherein the polypeptide is capable of being expressed in a bacterium, such as a *Bacillus* species, more preferably *Bacillus subtilis*.

We have shown that several polypeptides may be produced that are homologous to the wild-type sequence and still retain their pectate lyase activity. A BLAST search revealed that pectate lyases are available from bacterial origin, in particular from *Bacillus* species, with an identity as low as 52% or less as compared to SEQ ID NO: 1. The skilled person will therefore have no difficulty in constructing a polypeptide with pectate lyase activity that is at least 70% identical to the sequence of SEQ ID NO: 1 following the procedures and guidance provided herein. He will also be able to make the K235 variants as described herein, thereby obtaining a pectate lyase with an improved thermostability.

In a preferred embodiment, the invention relates to a polypeptide as described herein comprising an amino acid sequence that is at least 75% identical to the amino acid according to SEQ ID NO: 1, such as 80%, 85%, 89%, 90%, 91%, 92%, 93%, 94%, 95%, 96%, 97%, 98%, 99% or even 100%.

Recovery of a polypeptide according to the invention as produced by a host cell may be performed by any technique known to those skilled in the art. Possible techniques include, but are not limited to secretion of the protein into the expression medium, and purification of the protein from cellular biomass. The production method may further comprise a step of purifying the polypeptide obtained. For thermostable polypeptides, non-limiting examples of such methods include heating of the disintegrated cells and removing coagulated thermo labile proteins from the solution. For secreted proteins, non-limiting examples of such methods include ion exchange chromatography, and ultra-filtration of the expression medium. It is preferred that the purification method of choice is such that the purified protein retains its activity.

Accordingly, in a further preferred embodiment, the invention relates to a polypeptide as described herein wherein the polypeptide is an isolated polypeptide.

We have shown herein that the K235 variants as described herein have an improved thermostability.

The polypeptides as described herein may be used in compositions containing several additional components, such as stabilizers, fillers, cell debris, culture medium etcetera. Hence, the invention provides a composition comprising a polypeptide as described herein.

Polypeptides as described herein may be obtained by expressing a recombinant DNA in a heterologous expression system. The term "heterologous expression system" or equivalent means a system for expressing a DNA sequence from one host organism in a recipient organism from a different species or genus than the host organism. The most prevalent recipients, known as heterologous expression systems, are chosen usually because they are easy to transfer DNA into or because they allow for a simpler assessment of the protein's function. Heterologous expression systems are also preferably used because they allow the upscaling of the production of a protein encoded by the DNA sequence in an industrial process. Preferred recipient organisms for use as heterologous expression systems include bacterial, fungal and yeast organisms, such as for example *Escherichia coli, Bacillus, Corynebacterium, Pseudomonas, Pichia pastoris, Saccharomyces cerevisiae, Yarrowia lipolytica*, filamentous fungi and many more systems well known in the art.

The presently disclosed polypeptides or proteins may be fused to additional sequences, by attaching or inserting, including, but not limited to, affinity tags, facilitating protein purification (S-tag, maltose binding domain, chitin binding domain), domains or sequences assisting folding (such as thioredoxin domain, SUMO protein), sequences affecting protein localization (periplasmic localization signals etc), proteins bearing additional function, such as green fluorescent protein (GFP), or sequences representing another enzymatic activity. Other suitable fusion partners for the presently disclosed polypeptides are known to those skilled in the art.

The present invention also relates to polynucleotides encoding any of the pectate lyase variants disclosed herein. Means and methods for cloning and isolating such polynucleotides are well known in the art.

Furthermore, the present invention relates to a vector comprising a polynucleotide according to the invention, optionally operably linked to one or more control sequences. Suitable control sequences are readily available in the art and include, but are not limited to, promoter, leader, polyadenylation, and signal sequences.

Pectate lyase variants according to various embodiments of the present invention may be obtained by standard recombinant methods known in the art. Briefly, such a method may comprise the steps of: culturing a recombinant host cell as described above under conditions suitable for the production of the polypeptide, and recovering the polypeptide obtained. The polypeptide may then optionally be further purified.

A large number of vector-host systems known in the art may be used for recombinant production of the pectate lyases as described herein. Possible vectors include, but are not limited to, plasmids or modified viruses which are maintained in the host cell as autonomous DNA molecule or integrated in genomic DNA. The vector system must be compatible with the host cell used as is well known in the art. Non-limiting examples of suitable host cells include bacteria (e.g. *E. coli*, bacilli), yeast (e.g. *Pichia Pastoris, Saccharomyces Cerevisiae*), fungi (e.g. filamentous fungi) insect cells (e.g. Sf9).

In yet other terms, the invention relates to a method for improving the thermostability of a polypeptide with pectate lyase activity comprising an amino acid sequence that is at least 70% identical to the amino acid according to SEQ ID NO: 1, the method comprising the step of altering the amino acid at a position corresponding to position 235 in SEQ ID NO: 1 to a small, polar, non-charged amino acid residue.

Surprisingly, we found that the thermostability of the above described K235 variant polypeptides could be even further improved if another variation was introduced in addition to the K235 variation. We introduced an A231L variant into SEQ ID NO: 1 and found that this variation on its own improved the thermostability of the polypeptide (table 4, FIG. 4).

As used herein, the term "A231L variant" indicates that the amino acid corresponding to the residue at position 231 of SEQ ID NO: 1 (alanine) is replaced by a leucine residue.

TABLE 4

Thermostability of a polypeptide according to SEQ ID NO 1 and its variants (Residual relative pectate lyase activity after pre-incubation at elevated temperatures).

| Temp | SEQ ID NO: 1 | A231L | K235T | K235S | A231L + K235T | A231L + K235S |
|---|---|---|---|---|---|---|
| RT | 100% | 100% | 100% | 100% | 100% | 100% |
| 70 C. | 60% | 105% | 110% | 110% | 120% | 130% |
| 75 C. | 1% | 20% | 50% | 50% | 90% | 100% |
| 80 C. | 1% | 1% | 35% | 35% | 80% | 70% |

Surprisingly, the polypeptides carrying both the A231L variation and the K235 variations were more thermostable than each of the variant polypeptides alone. The effect was even found to be synergistic. Whereas the polypeptide according to SEQ ID NO: 1 did not have any significant residual activity after pre-incubation at 75 degrees C., the A231L variant as well as the K235T and K235S variants retained 20%, 50% and 50% of their activity relative to the activity after pre-incubation at room temperature (relative activity, table 4 and FIG. 4). When both the A231L and K235T mutations were introduced into SEQ ID NO: 1, the relative activity of this double mutant (after pre-incubation at 75 C) improved to 90%. The same effect was found for the A231L and K235S double mutant of the polypeptide according to SEQ ID NO: 1. Therein the activity of the double mutant remained at 100% after pre-incubation at 75 degrees Celsius for 10 minutes.

Most remarkably, the double mutants were exceptionally active after pre-incubation at 80 degrees Celsius. Whereas the A231L variant of SEQ ID NO: 1 was no longer active after pre-incubation at 80 degrees Celsius, in combination with the K235 variants, it improved the thermostability from K235T variant from 35% to 80% and the thermostability of the K235S variant from 35 to 70% (table 4, FIG. 4)

We further investigated if this phenomenon also occurred with polypeptides that were homologous to the polypeptide according to SEQ ID NO: 1. For that purpose we introduced the A231L single and double mutations in polypeptides according to SEQ ID NO: 6 and 11 (93% and 89% identical with SEQ ID NO: 1 respectively).

We observed that the thermostability of these polypeptides could also be improved in the same manner as described above for the polypeptide according to SEQ D NO: 1.

The single mutation A231L in SEQ ID NO: 6 improved the thermostability as shown in table 5. The double mutant A231L plus K235N improved the thermostability synergistically, i.e. more than the sum of the contributions of each of the mutations separately. After pre-incubation at 75 degrees Celsius, the relative activity of the A231L and K235N variants still was 25% and 30% respectively, whereas the combination of both mutations resulted in 80% relative activity.

Most remarkably, the double mutants were exceptionally active after pre-incubation at 80 degrees Celsius. The A231L variant of SEQ ID NO: 1 was not significantly active after pre-incubation at 80 degrees Celsius. However, in combination with the K235N variant, it improved the thermostability of the double mutant from 20% to 70% (table 5, FIG. 5).

TABLE 5

Thermostability of a polypeptide according to SEQ ID NO 6 and its variants (Residual relative pectate lyase activity after pre-incubation at elevated temperatures).

| Temp | SEQ ID NO: 6 | A231L | K235N | A231L + K235N |
|---|---|---|---|---|
| RT | 100% | 100% | 100% | 100% |
| 70 C. | 70% | 110% | 100% | 110% |
| 75 C. | 5% | 25% | 30% | 80% |
| 80 C. | 1% | 1% | 20% | 70% |

The single mutation A231L in SEQ ID NO: 11 improved the thermostability as shown in table 6. The double mutant A231L plus K235C improved the thermostability synergistically, i.e. more than the sum of the contributions of each of the mutations separately. After pre-incubation at 75 degrees Celsius, the A231L and K235C variants still had 18% and 35% relative activity respectively, whereas the combination of both mutations resulted in 90% relative activity.

Most remarkably, the double mutants were exceptionally active after pre-incubation at 80 degrees Celsius. The A231L variant of SEQ ID NO: 11 was not significantly active after pre-incubation at 80 degrees Celsius. However, in combination with the K235C variant, it improved the thermostability of the double mutant from 10% to 80% (table 6, FIG. 6).

TABLE 6

Thermostability of a polypeptide according to SEQ ID NO 11 and its variants (Residual relative pectate lyase activity after pre-incubation at elevated temperatures).

| Temp | SEQ ID NO: 11 | A231L | K235C | A231 + K235C |
|---|---|---|---|---|
| RT | 100% | 100% | 100% | 100% |
| 70 C. | 50% | 100% | 105% | 100% |
| 75 C. | 1% | 18% | 35% | 90% |
| 80 C. | 1% | 1% | 10% | 80% |

Hence, the invention also relates to a K235 variant polypeptide as described above additionally comprising a leucine residue at an amino acid position corresponding to position 231 in SEQ ID NO: 1.

The invention also relates to a method for improving the thermostability of a polypeptide with pectate lyase activity comprising an amino acid sequence that is at least 70% identical to the amino acid according to SEQ ID NO: 1, the method comprising the step of altering the amino acid at a position corresponding to position 235 in SEQ ID NO: 1 to a small, polar, non-charged amino acid residue and altering the amino acid at a position corresponding to position 231 in SEQ ID NO: 1 to a leucine residue.

In a further preferred embodiment, the invention relates to any of the methods as described above, wherein the polypeptide with pectate lyase activity is capable of being expressed in a bacterium, such as a *Bacillus* species, more preferably *Bacillus subtilis*.

The polypeptides with pectate lyase activity according to the present invention may be used in a wide range of different industrial processes and applications, such as cellulose recovery from lignocellulosic biomass, decreasing the energy required for the refining of wood and production of a sugar from a lignocellulosic material. They may also be used in wood pulp preparation, in pulp delignification, textile dye bleaching, wastewater detoxifixation, xenobiotic detoxification, degrading or decreasing the structural integrity of lignocellulosic material and detergent manufacturing.

EXAMPLES

Example 1: Preparation of a Polypeptide According to SEQ ID NO: 1

The DNA construct disclosed in Takao et al., Biosci. Biotechnol. Biochem. (2001) 65: 322-329 encoding the polypeptide according to SEQ ID NO: 1 was optimized for expression in *E. coli* and commercially synthesized and cloned into a standard plasmid vector pET28a+ under the control of T7-RNA-polymerase promoter for expression in *Escherichia coli* BL21(DE3). The nucleotide sequence of the construct is provided herein as SEQ ID NO: 16.

Example 2: Preparation of Variants of a Polypeptide According to SEQ ID NO: 1 with Pectate Lyase Activity Homologous protein sequences (according to SEQ ID NO: 6 and SEQ ID NO: 11) were generated by random mutagenesis of SEQ ID NO:s 16 and SEQ ID NO: 21 using error-prone PCR essentially as described (Curr Protoc Mol Biol. 2001 May; Chapter 8: Unit 8.3. doi: 10.1002/0471142727.mb0803s51, Random mutagenesis by PCR. Wilson DS1, Keefe AD) using a commercial random PCR mutagenesis kit (QuikChange® II XL Site-Directed Mutagenesis kit by Agilent Technologies). More in particular, the DNA sequence of SEQ ID NO: 21 was obtained from SEQ ID NO: 16 encoding the polypeptide according to SEQ ID NO: 1. The DNA sequence of SEQ ID NO: 26 was obtained by random mutagenesis of SEQ ID NO: 21 encoding the polypeptide according to SEQ ID NO: 6. SEQ ID NO: 26 is the DNA sequence encoding the polypeptide according to SEQ ID NO: 11.

PCR fragments resulting from error-prone PCR were cloned to the plasmid vector pET28a+ under the control of T7-RNA-polymerase promoter for expression in *Escherichia coli* BL21 (DE3), and screened for pectate lyase activity of the recombinant proteins.

Active clones were subjected to further rounds of randomization using the same protocol. The polypeptide according to SEQ ID NO: 6 exhibited pectate lyase activity and was found to be 93% identical with SEQ ID NO: 1. The polypeptide according to SEQ ID NO: 11 also exhibited pectate lyase activity and was found to be 89% identical with SEQ ID NO: 1.

Example 3: Preparation of A231L and K235 Variant Polypeptides

In order to prepare polypeptide according to SEQ ID NO:s 2-5, mutations were inserted into the DNA coding for polypeptide according to SEQ ID NO: 1 at position 235. As a result, the lysine residue from that position in SEQ ID NO: 1 was replaced with either one of the residues T (threonine), C (cysteine), S (serine) or N (asparagine), thereby resulting in the polypeptides according to SEQ ID NO: 2, SEQ ID NO: 3, SEQ ID NO: 4 and SEQ ID NO: 5, respectively.

These variants are referred to herein as K235T, K235S, K235N and K235C respectively.

This was achieved by standard site-directed mutagenesis essentially as described in WO 2013/038062. In more detail: To introduce mutation A231L into the genes encoding SEQ ID NO: 1, SEQ ID NO: 6 and SEQ ID NO: 11, we carried out two separate PCR reactions:

(1) with primers Primer 1 gaaattaatacgactcactatagg (SEQ ID NO: 31) and Primer 2(A231 L) GCCATCATGCTGCT-GAAACGGACGACCAAAATAGGTG (SEQ ID NO: 38), (2) with Primer3(A231L) GGTCGTCCGTTTCAGCAG-CATGATGGCctgCTGGATATC (SEQ ID NO: 39) and Primer 4 ggttatgctagttattgctcagcggtg (SEQ ID NO: 32).

In both reactions, recombinant gene without the mutation was used as the template. Primers 1 and 4 bind inside the vector sequence and are not specific to the recombinant gene. Primers 2 and 3 bind inside the recombinant gene and their binding sites overlap. Primer 3 binding site contains the mutation site. Primer 3 represents the mutated (desired) sequence, which is not 100% matching the template (lower case type font in the primer sequence indicates the mismatched nucleotides). However, the primer has enough affinity and specificity to the binding site to produce the desired PCR product. Purified PCR products from reactions (1) and (2) were combined and used as template for PCR reaction with Primer 1 and Primer 4. The products of this reaction, containing the A231L variant sequence of the genes encoding the polypeptides according to SEQ ID NO:s 48-50 was cloned in a plasmid vector for expression in *E. coli*.

The same protocol and the same primers 1 and 4 were used for introducing the K235 mutations into the genes encoding the polypeptide according to SEQ ID NO: 1, SEQ ID NO: 6 and SEQ ID NO: 11. Primer 3 used for introducing the K235 mutations was AATAGCAGCGATTTTATCAC-CATCAGCTACAACGTGTTTA (SEQ ID NO: 37). The specific Primers 2 used for the mutations K235T, K235S, K235N and K235C are listed in table 7.

TABLE 7 primers used for introducing the 231 and 235 mutations.

| Seq ID NO: | Primer name | Sequence (5'-3') |
|---|---|---|
| 31 | Primer 1 | GAAATTAATACGACTCACTATAGG |
| 32 | Primer 4 | GGTTATGCTAGTTATTGCTCAGCGGTG |
| 33 | Primer 2 K235T | GCTGATGGTGATAAAATCGCTGCTATTggTGATATCCAG |
| 34 | Primer 2 K235S | GCTGATGGTGATAAAATCGCTGCTATTgcTGATATCCAG |
| 35 | Primer 2 K235N | GCTGATGGTGATAAAATCGCTGCTATTgTTGATATCCAG |
| 36 | Primer 2 K235C | GCTGATGGTGATAAAATCGCTGCTATTgcaGATATCCAG |

TABLE 7-continued primers used for introducing the 231 and 235 mutations.

| Seq ID NO: | Primer name | Sequence (5'-3') |
|---|---|---|
| 37 | Primer 3 K235 | AATAGCAGCGATTTTATCACCATCAGCTACAACGTGTTTA |
| 38 | Primer 2 A231 | GCCATCATGCTGCTGAAACGGACGACCAAAATAGGTG |
| 39 | Primer 3 A231L | GGTCGTCCGTTTCAGCAGCATGATGGCctgCTGGATATCA |

Double mutants were prepared by introducing the mutation into the DNA encoding a polypeptide carrying a single mutation.

Example 4: Heterologous Expression of Polypeptides with Pectate Lyase Activity For recombinant expression in *E. coli*, recombinant genes were cloned into pET-28 commercial expression vector under the control of T7 bacteriophage promoter.

Protein production was carried out in *E. coli* BL21(DE3) strain according to the plasmid manufacturer protocol available at http://richsingiser.com/4402/Novagen%20pET%20system%20manual.pdf. The incubation temperature for protein production was 30 degrees C., which was found optimal for maximum yield of the active protein. Cells were lysed using lysis buffer (50 mM Tris-HCl pH7.4, 1% Triton X100, 0.5 mM CaCl) and heated at 60 degrees C. for 20 min. Coagulated cell debris was removed by centrifugation. The thermostable recombinant pectate lyases were detected in the soluble fraction only, consistent with the notion that they were thermostable enzymes.

Example 5: Pectate Lyase Activity Assay

Pectate lyase activity assay was carried out essentially as described in Takao M, Nakaniwa T, Yoshikawa K, Terashita T, Sakai T., "Purification and characterization of thermostable pectate lyase with protopectinase activity from thermophilic *Bacillus* sp. TS 47". Biosci Biotechnol Biochem. 2000 64:2360-7. In more detail, pectate lyase activity was assayed by measuring the increase in absorbance at 235 nm of the reaction mixture. Polygalacturonic acid (PGA) sodium salt from de-methylated citrus pectin (purchased from MegaZyme) was used as substrate. A reaction mixture containing 1 ml of 0.1% PGA in 10 mM Tris-HCl buffer, pH 8.0 and 0.5 mM CaCl2, and an appropriate amount of enzyme solution was incubated for 30 min at 60 C.

The reaction was stopped by placing the mixture in 100 degrees C. (boiling water bath) for 5 min. Relative pectate lyase activity was was calculated from the difference in absorption of the reaction mixture at 235 nm at the start and at the end of the reaction.

Example 6: Thermostability of Polypeptides with Pectate Lyase Activity

Thermostability of the polypeptides with pectate lyase activity was determined by pre-incubation for 10 minutes in 50 mM Tris-HCl pH 8.0, either at room temperature (control) or at 70 degrees C., 75 degrees C. and 80 degrees C. before measuring their activity according to example 5.

After pre-incubation, the samples were brought to 60 degrees C., substrate (PGA) was added and samples were assayed for activity as described in Example 5 at 60 degrees C. pH 8.0. Residual activities for each sample were calculated as % of the activity of the corresponding sample pre-incubated at room temperature (control sample).

Example 7: Sequences Provided Herein

Amino acid sequence and nucleotide sequences are provided herewith in the WIPO ST_25 standard. For convenience the sequences are also provided in table 8.

SEQ ID NO: 1 is derived from the prior art and has been disclosed in Takao et al, Biosci. Biotechnol. Biochem. (2000) 64: 2360-2367 and in Takao et al., Biosci. Biotechnol. Biochem. (2001) 65: 322-329.

Amino acids corresponding to positions 231 and 235 in SEQ ID NO: 1 are shown in bold and underlined type face.

SEQ ID NO: 6 was obtained by random mutagenesis of the DNA encoding SEQ ID NO: 1 (shown herein as SEQ ID NO: 16) as described in example 2.

SEQ ID NO: 11 was obtained by random mutagenesis of the DNA encoding SEQ ID NO: 6 (shown herein as SEQ ID NO: 21).

The DNA encoding the polypeptide according to SEQ ID NO: 11 is shown herein as SEQ ID NO: 26.

The amino acids deviating from the wild type sequence of SEQ ID NO: 1 are shown in capital letters.

The polypeptide according to SEQ ID NO: 6 is a homologue of the polypeptide according to SEQ ID NO: 1. These two polypeptides have 385 of the 416 amino acids in common, in other words they are 93% identical.

The polypeptide according to SEQ ID NO: 11 is also a homologue of the polypeptide according to SEQ ID NO: 1. These two polypeptides have 369 of the 416 amino acids in common, in other words they are 89% identical.

The polypeptides according to SEQ ID NO:s 2-5 correspond to the polypeptide according to SEQ ID NO: 1 with variations K235T, K235S, K235N and K235C respectively.

The polypeptides according to SEQ ID NO:s 7-10 correspond to the polypeptide according to SEQ ID NO: 6 with variations K235T, K235S, K235N and K235C respectively.

The polypeptides according to SEQ ID NO:s 12-15 correspond to the polypeptide according to SEQ ID NO: 11 with variations K235T, K235S, K235N and K235C respectively.

The nucleotide sequences according to SEQ ID NO:s 16-30 encode the polypeptides with amino acid sequences according to SEQ ID NO:s 1-15 respectively.

SEQ ID NO:s 31-39 correspond to the primers used for producing the variant polypeptides as detailed in example 3.

Polypeptides carrying the double mutations A231L with K235T, K235S, K235N and K235C double mutations are shown in SEQ ID NO: 40-43 respectively.

DNA encoding the polypeptides according to SEQ ID NO: 40-43 are shown in SEQ ID NO: 44-47.

SEQ ID NO:s 48, 49 and 50 correspond to variants A231L in polypeptides according to SEQ ID NO: 1, 6 and 11 respectively. SEQ ID NO:s 51-53 are the DNA sequences encoding the polypeptides according to SEQ ID NO:s 48-50

TABLE 8

Amino acid and nucleotide sequences disclosed herein.

| SEQ ID NO: | Sequence |
|---|---|
| 1 | 1 kelghevlkp ydgwaaygeg ttggamaspq nvfvvtnrte liqalggnnh tnqynsvpki<br>61 iyvkgtidln vddnnqpvgp dfykdphfdf eaylreydpa twgkkevegp leearvrsqk<br>121 kqkdrimvyv gsntsiigvg kdakikgggf liknvdnvii rniefeapld yfpewdptdg<br>181 tlgewnseyd sisiegsshi widhntftdg dhpdrslgty fgrpfqqhdg aldi<u>k</u>nssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svpalvkaka gagnlh |
| 2 | 1 kelghevklp ydgwaaygeg ttggamaspq nvfvvtnrte liqalggnnh tnqynsvpki<br>61 iyvkgtidln vddnnqpvgp dfykdphfdf eaylreydpa twgkkevegp leearvrsqk<br>121 kqkdrimvyv gsntsiigvg kdakikgggf liknvdnvii rniefeapld yfpewdptdg<br>181 tlgewnseyd sisiegsshi widhntftdg dhpdrslgty fgrpfqqhdg aldi<u>t</u>nssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svpalvkaka gagnlh |
| 3 | 1 kelghevlkp ydgwaaygeg ttggamaspq nvfvvtnrte liqalggnnh tnqynsvpki<br>61 iyvkgtidln vddnnqpvgp dfykdphfdf eaylreydpa twgkkevegp leearvrsqk<br>121 kqkdrimvyv gsntsiigvg kdakikgggf liknvdnvii rniefeapld yfpewdptdg<br>181 tlgewnseyd sisiegsshi widhntftdg dhpdrslgty fgrpfqqhdg aldi<u>s</u>nssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svaplvkaka gagnlh |
| 4 | 1 kelghevlkp ydgwaaygeg ttggamaspq nvfvvtnrte liqalggnnh tnqynsvpki<br>61 iyvkgtidln vddnnqpvgp dfykdphfdf eaylreydpa twgkkevegp leearvrsqk<br>121 kqkdrimvyv gsntsiigvg kdakikgggf liknvdnvii rniefeapld yfpewdptdg<br>181 tlgewnseyd sisiegsshi widhntftdg dhpdrslgty fgrpgqqhdg aldi<u>n</u>nssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svpalvkaka gagnlh |
| 5 | 1 kelghevlkp ydgwaaygeg ttggamaspq nvfvvtnrte liqalggnnh tnqynsvpki<br>61 iyvkgtidln vddnnqpvgp dfykdphfdf eaylreydpa twgkkevegp leearvrsqk<br>121 kqkdrimvyv gsntsiigvg kdakikgggf liknvdnvii rniefeapld yfpewdptdg<br>181 tlgewnsyd sisiegsshi widhntftdg dhpdrslgty fgrpfqqhdg aldi<u>c</u>nssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svpalvkaka gagnlh |
| 6 | 1 kelghDvlkp ydgwaSygeg ttggSmaspq nvYTvtnKte lVqalggnnh tnqynsvpki<br>61 iyvkgtiEln vddnnqpvgp EfykdphYdf eaylKeydpK KwgkkevSgp leearArsqk<br>121 kqkEriVvNv gsntsiigvg kdakiVgggf liknvdnvii rniefeapVd yfpewdptdg<br>181 tlgewnseyd siTiegsHhi widhntftdg dhpdKslgty fgrpfqqhdg aldi<u>k</u>nssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvswknee smyESgtivd<br>361 lpngrryidl vasynesntl qlkkevGwkp mfyhvihptp svpalvkaka gagnlh |
| 7 | 1 kelghDvlkp ydgwaSygeg ttggSmaspq nvYTvtnKte lVqalggnnh tnqynsvpki<br>61 yyvkgtiEln vddnnqpvgp EfykdphYdf eaylKeydpK KwgkkevSgp leearArsqk<br>121 kqkEriVvNv gsntsiigvg kdakiVgggf liknvdnvii rniefeapVd yfpewdptdg<br>181 tlgewnseyd siTiegsHhi widhntftdg dhpdKslgty fgrpfqqhdg aldi<u>t</u>nssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvwsknee smyESgtivd<br>361 lpngrryidl vasynesntl qlkkevGwkp mfyhvihptp svpalvkaka gagnlh |
| 8 | 1 kelghDvlkp ydgwaSygeg ttggSmaspq nvYTvtnKte lVqalggnnh tnqynsvpki<br>61 iyvkgtiEln vddnnqpvgp EfykdphYdf eaylKeydpK KwgkkevSgp leearArsqk<br>121 kqkEriVvNv gsntsiigvg kdakiVgggf liknvdnvii rniefeapVd yfpewdptdg<br>181 tlgewnseyd siTiegsHhi widhntftdg dhpdKslgty fgrpfqqhdg aldi<u>s</u>nssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvwsknee smyESgtivd<br>361 lpngrryidl vasynesntl qlkkevGwkp mfyhvihptp svpalvkaka gagnlh |
| 9 | 1 kelghDvlkp ydgwaSygeg ttggSmaspq nvYTvtnKte lVqalggnnh tnqynsvpki<br>61 iyvkgtiEln vddnnqpvgp EfykdphYdf eaylKeydpK KwgkkevSgp leearArsqk<br>121 kqkEriVvNv gsntsiigvg kdakiVgggf liknvdnvii rniefeapVd yfpewdptdg<br>181 tlgewnseyd siTiegsHhi widhntftdg dhpdKslgty fgrpgqqhdg aldi<u>n</u>nssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvwsknee smyESgtivd<br>361 lpngrryidl vasynesntl qlkkevGwkp mfyhvihptp svpavvkaka gagnlh |

TABLE 8-continued

Amino acid and nucleotide sequences disclosed herein.

| SEQ ID NO: | Sequence |
|---|---|
| 10 | 1 kelghDvlkp ydgwaSygeg ttggSmaspq nvYTvtnKte lVqalggnnh tnqynsvpki<br>61 iyvkgtiEln vddnnqpvgp EfykdphYdf eaylKeydpK KwgkkevSgp leearArsqk<br>121 kqkEriVvNv gsntsiigvg kdakiVgggf liknvdnvii rniefeapVd yfpewdptdg<br>181 tlgewnseyd siTiegsHhi widhntftdg dhpdKslgty fgrpfqqhdg aldi<u>c</u>nssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 11 | 1 kelghDvlkp NdgwaSygeg ttggSEaspD nvYTvtnKSe lVqalggnnh tnqynsTpki<br>61 iyvkgtiEln vddnnqpvgp EYyDdphYdf eaylKeydpK KwgkkevSgp leearArsqk<br>121 kqkEriVvNv gsntsiigvg kdakiVgggf liknvdnvii rniefeapVd Ffpewdptdg<br>181 EYgewnseyd siTieSsHhi widhntftdg dhpdKslgty fgrpfqqhdg aldi<u>k</u>nssdf<br>241 itisynvfKD hdkvSligSs dsrKTdEghl Kvtlhhnyyk nvtqrlprvr fgqvhiynny<br>301 yetsnladyd fqyawgvgvE sKiyaqnnyt stdwdidpsK iikvwsknee smyeSgtivd<br>361 lpngrryidl vasynesntl qlkkevGwkp mfyhvihptp svpalvkaka gagnlh |
| 12 | 1 kelghDvlkp NdgwaSygeg ttggSEaspD nvYTvtnKSe lVqalggnnh tnqynsTpki<br>61 iyvkgtiEln vddnnqpvgp EYyDdphYdf eaylKeydpK KwgkkevSgp leearArsqk<br>121 kqkEriVvNv gsntsiigvg kdakiVgggf liknvdnvii rniefeapVd Ffpewdptdg<br>181 EYgewnseyd siTieSsHhi widhntftdg dhpdKslgty fgrpfqqhdg aldi<u>t</u>nssdf<br>241 itisynvfKD hdkvSligSs dsrKTdEghl Kvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 13 | 1 kelghDvlkp NdgwaSygeg ttggSEaspD nvYTvtnKSe lVqalggnnh tnqynsTpki<br>61 iyvkgtiEln vddnnqpvgp EYyDdphYdf eaylKeydpK KwgkkevSgp leearArsqk<br>121 kqkEriVvNv gsntsiigvg kdakiVgggf liknvdnvii rniefeapVd Ffpewdptdg<br>181 EYgewnseyd siTieSsHhi widhntftdg dhpdKslgty fgrpfqqhdg aldi<u>s</u>nssdf<br>241 itisynvfKD hdkvSligSs dsrKTdEghl Kvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 14 | 1 kelghDvlkp NdgwaSygeg ttggSEaspD nvYTvtnKSe lVqalggnnh tnqynsTpki<br>61 iyvkgtiEln vddnnqpvgp EYyDdphYdf eaylKeydpK KwgkkevSgp leearArsqk<br>121 kqkEriVvNv gsntsiigvg kdakiVgggf liknvdnvii rniefeapVd Ffpewdptdg<br>181 EYgewnseyd siTieSsHhi widhntftdg dhpdKslgty fgrpfqqhdg aldi<u>n</u>nssdf<br>241 itisynvfKD hdkvSligSs dsrKTdEghl Kvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 15 | 1 kelghDvlkp NdgwaSygeg ttggSEaspD nvYTvtnKSe lVqalggnnh tnqynsTpki<br>61 iyvkgtiEln vddnnqpvgp EYyDdphYdf eaylKeydpK KwgkkevSgp leearArsqk<br>121 kqkEriVvNv gsntsiigvg kdakiVgggf liknvdnvii rniefeapVd Ffpewdptdg<br>181 EYgewnseyd siTieSsHhi widhntftdg dhpdKslgty fgrpfqqhdg aldi<u>c</u>nssdf<br>241 itisynvfKD hdkvSligSs dsrKTdEghl Kvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 16 | aaagaactgg gtcatgaagt tctgaaaccg tatgatggtt gggcagcgta tggtgaaggt 60<br>acaaccggtg gtgcaatggc aagtccgcag aatgtttttg ttgttaccaa tcgtaccgaa 120<br>ctgattcagg cactgggtgg taataatcat accaatcagt ataattccgt gccgaaaatc 180<br>atctatgtga aaggcaccat tgatctgaac gtggatgata ataatcagcc ggttggtccg 240<br>gatttctata agatccgca ttttgatttt gaggcctatc tgcgtgaata tgatccggca 300<br>acctggggta aaaagaagt tgaaggtccg ctggaagaag cacgcgttcg tagccagaaa 360<br>aaacagaaag atcgtatcat ggtttatgtg ggtagcaaca ccagcattat tggtgttggt 420<br>aaagacgcga aaatcaaagg tggtggtttc ctgattaaaa acgtggataa tgtgatcatc 480<br>cgcaacatcg aatttgaagc accgctggat tattttccgg aatgggatcc gaccgatggc 540<br>accctgggtg aatggaatag cgaatatgat agcattagca ttgaaggcag cagccatatt 600<br>tggattgatc acaatacctt taccgatggc gatcatccgg atagcct gggcacctat 660<br>tttggtcgtc cgtttcagca gcatgatggc gcactggata tcaaaaatag cagcgatttt 720<br>atcaccatca gctacaacgt gtttaccaac cacgataaag ttaccctgat ggtgcaagc 780<br>gatagccgta tggcagatag cggtcatctg cgtgttaccc tgcatcacaa ttattacaaa 840<br>aatgttaccc agcgtctgcc tcgtgttcgt tttggtcagg ttcatatcta taacaactac 900<br>tatgagttta gcaacctggc cgattatgat tttcagtatg catgggggtgt tggtgtgttt 960<br>agccagattt atgcacagaa caactatttc agcttcgatt gggatattga tccgagcctg 1020<br>attatcaaag tttggagcaa aaatgaagaa agcatgtatg aaaccggcac catcgttgat 1080<br>ctgccgaatg gtcgtcgtta tattgatctg gttgcaagct ataatgaaag caataccctg 1140<br>cagctgaaaa aagaggttac ctggaaaccg atgttctatc atgttattca tccgaccccg 1200<br>agcgttccgg cactggttaa agcaaaagcc ggtgcaggta atctgcat 1248 |
| 17 | aaagaactgg gtcatgaagt tctgaaaccg tatgatggtt gggcagcgta tggtgaaggt 60<br>acaaccggtg gtgcaatggc aagtccgcag aatgtttttg ttgttaccaa tcgtaccgaa 120<br>ctgattcagg cactgggtgg taataatcat accaatcagt ataattccgt gccgaaaatc 180<br>atctatgtga aaggcaccat tgatctgaac gtggatgata ataatcagcc ggttggtccg 240<br>gatttctata agatccgca ttttgatttt gaggcctatc tgcgtgaata tgatccggca 300<br>acctggggta aaaagaagt tgaaggtccg ctggaagaag cacgcgttcg tagccagaaa 360 |

TABLE 8-continued

Amino acid and nucleotide sequences disclosed herein.

| SEQ ID NO: | Sequence | |
|---|---|---|

|  | aaacagaaag atcgtatcat ggtttatgtg ggtagcaaca ccagcattat tggtgttggt | 420 |
|  | aaagacgcga aaatcaaagg tggtggtttc ctgattaaaa acgtggataa tgtgatcatc | 480 |
|  | cgcaacatcg aatttgaagc accgctggat tattttccgg aatgggatcc gaccgatggc | 540 |
|  | accctgggtg aatggaatag cgaatatgat agcattagca ttgaaggcag cagccatatt | 600 |
|  | tggattgatc acaataccct taccgatggc gatcatccgg atcgtagcct gggcacctat | 660 |
|  | tttggtcgtc cgtttcagca gcatgatggc gcactggata tcaccaatag cagcgatttt | 720 |
|  | atcaccatca gctacaacgt gtttaccaac cacgataaag ttaccctgat tggtgcaagc | 780 |
|  | gatagccgta tggcagatag cggtcatctg cgtgttaccc tgcatcacaa ttattacaaa | 840 |
|  | aatgttaccc agcgtctgcc tcgtgttcgt tttggtcagg ttcatatcta taacaactac | 900 |
|  | tatgagttta gcaacctggc cgattatgat tttcagtatg catgggggtgt tggtgtgttt | 960 |
|  | agccagattt atgcacagaa caactatttc agcttcgatt gggatattga tccgagcctg | 1020 |
|  | attatcaaag tttggagcaa aaatgaagaa agcatgtatg aaaccggcac catcgttgat | 1080 |
|  | ctgccgaatg gtcgtcgtta tattgatctg gttgcaagct ataatgaaag caataccctg | 1140 |
|  | cagctgaaaa aagaggttac ctggaaaccg atgttctatc atgttattca tccgaccccg | 1200 |
|  | agcgttccgg cactggttaa agcaaaagcc ggtgcaggta atctgcat | 1248 |
| 18 | aaagaactgg gtcatgaagt tctgaaaccg tatgatggtt gggcagcgta tggtgaaggt | 60 |
|  | acaaccggtg gtgcaatggc aagtccgcag aatgttttg ttgttaccaa tcgtaccgaa | 120 |
|  | ctgattcagg cactgggtgg taataatcat accaatcagt ataattccgt gccgaaaatc | 180 |
|  | atctatgtga aaggcaccat tgatctgaac gtggatgata taatcagcc ggttggtccg | 240 |
|  | gatttctata agatccgca ttttgatttt gaggcctatc tgcgtgaata tgatccggca | 300 |
|  | acctggggta aaaagaagt tgaaggtccg ctggaagaag cacgcgttcg tagccagaaa | 360 |
|  | aaacagaaag atcgtatcat ggtttatgtg ggtagcaaca ccagcattat tggtgttggt | 420 |
|  | aaagacgcga aaatcaaagg tggtggtttc ctgattaaaa acgtggataa tgtgatcatc | 480 |
|  | cgcaacatcg aatttgaagc accgctggat tattttccgg aatgggatcc gaccgatggc | 540 |
|  | accctgggtg aatggaatag cgaatatgat agcattagca ttgaaggcag cagccatatt | 600 |
|  | tggattgatc acaataccct taccgatggc gatcatccgg atcgtagcct gggcacctat | 660 |
|  | tttggtcgtc cgtttcagca gcatgatggc gcactggata tcagcaatag cagcgatttt | 720 |
|  | atcaccatca gctacaacgt gtttaccaac cacgataaag ttaccctgat tggtgcaagc | 780 |
|  | gatagccgta tggcagatag cggtcatctg cgtgttaccc tgcatcacaa ttattacaaa | 840 |
|  | aatgttaccc agcgtctgcc tcgtgttcgt tttggtcagg ttcatatcta taacaactac | 900 |
|  | tatgagttta gcaacctggc cgattatgat tttcagtatg catgggggtgt tggtgtgttt | 960 |
|  | agccagattt atgcacagaa caactatttc agcttcgatt gggatattga tccgagcctg | 1020 |
|  | attatcaaag tttggagcaa aaatgaagaa agcatgtatg aaaccggcac catcgttgat | 1080 |
|  | ctgccgaatg gtcgtcgtta tattgatctg gttgcaagct ataatgaaag caataccctg | 1140 |
|  | cagctgaaaa aagaggttac ctggaaaccg atgttctatc atgttattca tccgaccccg | 1200 |
|  | agcgttccgg cactggttaa agcaaaagcc ggtgcaggta atctgcat | 1248 |
| 19 | aaagaactgg gtcatgaagt tctgaaaccg tatgatggtt gggcagcgta tggtgaaggt | 60 |
|  | acaaccggtg gtgcaatggc aagtccgcag aatgttttg ttgttaccaa tcgtaccgaa | 120 |
|  | ctgattcagg cactgggtgg taataatcat accaatcagt ataattccgt gccgaaaatc | 180 |
|  | atctatgtga aaggcaccat tgatctgaac gtggatgata taatcagcc ggttggtccg | 240 |
|  | gatttctata agatccgca ttttgatttt gaggcctatc tgcgtgaata tgatccggca | 300 |
|  | acctggggta aaaagaagt tgaaggtccg ctggaagaag cacgcgttcg tagccagaaa | 360 |
|  | aaacagaaag atcgtatcat ggtttatgtg ggtagcaaca ccagcattat tggtgttggt | 420 |
|  | aaagacgcga aaatcaaagg tggtggtttc ctgattaaaa acgtggataa tgtgatcatc | 480 |
|  | cgcaacatcg aatttgaagc accgctggat tattttccgg aatgggatcc gaccgatggc | 540 |
|  | accctgggtg aatggaatag cgaatatgat agcattagca ttgaaggcag cagccatatt | 600 |
|  | tggattgatc acaataccct taccgatggc gatcatccgg atcgtagcct gggcacctat | 660 |
|  | tttggtcgtc cgtttcagca gcatgatggc gcactggata tcaacaatag cagcgatttt | 720 |
|  | atcaccatca gctacaacgt gtttaccaac cacgataaag ttaccctgat tggtgcaagc | 780 |
|  | gatagccgta tggcagatag cggtcatctg cgtgttaccc tgcatcacaa ttattacaaa | 840 |
|  | aatgttaccc agcgtctgcc tcgtgttcgt tttggtcagg ttcatatcta taacaactac | 900 |
|  | tatgagttta gcaacctggc cgattatgat tttcagtatg catgggggtgt tggtgtgttt | 960 |
|  | agccagattt atgcacagaa caactatttc agcttcgatt gggatattga tccgagcctg | 1020 |
|  | attatcaaag tttggagcaa aaatgaagaa agcatgtatg aaaccggcac catcgttgat | 1080 |
|  | ctgccgaatg gtcgtcgtta tattgatctg gttgcaagct ataatgaaag caataccctg | 1140 |
|  | cagctgaaaa aagaggttac ctggaaaccg atgttctatc atgttattca tccgaccccg | 1200 |
|  | agcgttccgg cactggttaa agcaaaagcc ggtgcaggta atctgcat | 1248 |
| 20 | aaagaactgg gtcatgaagt tctgaaaccg tatgatggtt gggcagcgta tggtgaaggt | 60 |
|  | acaaccggtg gtgcaatggc aagtccgcag aatgttttg ttgttaccaa tcgtaccgaa | 120 |
|  | ctgattcagg cactgggtgg taataatcat accaatcagt ataattccgt gccgaaaatc | 180 |
|  | atctatgtga aaggcaccat tgatctgaac gtggatgata taatcagcc ggttggtccg | 240 |
|  | gatttctata agatccgca ttttgatttt gaggcctatc tgcgtgaata tgatccggca | 300 |
|  | acctggggta aaaagaagt tgaaggtccg ctggaagaag cacgcgttcg tagccagaaa | 360 |
|  | aaacagaaag atcgtatcat ggtttatgtg ggtagcaaca ccagcattat tggtgttggt | 420 |
|  | aaagacgcga aaatcaaagg tggtggtttc ctgattaaaa acgtggataa tgtgatcatc | 480 |
|  | cgcaacatcg aatttgaagc accgctggat tattttccgg aatgggatcc gaccgatggc | 540 |
|  | accctgggtg aatggaatag cgaatatgat agcattagca ttgaaggcag cagccatatt | 600 |
|  | tggattgatc acaataccct taccgatggc gatcatccgg atcgtagcct gggcacctat | 660 |
|  | tttggtcgtc cgtttcagca gcatgatggc gcactggata tctgcaatag cagcgatttt | 720 |
|  | atcaccatca gctacaacgt gtttaccaac cacgataaag ttaccctgat tggtgcaagc | 780 |
|  | gatagccgta tggcagatag cggtcatctg cgtgttaccc tgcatcacaa ttattacaaa | 840 |
|  | aatgttaccc agcgtctgcc tcgtgttcgt tttggtcagg ttcatatcta taacaactac | 900 |
|  | tatgagttta gcaacctggc cgattatgat tttcagtatg catgggggtgt tggtgtgttt | 960 |

TABLE 8-continued

Amino acid and nucleotide sequences disclosed herein.

| SEQ ID NO: | Sequence | |
|---|---|---|
| | agccagattt atgcacagaa caactatttc agcttcgatt gggatattga tccgagcctg | 1020 |
| | attatcaaag tttggagcaa aaatgaagaa agcatgtatg aaaccggcac catcgttgat | 1080 |
| | ctgccgaatg gtcgtcgtta tattgatctg gttgcaagct ataatgaaag caataccctg | 1140 |
| | cagctgaaaa aagaggttac ctggaaaccg atgttctatc atgttattca tccgaccccg | 1200 |
| | agcgttccgg cactggttaa agcaaaagcc ggtgcaggta atctgcat | 1248 |
| 21 | aaagaactgg gtcatgatgt gctgaaaccg tatgatggtt gggcaagcta tggtgaaggt | 60 |
| | acaaccggtg gtagcatggc aagtccgcag aatgtttata ccgttaccaa taaaaccgaa | 120 |
| | ctggttcagg cactgggtgg taataatcat accaatcagt ataattccgt gccgaaaatc | 180 |
| | atctatgtga aaggcaccat tgaactgaac gtggatgata ataatcagcc ggttggtccg | 240 |
| | gaattctata aagatccgca ttatgatttt gaagcctatc tgaaagagta tgatccgaaa | 300 |
| | aaatggggca aaaaagaagt tagccggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggtggat tattttccgg aatgggatcc gaccgatggc | 540 |
| | accctgggtg aatggaatag cgaatatgat agcattacca ttgaaggcag ccatcatatt | 600 |
| | tggatcgatc acaataccct taccgatggc gatcatccgg ataaaagcct gggcacctat | 660 |
| | tttggtcgtc cgtttcagca gcatgatggc gcactggata tcaccaatag cagcgatttt | 720 |
| | atcaccatca gctacaacgt gtttaaagac catgataaag tgaccctgat tggtgcaagc | 780 |
| | gatagccgta tggcagatga aggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catgggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 22 | aaagaactgg gtcatgatgt gctgaaaccg tatgatggtt gggcaagcta tggtgaaggt | 60 |
| | acaaccggtg gtagcatggc aagtccgcag aatgtttata ccgttaccaa taaaaccgaa | 120 |
| | ctggttcagg cactgggtgg taataatcat accaatcagt ataattccgt gccgaaaatc | 180 |
| | atctatgtga aaggcaccat tgaactgaac gtggatgata ataatcagcc ggttggtccg | 240 |
| | gaattctata aagatccgca ttatgatttt gaagcctatc tgaaagagta tgatccgaaa | 300 |
| | aaatggggca aaaaagaagt tagccggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggtggat tattttccgg aatgggatcc gaccgatggc | 540 |
| | accctgggtg aatggaatag cgaatatgat agcattacca ttgaaggcag ccatcatatt | 600 |
| | tggatcgatc acaataccct taccgatggc gatcatccgg ataaaagcct gggcacctat | 660 |
| | tttggtcgtc cgtttcagca gcatgatggc gcactggata tcaccaatag cagcgatttt | 720 |
| | atcaccatca gctacaacgt gtttaaagac catgataaag tgaccctgat tggtgcaagc | 780 |
| | gatagccgta tggcagatga aggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catgggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 23 | aaagaactgg gtcatgatgt gctgaaaccg tatgatggtt gggcaagcta tggtgaaggt | 60 |
| | acaaccggtg gtagcatggc aagtccgcag aatgtttata ccgttaccaa taaaaccgaa | 120 |
| | ctggttcagg cactgggtgg taataatcat accaatcagt ataattccgt gccgaaaatc | 180 |
| | atctatgtga aaggcaccat tgaactgaac gtggatgata ataatcagcc ggttggtccg | 240 |
| | gaattctata aagatccgca ttatgatttt gaagcctatc tgaaagagta tgatccgaaa | 300 |
| | aaatggggca aaaaagaagt tagccggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggtggat tattttccgg aatgggatcc gaccgatggc | 540 |
| | accctgggtg aatggaatag cgaatatgat agcattacca ttgaaggcag ccatcatatt | 600 |
| | tggatcgatc acaataccct taccgatggc gatcatccgg ataaaagcct gggcacctat | 660 |
| | tttggtcgtc cgtttcagca gcatgatggc gcactggata tcagcaatag cagcgatttt | 720 |
| | atcaccatca gctacaacgt gtttaaagac catgataaag tgaccctgat tggtgcaagc | 780 |
| | gatagccgta tggcagatga aggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catgggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 24 | aaagaactgg gtcatgatgt gctgaaaccg tatgatggtt gggcaagcta tggtgaaggt | 60 |
| | acaaccggtg gtagcatggc aagtccgcag aatgtttata ccgttaccaa taaaaccgaa | 120 |
| | ctggttcagg cactgggtgg taataatcat accaatcagt ataattccgt gccgaaaatc | 180 |
| | atctatgtga aaggcaccat tgaactgaac gtggatgata ataatcagcc ggttggtccg | 240 |

TABLE 8-continued

Amino acid and nucleotide sequences disclosed herein.

| SEQ ID NO: | Sequence | |
|---|---|---|
|  | gaattctata aagatccgca ttatgatttt gaagcctatc tgaaagagta tgatccgaaa | 300 |
|  | aaatggggca aaaagaagt tagcggtccg ctggaagaag cacgcgcacg tagccagaaa | 360 |
|  | aaacagaaag aacgtattgt tgtgaatgtg ggtagcaaca ccagcattat tggtgttggt | 420 |
|  | aaagatgcca aaattgtggg tggtggtttc ctgattaaaa acgtggataa tgtgatcatc | 480 |
|  | cgcaacatcg aatttgaagc accggtggat tattttccgg aatgggatcc gaccgatggc | 540 |
|  | accctgggtg aatggaatag cgaatatgat agcattacca ttgaaggcag ccatcatatt | 600 |
|  | tggatcgatc acaataccttt taccgatggc gatcatccgg ataaaagcct gggcacctat | 660 |
|  | tttggtcgtc cgtttcagca gcatgatggc gcactggata tcaacaatag cagcgatttt | 720 |
|  | atcaccatca gctacaacgt gtttaaagac catgataaag tgaccctgat tggtgcaagc | 780 |
|  | gatagccgta tggcagatga aggtcatctg cgtgttaccc tgcatcacaa ttattacaaa | 840 |
|  | aatgttaccc agcgtctgcc tcgtgttcgt tttggtcagg ttcatatcta taacaactac | 900 |
|  | tatgagttta gcaacctggc cgattatgac tttcagtatg catgggggtgt tggtgttgga | 960 |
|  | agcaaaatct atgcccagaa caactatttc agcttcgatt gggatattga cccgagcaaa | 1020 |
|  | attatcaaag tttggagcaa aaacgaagaa agcatgtatg aaagcggtac gattgttgat | 1080 |
|  | ctgccgaatg gtcgtcgtta tattgatctg gttgcaagct ataatgaaag caataccctg | 1140 |
|  | cagctgaaaa aagaggttgg ttggaaaccg atgttctatc atgttattca tccgaccccg | 1200 |
|  | agcgttccgg cactggttaa agcaaaagcc ggtgcaggta atctgcat | 1248 |
| 25 | aaagaactgg gtcatgatgt gctgaaaccg tatgatggtt gggcaagcta tggtgaaggt | 60 |
|  | acaaccggtg gtagcatggc aagtccgcag aatgtttata ccgttaccaa taaaaccgaa | 120 |
|  | ctggttcagg cactgggtgg taataatcat accaatcagt ataattccgt gccgaaaatc | 180 |
|  | atctatgtga aaggcaccat tgaactgaac gtggatgata taatcagcc ggttggtccg | 240 |
|  | gaattctata aagatccgca ttatgatttt gaagcctatc tgaaagagta tgatccgaaa | 300 |
|  | aaatggggca aaaagaagt tagcggtccg ctggaagaag cacgcgcacg tagccagaaa | 360 |
|  | aaacagaaag aacgtattgt tgtgaatgtg ggtagcaaca ccagcattat tggtgttggt | 420 |
|  | aaagatgcca aaattgtggg tggtggtttc ctgattaaaa acgtggataa tgtgatcatc | 480 |
|  | cgcaacatcg aatttgaagc accggtggat tattttccgg aatgggatcc gaccgatggc | 540 |
|  | accctgggtg aatggaatag cgaatatgat agcattacca ttgaaggcag ccatcatatt | 600 |
|  | tggatcgatc acaataccttt taccgatggc gatcatccgg ataaaagcct gggcacctat | 660 |
|  | tttggtcgtc cgtttcagca gcatgatggc gcactggata tctgcaatag cagcgatttt | 720 |
|  | atcaccatca gctacaacgt gtttaaagac catgataaag tgaccctgat tggtgcaagc | 780 |
|  | gatagccgta tggcagatga aggtcatctg cgtgttaccc tgcatcacaa ttattacaaa | 840 |
|  | aatgttaccc agcgtctgcc tcgtgttcgt tttggtcagg ttcatatcta taacaactac | 900 |
|  | tatgagttta gcaacctggc cgattatgac tttcagtatg catgggggtgt tggtgttgaa | 960 |
|  | agcaaaatct atgcccagaa caactatttc agcttcgatt gggatattga cccgagcaaa | 1020 |
|  | attatcaaag tttggagcaa aaacgaagaa agcatgtatg aaagcggtac gattgttgat | 1080 |
|  | ctgccgaatg gtcgtcgtta tattgatctg gttgcaagct ataatgaaag caataccctg | 1140 |
|  | cagctgaaaa aagaggttgg ttggaaaccg atgttctatc atgttattca tccgaccccg | 1200 |
|  | agcgttccgg cactggttaa agcaaaagcc ggtgcaggta atctgcat | 1248 |
| 26 | aaagaactgg gtcatgatgt gctgaaaccg aatgatggtt gggcaagcta tggtgaaggt | 60 |
|  | acaaccggtg gtagcgaagc aagtccggat aatgtttata ccgttaccaa taaaagcgaa | 120 |
|  | ctggttcagg cactgggtgg taataatcat accaatcagt ataattccac cccgaaaatc | 180 |
|  | atctatgtga aaggcaccat tgaactgaac gtggatgata taatcagcc ggttggtccg | 240 |
|  | gaatattatg atgatccgca ttatgatttt gaagcctatc tgaaagagta tgatccgaaa | 300 |
|  | aaatggggca aaaagaagt tagcggtccg ctggaagaag cacgcgcacg tagccagaaa | 360 |
|  | aaacagaaag aacgtattgt tgtgaatgtg ggtagcaaca ccagcattat tggtgttggt | 420 |
|  | aaagatgcca aaattgtggg tggtggtttc ctgattaaaa acgtggataa tgtgatcatc | 480 |
|  | cgcaacatcg aatttgaagc accggttgat tttttccgg aatgggatcc gaccgatggt | 540 |
|  | gaatatggcg aatggaatag cgaatatgat agcattacca tcgaaagcag ccatcatatt | 600 |
|  | tggatcgatc acaataccttt taccgatggc gatcatccgg ataaaagcct gggcacctat | 660 |
|  | tttggtcgtc cgtttcagca gcatgatggc gcactggata tcaaaaatag cagcgatttt | 720 |
|  | atcaccatca gctacaacgt gtttaaagac catgataaag tgagcctgat tggttcaagc | 780 |
|  | gatagccgta aaaccgatga aggtcatctg aaagttaccc tgcatcacaa ctattacaaa | 840 |
|  | aatgttaccc agcgtctgcc tcgtgttcgt tttggtcagg ttcatatcta taacaactac | 900 |
|  | tatgagttta gcaacctggc cgattatgac tttcagtatg catgggggtgt tggtgttgaa | 960 |
|  | agcaaaatct atgcccagaa caactatttc agcttcgatt gggatattga cccgagcaaa | 1020 |
|  | attatcaaag tttggagcaa aaacgaagaa agcatgtatg aaagcggtac gattgttgat | 1080 |
|  | ctgccgaatg gtcgtcgtta tattgatctg gttgcaagct ataatgaaag caataccctg | 1140 |
|  | cagctgaaaa aagaggttgg ttggaaaccg atgttctatc atgttattca tccgaccccg | 1200 |
|  | agcgttccgg cactggttaa agcaaaagcc ggtgcaggta atctgcat | 1248 |
| 27 | aaagaactgg gtcatgatgt gctgaaaccg aatgatggtt gggcaagcta tggtgaaggt | 60 |
|  | acaaccggtg gtagcgaagc aagtccggat aatgtttata ccgttaccaa taaaagcgaa | 120 |
|  | ctggttcagg cactgggtgg taataatcat accaatcagt ataattccac cccgaaaatc | 180 |
|  | atctatgtga aaggcaccat tgaactgaac gtggatgata taatcagcc ggttggtccg | 240 |
|  | gaatattatg atgatccgca ttatgatttt gaagcctatc tgaaagagta tgatccgaaa | 300 |
|  | aaatggggca aaaagaagt tagcggtccg ctggaagaag cacgcgcacg tagccagaaa | 360 |
|  | aaacagaaag aacgtattgt tgtgaatgtg ggtagcaaca ccagcattat tggtgttggt | 420 |
|  | aaagatgcca aaattgtggg tggtggtttc ctgattaaaa acgtggataa tgtgatcatc | 480 |
|  | cgcaacatcg aatttgaagc accggttgat tttttccgg aatgggatcc gaccgatggt | 540 |
|  | gaatatggcg aatggaatag cgaatatgat agcattacca tcgaaagcag ccatcatatt | 600 |
|  | tggatcgatc acaataccttt taccgatggc gatcatccgg ataaaagcct gggcacctat | 660 |
|  | tttggtcgtc cgtttcagca gcatgatggc gcactggata tcaccaatag cagcgatttt | 720 |
|  | atcaccatca gctacaacgt gtttaaagac catgataaag tgagcctgat tggttcaagc | 780 |
|  | gatagccgta aaaccgatga aggtcatctg aaagttaccc tgcatcacaa ctattacaaa | 840 |

TABLE 8-continued

Amino acid and nucleotide sequences disclosed herein.

| SEQ ID NO: | Sequence | |
|---|---|---|
| | aatgttaccc agcgtctgcc tcgtgttcgt tttggtcagg ttcatatcta taacaactac | 900 |
| | tatgagttta gcaacctggc cgattatgac tttcagtatg catggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 28 | aaagaactgg gtcatgatgt gctgaaaccg aatgatggtt gggcaagcta tggtgaaggt | 60 |
| | acaaccggtg gtagcgaagc aagtccggat aatgtttata ccgttaccaa taaaagcgaa | 120 |
| | ctggttcagg cactgggtgg taataatcat accaatcagt ataattccac cccgaaaatc | 180 |
| | atctatgtga aaggcaccat tgaactgaac gtggatgata ataatcagcc ggttggtccg | 240 |
| | gaatattatg atgatccgca ttatgatttt gaagcctatc tgaaagagta tgatccgaaa | 300 |
| | aaatggggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggttgat ttttttccgg aatgggatcc gaccgatggt | 540 |
| | gaatatggcg aatggaatag cgaatatgat agcattacca tcgaaagcag ccatcatatt | 600 |
| | tggatcgatc acaataccttc taccgatggc gatcatccgg ataaaagcct gggcacctat | 660 |
| | tttggtcgtc cgtttcagca gcatgatggc gcactggata tcagcaatag cagcgatttt | 720 |
| | atcaccatca gctacaacgt gtttaaagac catgataaag tgagcctgat tggttcaagc | 780 |
| | gatagccgta aaaccgatga aggtcatctg aaagttaccc tgcatcacaa ctattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 29 | aaagaactgg gtcatgatgt gctgaaaccg aatgatggtt gggcaagcta tggtgaaggt | 60 |
| | acaaccggtg gtagcgaagc aagtccggat aatgtttata ccgttaccaa taaaagcgaa | 120 |
| | ctggttcagg cactgggtgg taataatcat accaatcagt ataattccac cccgaaaatc | 180 |
| | atctatgtga aaggcaccat tgaactgaac gtggatgata ataatcagcc ggttggtccg | 240 |
| | gaatattatg atgatccgca ttatgatttt gaagcctatc tgaaagagta tgatccgaaa | 300 |
| | aaatggggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggttgat ttttttccgg aatgggatcc gaccgatggt | 540 |
| | gaatatggcg aatggaatag cgaatatgat agcattacca tcgaaagcag ccatcatatt | 600 |
| | tggatcgatc acaataccttc taccgatggc gatcatccgg ataaaagcct gggcacctat | 660 |
| | tttggtcgtc cgtttcagca gcatgatggc gcactggata tcaacaatag cagcgattttt | 720 |
| | atcaccatca gctacaacgt gtttaaagac catgataaag tgagcctgat tggttcaagc | 780 |
| | gatagccgta aaaccgatga aggtcatctg aaagttaccc tgcatcacaa ctattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 30 | aaagaactgg gtcatgatgt gctgaaaccg aatgatggtt gggcaagcta tggtgaaggt | 60 |
| | acaaccggtg gtagcgaagc aagtccggat aatgtttata ccgttaccaa taaaagcgaa | 120 |
| | ctggttcagg cactgggtgg taataatcat accaatcagt ataattccac cccgaaaatc | 180 |
| | atctatgtga aaggcaccat tgaactgaac gtggatgata ataatcagcc ggttggtccg | 240 |
| | gaatattatg atgatccgca ttatgatttt gaagcctatc tgaaagagta tgatccgaaa | 300 |
| | aaatggggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggttgat ttttttccgg aatgggatcc gaccgatggt | 540 |
| | gaatatggcg aatggaatag cgaatatgat agcattacca tcgaaagcag ccatcatatt | 600 |
| | tggatcgatc acaataccttc taccgatggc gatcatccgg ataaaagcct gggcacctat | 660 |
| | tttggtcgtc cgtttcagca gcatgatggc gcactggata tctgcaatag cagcgatttt | 720 |
| | atcaccatca gctacaacgt gtttaaagac catgataaag tgagcctgat tggttcaagc | 780 |
| | gatagccgta aaaccgatga aggtcatctg aaagttaccc tgcatcacaa ctattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |

TABLE 8-continued

Amino acid and nucleotide sequences disclosed herein.

| SEQ ID NO: | Sequence |
|---|---|
| 31 | GAAATTAATACGACTCACTATAGG |
| 32 | GGTTATGCTAGTTATTGCTCAGCGGTG |
| 33 | GCTGATGGTGATAAAATCGCTGCTATTggTGATATCCAG |
| 34 | GCTGATGGTGATAAAATCGCTGCTATTgcTGATATCCAG |
| 35 | GCTGATGGTGATAAAATCGCTGCTATTgTTGATATCCAG |
| 36 | GCTGATGGTGATAAAATCGCTGCTATTgcaGATATCCAG |
| 37 | AATAGCAGCGATTTTATCACCATCAGCTACAACGTGTTTA |
| 38 | GCCATCATGCTGCTGAAACGGACGACCAAAATAGGTG |
| 39 | GGTCGTCCGTTTCAGCAGCATGATGGCctgCTGGATATCA |
| 40 | ```
  1 kelghevlkp ydgwaaygeg ttggamaspq nvfvvtnrte liqalggnnh tnqynsvpki
 61 iyvkgtidln vddnnqpvgp dfykdphfdf eaylreydpa twgkkevegp leearvrsqk
121 kqkdrimvyv gsntsiigvg kdakikgggf liknvdnvii rniefeapld yfpewdptdg
181 tlgewnseyd sisiegsshi widhntftdg dhpdrslgty fgrpfqqhdg llditnssdf
241 itisynvftn hdkvtligas dsrmadsghl rvtlhhnyyk nvtqrlprvr fgqvhiynny
301 yefsnladyd fqyawgvgvf sqiyaqnnyf sfdwdidpsl iikvwsknee smyetgtivd
361 lpngrryidl vasynesntl qlkkevtwkp mfyhvihptp svpalvkaka gagnlh
``` |
| 41 | ```
  1 kelghevlpk ydgawwygeg ttggamaspq nvfvvtnrte liqalggnnh tnqynsvpki
 61 iyvkgtidln vddnnqpvgp dfykdphfdf eaylreydpa twgkkevegp leearvrsqk
121 kqkdrimvyv gsntsiigvg kdakikgggf liknvdnvii rniefeapld yfpewdptdg
181 tlgewnseyd sisiegsshi widhntftdg dhpdrslgyt fgrpfqqhdg lldisnssdf
241 itisynvftn hdkvtligas dsrmadsghl rvtlhhnyyk nvtqrlprvr fgqvhiynny
301 yefsnladyd fqyawgvgvf sqiyaqnnyf sfdwdidpsl iikvwsknee smyetgtivd
361 lpngrryidl vasynesntl qlkkevtwkp mfyhvihptp svpalvkaka gagnlh
``` |
| 42 | ```
  1 kelghDvlkp ydgwaSygeg ttggSmaspq nvYTvtnKte lVqalggnnh tnqynsvpki
 61 iyvkgtiEln vddnnqpvgp EfykdphYdf eaylKeydpK KwgkkevSgp leearArsqk
121 kqkEriVvNv gsntsiigvg kdakiVgggf liknvdnvii rniefeapVd yfpewdptdg
181 tlgewnseyd siTiegsHhi widhntftdf dhpdKslgty fgrpfqqhdg lldinnssdf
241 itisynvfKD hdkvtligas dsrmadEghl rvtlhhnyyk nvtqrlprvr fgqvhiynny
301 yefsnladyd fqyawgvgvE sKiyaqnnyf sfdwdidpsK iikvwsknee smyeSgtivd
361 lpngrryidl vasynesntl qlkkevGwkp mfyhvihptp svpalvkaka gagnlh
``` |
| 43 | ```
  1 kelghDvlkp NdgwaSygeg ttggSEaspD nvYTvtnKSe lVqalggnnh tnqynsTpki
 61 iyvkgtiEln vddnnqpvgp EYykDdphYdf eaylKeydpK KwgkkevSgp leearArsqk
121 kqkEriVvNv gsntsiigvg kdakiVgggf liknvdnvii rniefeapVd Ffpewdptdg
181 EYgewnseyd siTieSsHhi widhntftdf dhpdKslgty fgrpfqqhdg lldicnssdf
241 itisynvfKD hdkvSligSs dsrKTdEghl Kvtlhhnyyk nvtqrlprvr fgqvhiynny
301 yefsnladyd fqyawgvgvE sKiyaqnnyf sfdwdidpsK iikvwsknee smyeSgtivd
361 lpngrryidl vasynesntl qlkkevGwkp mfyhvihptp svpalvkaka gagnlh
``` |
| 44 | ```
aaagaactgg gtcatgaagt tctgaaaccg tatgatggtt gggcagcgta tggtgaaggt   60
acaaccggtg gtgcaatggc aagtccgcag aatgttttg ttgttaccaa tcgtaccgaa  120
ctgattcagg cactgggtgg taataatcat accagtcagt ataattccgt gccgaaaatc  180
atctatgtga aaggcaccat tgatctgaac gtggatgata taatcagcc ggttggtccg  240
gatttctata aagatccgca ttttgatttt gaggcctatc tgcgtgaata tgatccggca  300
acctggggta aaaagaagt tgaaggtccg ctggaagaag cacgcgttcg tagccagaaa  360
aaacagaaag atcgtatcat ggtttatgtg ggtagcaaca ccagcattat tggtgttggt  420
aaagacgcga aaatcaaagg tggtggttc ctgattaaaa acgtggataa tgtgatcatc  480
cgcaacatcg aatttgaagc accgctggat tatttccgg gggaattgc gaccgatggc  540
accctgggtg aatggaatag cgaatatgat agcattagca ttgaaggcag cagccatatt  600
tggattgatc acaataccct taccgatggc gatcatccgg atcgtagcct gggcacctat  660
tttggtcgtc cgtttcagca gcatgatggc ctgctggata tcaccaatag cagcgatttt  720
atcaccatca gctacaacgt gtttaccaac cacgataaag ttaccctgat tggtgcaagc  780
gataccgta tgcagatag cggtcatctg cgtgttaccc tgcatcacaa ttattacaaa  840
aatgttaccc agcgtctgcc tcgtgttcgt tttggtcagg ttcatatcta taacaactac  900
tatgagttta gcaacctggc cgattatgat ttcagtatg catggggtgt ggtgtgttt  960
agccagatt atgcacagaa caactatttc agcttcgatt gggatattga tccgagcctg 1020
attatcaaag tttggagcaa aaatgaagaa agcatgtatg aaaccggcac catcgttgat 1080
ctgccgaatg gtcgtcgtta tattgatctg gttgcaagct ataatgaaaa caatccctg 1140
cagctgaaaa aagaggttac ctggaaaccg atgttctatc atgttattca tccgacccg 1200
agcgttccgg cactggttaa agcaaaagcc ggtgcaggta atctgcat              1248
``` |
| 45 | ```
aaagaactgg gtcatgaagt tctgaaaccg tatgatggtt gggcagcgta tggtgaaggt   60
acaaccggtg gtgcaatggc aagtccgcag aatgttttg ttgttaccaa tcgtaccgaa  120
ctgattcagg cactgggtgg taataatcat accaatcagt ataattccgt gccgaaaatc  180
atctatgtga aaggcaccat tgatctgaac gtggatgata taatcagcc ggttggtccg  240
``` |

TABLE 8-continued

Amino acid and nucleotide sequences disclosed herein.

| SEQ ID NO: | Sequence | |
|---|---|---|
| | gatttctata aagatccgca ttttgatttt gaggcctatc tgcgtgaata tgatccggca | 300 |
| | acctggggta aaaaagaagt tgaaggtccg ctggaagaag cacgcgttcg tagccagaaa | 360 |
| | aaacagaaag atcgtatcat ggtttatgtg ggtagcaaca ccagcattat tggtgttggt | 420 |
| | aaagacgcga aaatcaaagg tggtggtttc ctgattaaaa acgtggataa tgtgatcatc | 480 |
| | cgcaacatcg aatttgaagc accgctggat tattttccgg aatgggatcc gaccgatggc | 540 |
| | accctgggtg aatggaatag cgaatatgat agcattagca ttgaaggcag cagccatatt | 600 |
| | tggattgatc acaataccct taccgatggc gatcatccgg atcgtagcct gggcacctat | 660 |
| | tttggtcgtc cgtttcagca gcatgatggc ctgctggata tcagcaatag cagcgatttt | 720 |
| | atcaccatca gctacaacgt gtttaccaac cacgataaag ttaccctgat tggtgcaagc | 780 |
| | gatagccgta tggcagatag cggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgat tttcagtatg catgggggtgt tggtgtgttt | 960 |
| | agccagattt atgcacagaa caactatttc agcttcgatt gggatattga tccgagcctg | 1020 |
| | attatcaaag tttggagcaa aaatgaagaa agcatgtatg aaaccggcac catcgttgat | 1080 |
| | ctgccgaatg gtcgtcgtta tattgatctg gttgcaagct ataatgaaag caatacccctg | 1140 |
| | cagctgaaaa aagaggttac ctggaaaccg atgttctatc atgttattca tccgaccccg | 1200 |
| | agcgttccgg cactggttaa agcaaaagcc ggtgcaggta atctgcat | 1248 |
| 46 | aaagaactgg gtcatgatgt gctgaaaccg tatgatggtt gggcaagcta tggtgaaggt | 60 |
| | acaaccggtg gtagcatggc aagtccgcag aatgtttata ccgttaccaa taaaaccgaa | 120 |
| | ctggttcagg cactgggtgg taataatcat accaatcagt ataattccgt gccgaaaatc | 180 |
| | atctatgtga aaggcaccat tgaactgaac gtggataata taatcagcc ggttggtccg | 240 |
| | gaattctata aagatccgca ttatgatttt gaagcctatc tgaaagagta tgatccgaaa | 300 |
| | aaatggggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggtggat tattttccgg aatgggatcc gaccgatggc | 540 |
| | accctgggtg aatggaatag cgaatatgat agcattacca ttgaaggcag ccatcatatt | 600 |
| | tggatcgatc acaataccct taccgatggc gatcatccgg ataaaagcct gggcacctat | 660 |
| | tttggtcgtc cgtttcagca gcatgatggc ctgctggata tcaacaatag cagcgatttt | 720 |
| | atcaccatca gctacaacgt gtttaaagac catgataaag tgaccctgat tggtgcaagc | 780 |
| | gatagccgta tggcagatga aggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgat tttcagtatg catgggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caatacccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 47 | aaagaactgg gtcatgatgt gctgaaaccg aatgatggtt gggcaagcta tggtgaaggt | 60 |
| | acaaccggtg gtagcgaagc aagtccggat aatgtttata ccgttaccaa taaaagcgaa | 120 |
| | ctggttcagg cactgggtgg taataatcat accaatcagt ataattccac cccgaaaatc | 180 |
| | atctatgtga aaggcaccat tgaactgaac gtggataata taatcagcc ggttggtccg | 240 |
| | gaatattatg atgatccgca ttatgatttt gaagcctatc tgaaagagta tgatccgaaa | 300 |
| | aaatggggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggttgat ttttttccgg aatgggatcc gaccgatggc | 540 |
| | gaatatgcg aatggaatag cgaatatgat agcattacca tcgaaagcag ccatcatatt | 600 |
| | tggatcgatc acaataccct taccgatggc gatcatccgg ataaaagcct gggcacctat | 660 |
| | tttggtcgtc cgtttcagca gcatgatggc ctgctggata tctgcaatag cagcgatttt | 720 |
| | atcaccatca gctacaacgt gtttaaagac catgataaag tgagcctgat tggttcaagc | 780 |
| | gatagccgta aaccgatga aggtcatctg aaagttaccc tgcatcacaa ctattacaaa | 840 |
| | aatgttaccc agcgtctgcc tcgtgttcgt tttggtcagg ttcatatcta taacaactac | 900 |
| | tatgagttta gcaacctggc cgattatgat tttcagtatg catgggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caatacccctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 48 | 1 kelghevlkp ydgwaaygeg ttggamaspq nvfvvtnrte liqalggnnh tnqynsvpki | |
| | 61 iyvkgtidln vddnnqpvgp ifykdphfdf eaylreydpa twgkkevegp leearvrsqk | |
| | 121 kqkdrimvyv gsntsiigvg kdakikgggf liknvdnvii rniefeapld yfpewdptdg | |
| | 181 tlgewnseyd sisiegsshi widhntftdg dhpdrslgty fgrpfqqhdg lldiknssdf | |
| | 241 itisynvftn hdkvtligas dsrmadsghl rvtlhhnyyk nvtqrlprvr fgqvhiynny | |
| | 301 yefsnladyd fqyawgvgvf sqiyaqnnyf sfdwdidpsl iikvwsknee smyetgtivd | |
| | 361 lpngrryidl vasynesntl qlkkevtwkp mfyhvihptp svpalvkaka gagnlh | |

TABLE 8-continued

Amino acid and nucleotide sequences disclosed herein.

| SEQ ID NO: | Sequence |
|---|---|
| 49 | ```
  1 kelghDvlkp ydgwaSygeg ttggSmaspq nvYTvtnKte lVqalggnnh tnqynsvpki
 61 iyvkgtiEln vddnnqpvgp EfykdphYdf eaylKeydpK KwgkkevSgp leearArsqk
121 kqkEriVvNv gsntsiigvg kdakiVgggf liknvdnvii rniefeapVd yfpewdptdg
181 tlgewnseyd siTiegsHhi widhntftdf dhpdKslgty fgrpfqqhdg lldiknssdf
241 itisynvfKD hdkvtligas dsrmadEghl rvtlhhnyyk nvtqrlprvr fgqvhiynny
301 yefsnladyd fqyawgvgvE sKiyqannyf sfdwdidpsK iikvswknee smyeSgtivd
361 lpngrryidl vasynesntl qlkkevGwkp mfyhvihptp svpalvkaka gagnlh
``` |
| 50 | ```
  1 kelghDvlkp NdgwaSygeg ttggSEaspD nvYTvtnKSe lVqalggnnh tnqynsTpki
 61 iyvkgtiEln vddnnqpvgp EYyDdphYdf eaylKeydpK KwgkkevSgp leearArsqk
121 kqkEriVvNv gsntsiigvg kdakiVgggf liknvdnvii rniefeapVd Ffpewdptdg
181 EYgewnseyd siTiesSshhi widhntftdf dhpdKslgty fgrpfqqhdg lldiknssdf
241 itisynvfKD hdkvSligSs dsrKTdEghl Kvtlhhnyyk nvtqrlprvr fgqvhiynny
301 yefsnladyd fqyawgvgvE sKiyqannyf sfdwdidpsK iikvswknee smyeSgtivd
361 lpngrryidl vasynesntl qlkkevGwkp mfyhvihptp svpalvkaka gagnlh
``` |
| 51 | ```
aaagaactgg gtcatgaagt tctgaaaccg tatgatggtt gggcagcgta tggtgaaggt   60
acaaccggtg gtgcaatggc aagtccgcag aatgttttg ttgttaccaa tcgtaccgaa  120
ctgattcagg cactgggtgg taataatcat accaatcagt ataattccgt gccgaaaatc  180
atctatgtga aaggcaccat tgatctgaac gtggatgata taatcagcc ggttggtccg  240
gatttctata aagatccgca ttttgatttt gaggcctatc tgcgtgaata tgatccggca  300
acctggggta aaaaagaagt tgaaggtccg ctggaagaag cacgcgttcg tagccagaaa  360
aaacagaaag atcgtatcat ggtttatgtg ggtagcaaca ccagcattat tggtgttggt  420
aaagacgcga aaatcaaagg tggtggtttc ctgattaaaa acgtggataa tgtgatcatc  480
cgcaacatcg aatttgaagc accgctggat tattttccgg aatgggatcc gaccgatggc  540
accctgggtg aatggaatag cgaatatgat agcattagca ttgaaggcag cagccatatt  600
tggattgatc acaataccct taccgatggc gatcatccgg atcgtagcct gggcacctat  660
tttggtcgtc cgtttcagca gcatgatggc gcactggata tcaaaaatag cagcgatttt  720
atcaccatca gctacaacgt gtttaccaac cacgataaag ttaccctgat tggtgcaagc  780
gatagccgta tggcagatag cggtcatctg cgtgttaccc tgcatcacaa ttattacaaa  840
aatgttaccc agcgtctgcc tcgtgttcgt tttggtcagg ttcatatcta taacaactac  900
tatgagttta gcaacctggc cgattatgat tttcagtatg catggggtgt tggtgtgttt  960
agccagattt atgcacagaa caactatttc agcttcgatt gggatattga tccgagcctg 1020
attatcaaag tttggagcaa aaatgaagaa agcatgttga aaccggcac catcgttgat 1080
ctgccgaatg gtcgtcgtta tattgatctg gttcaagct ataatgaaag caatacctg 1140
cagctgaaaa agaggttac ctggaaaccg atgttctatc atgttattca tccgaccccg 1200
agcgttccgg cactggttaa agcaaaagcc ggtgcaggta atctgcat            1248
``` |
| 52 | ```
aaagaactgg gtcatgatgt gctgaaaccg tatgatggtt gggcaagcta tggtgaaggt   60
acaaccggtg gtagcatggc aagtccgcag aatgttata ccgttaccaa taaaaccgaa  120
ctggttcagg cactgggtgg taataatcat accaatcagt ataattccgt gccgaaaatc  180
atctatgtga aaggcaccat tgaactgaac gtggatgata taatcagcc ggttggtccg  240
gaattctata aagatccgca ttatgatttt gaagcctatc tgaaagagta tgatccgaaa  300
aaatgggggca aaaaagaagt tagcggtccg ctggaagaag cacgcgcacg tagccagaaa  360
aaacagaaag aacgtattgt tgtgaatgtg ggtagcaaca ccagcattat tggtgttggt  420
aaagatgcca aaattgtggg tggtggtttc ctgattaaaa acgtggataa tgtgatcatc  480
cgcaacatcg aatttgaagc accggtggat tattttccgg aatgggatcc gaccgatggc  540
accctgggtg aatggaatag cgaatatgat agcattacca ttgaaggcag ccatcatatt  600
tggatcgatc acaataccct taccgatggc gatcatccgg ataaaagcct gggcacctat  660
tttggtcgtc cgtttcagca gcatgatggc gcactggata tcaaaaatag cagcgattt  720
atcaccatca gctacaacgt gtttaaagac catgataaag tgaccctgat tggtgcaagc  780
gatagccgta tggcagatga aggtcatctg cgtgttaccc tgcatcacaa ttattacaaa  840
aatgttaccc agcgtctgcc tcgtgttcgt tttggtcagg ttcatatcta taacaactac  900
tatgagttta gcaacctggc cgattatgac tttcagtatg catggggtgt tggtgttgaa  960
agcaaaatct atgcccagaa caactatttc agcttcgatt gggatattga cccgagcaaa 1020
attatcaaag tttggagcaa aaacgaagaa agcatgtatg aaagcggtac gattgttgat 1080
ctgccgaatg gtcgtcgtta tattgatctg gttcaagct ataatgaaag caatacctg 1140
cagctgaaaa agaggttgg ttggaaaccg atgttctatc atgttattca tccgaccccg 1200
agcgttccgg cactggttaa agcaaaagcc ggtgcaggta atctgcat            1248
``` |
| 53 | ```
aaagaactgg gtcatgatgt gctgaaaccg aatgatggtt gggcaagcta tggtgaaggt   60
acaaccggtg gtagcgaagc aagtccggat aatgtttata ccgttaccaa taaaagcgaa  120
ctggttcagg cactgggtgg taataatcat accaatcagt ataattccac cccgaaaatc  180
atctatgtga aaggcaccat tgaactgaac gtggatgata taatcagcc ggttggtccg  240
gaatattatg atgatccgca ttatgatttt gaagcctatc tgaaagagta tgatccgaaa  300
aaatgggggca aaaaagaagt tagcggtccg ctggaagaag cacgcgcacg tagccagaaa  360
aaacagaaag aacgtattgt tgtgaatgtg ggtagcaaca ccagcattat tggtgttggt  420
aaagatgcca aaattgtggg tggtggtttc ctgattaaaa acgtggataa tgtgatcatc  480
cgcaacatcg aatttgaagc accggtgat tttttccgg aatgggatcc gaccgatggt  540
gaatatggcg aatggaatag cgaatatgat agcattacca tcgaaagcag ccatcatatt  600
tggatcgatc acaataccct taccgatggc gatcatccgg ataaaagcct gggcacctat  660
tttggtcgtc cgtttcagca gcatgatggc gcactggata tcaaaaatag cagcgattt  720
atcaccatca gctacaacgt gtttaaagac catgataaag tgagcctgat tggttcaagc  780
gatagccgta aaccgatga aggtcatctg aaagttaccc tgcatcacaa ctattacaaa  840
aatgttaccc agcgtctgcc tcgtgttcgt tttggtcagg ttcatatcta taacaactac  900
tatgagttta gcaacctggc cgattatgac tttcagtatg catggggtgt tggtgttgaa  960
``` |

TABLE 8-continued

Amino acid and nucleotide sequences disclosed herein.

SEQ ID NO: Sequence

```
          agcaaaatct atgcccagaa caactatttc agcttcgatt gggatattga cccgagcaaa 1020
          attatcaaag tttggagcaa aaacgaagaa agcatgtatg aaagcggtac gattgttgat 1080
          ctgccgaatg gtcgtcgtta tattgatctg gttgcaagct ataatgaaag caatacccctg 1140
          cagctgaaaa aagaggttgg ttggaaaccg atgttctatc atgttattca tccgaccccg 1200
          agcgttccgg cactggttaa agcaaaagcc ggtgcaggta atctgcat              1248
```

SEQUENCE LISTING

<160> NUMBER OF SEQ ID NOS: 53

<210> SEQ ID NO 1
<211> LENGTH: 416
<212> TYPE: PRT
<213> ORGANISM: Bacillus spec

<400> SEQUENCE: 1

```
Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Tyr Lys Asn Val Thr Gln Arg Leu Pro Arg
        275                 280                 285
```

-continued

```
Val Arg Phe Gly Gln Val His Ile Tyr Asn Asn Tyr Glu Phe Ser
    290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
                340                 345                 350

Tyr Glu Thr Gly Thr Ile Val Asp Leu Pro Asn Gly Arg Arg Tyr Ile
                355                 360                 365

Asp Leu Val Ala Ser Tyr Asn Glu Ser Asn Thr Leu Gln Leu Lys Lys
370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 2
<211> LENGTH: 416
<212> TYPE: PRT
<213> ORGANISM: Bacillus spec

<400> SEQUENCE: 2

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
                20                  25                  30

Phe Val Val Thr Asn Arg Thr Glu Leu Ile Gln Ala Leu Gly Gly Asn
            35                  40                  45

Asn His Thr Asn Gln Tyr Asn Ser Val Pro Lys Ile Ile Tyr Val Lys
50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
            115                 120                 125

Tyr Val Gly Ser Asn Thr Ser Ile Ile Gly Val Gly Lys Asp Ala Lys
        130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Ala Leu Asp Ile Thr Asn Ser Ser Asp Phe
225                 230                 235                 240

Ile Thr Ile Ser Tyr Asn Val Phe Thr Asn His Asp Lys Val Thr Leu
                245                 250                 255
```

-continued

Ile Gly Ala Ser Asp Ser Arg Met Ala Asp Ser Gly His Leu Arg Val
              260                 265                 270

Thr Leu His His Asn Tyr Tyr Lys Asn Val Thr Gln Arg Leu Pro Arg
              275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                  325                 330                 335

Asp Pro Ser Leu Ile Ile Lys Val Trp Ser Lys Asn Glu Glu Ser Met
              340                 345                 350

Tyr Glu Thr Gly Thr Ile Val Asp Leu Pro Asn Gly Arg Arg Tyr Ile
              355                 360                 365

Asp Leu Val Ala Ser Tyr Asn Glu Ser Asn Thr Leu Gln Leu Lys Lys
              370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                  405                 410                 415

<210> SEQ ID NO 3
<211> LENGTH: 416
<212> TYPE: PRT
<213> ORGANISM: Bacillus spec

<400> SEQUENCE: 3

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
              20                  25                  30

Phe Val Val Thr Asn Arg Thr Glu Leu Ile Gln Ala Leu Gly Gly Asn
              35                  40                  45

Asn His Thr Asn Gln Tyr Asn Ser Val Pro Lys Ile Ile Tyr Val Lys
50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                  85                  90                  95

Tyr Asp Pro Ala Thr Trp Gly Lys Lys Glu Val Glu Gly Pro Leu Glu
              100                 105                 110

Glu Ala Arg Val Arg Ser Gln Lys Lys Gln Lys Asp Arg Ile Met Val
              115                 120                 125

Tyr Val Gly Ser Asn Thr Ser Ile Ile Gly Val Gly Lys Asp Ala Lys
              130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                  165                 170                 175

Pro Thr Asp Gly Thr Leu Gly Glu Trp Asn Ser Glu Tyr Asp Ser Ile
              180                 185                 190

Ser Ile Glu Gly Ser Ser His Ile Trp Ile Asp His Asn Thr Phe Thr
              195                 200                 205

Asp Gly Asp His Pro Asp Arg Ser Leu Gly Thr Tyr Phe Gly Arg Pro

```
                210                 215                 220
Phe Gln Gln His Asp Gly Ala Leu Asp Ile Ser Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
                260                 265                 270

Thr Leu His His Asn Tyr Tyr Lys Asn Val Thr Gln Arg Leu Pro Arg
                275                 280                 285

Val Arg Phe Gly Gln Val His Ile Tyr Asn Asn Tyr Glu Phe Ser
290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
                340                 345                 350

Tyr Glu Thr Gly Thr Ile Val Asp Leu Pro Asn Gly Arg Arg Tyr Ile
                355                 360                 365

Asp Leu Val Ala Ser Tyr Asn Glu Ser Asn Thr Leu Gln Leu Lys Lys
                370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 4
<211> LENGTH: 416
<212> TYPE: PRT
<213> ORGANISM: Bacillus spec

<400> SEQUENCE: 4

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
                20                  25                  30

Phe Val Val Thr Asn Arg Thr Glu Leu Ile Gln Ala Leu Gly Gly Asn
                35                  40                  45

Asn His Thr Asn Gln Tyr Asn Ser Val Pro Lys Ile Ile Tyr Val Lys
50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
                100                 105                 110

Glu Ala Arg Val Arg Ser Gln Lys Gln Lys Asp Arg Ile Met Val
                115                 120                 125

Tyr Val Gly Ser Asn Thr Ser Ile Ile Gly Val Gly Lys Asp Ala Lys
                130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175
```

```
Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
            210                 215                 220

Phe Gln Gln His Asp Gly Ala Leu Asp Ile Asn Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
        290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
        370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 5
<211> LENGTH: 416
<212> TYPE: PRT
<213> ORGANISM: Bacillus spec

<400> SEQUENCE: 5

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140
```

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Ala Leu Asp Ile Cys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
                260                 265                 270

Thr Leu His His Asn Tyr Tyr Lys Asn Val Thr Gln Arg Leu Pro Arg
            275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 6
<211> LENGTH: 416
<212> TYPE: PRT
<213> ORGANISM: Bacillus spec

<400> SEQUENCE: 6

Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
            20                  25                  30

Tyr Thr Val Thr Asn Lys Thr Glu Leu Val Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Glu Leu Asn Val Asp Asp Asn Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu

```
            100                 105                 110
    Glu Ala Arg Ala Arg Ser Gln Lys Lys Gln Lys Glu Arg Ile Val Val
                115                 120                 125

Asn Val Gly Ser Asn Thr Ser Ile Ile Gly Val Gly Lys Asp Ala Lys
    130                 135                 140

Ile Val Gly Gly Gly Phe Leu Ile Lys Asn Val Asp Asn Val Ile Ile
    145                 150                 155                 160

Arg Asn Ile Glu Phe Glu Ala Pro Val Asp Tyr Phe Pro Glu Trp Asp
                    165                 170                 175

Pro Thr Asp Gly Thr Leu Gly Glu Trp Asn Ser Glu Tyr Asp Ser Ile
                    180                 185                 190

Thr Ile Glu Gly Ser His His Ile Trp Ile Asp His Asn Thr Phe Thr
                    195                 200                 205

Asp Gly Asp His Pro Asp Lys Ser Leu Gly Thr Tyr Phe Gly Arg Pro
        210                 215                 220

Phe Gln Gln His Asp Gly Ala Leu Asp Ile Lys Asn Ser Ser Asp Phe
    225                 230                 235                 240

Ile Thr Ile Ser Tyr Asn Val Phe Lys Asp His Asp Lys Val Thr Leu
                    245                 250                 255

Ile Gly Ala Ser Asp Ser Arg Met Ala Asp Glu Gly His Leu Arg Val
                    260                 265                 270

Thr Leu His His Asn Tyr Tyr Lys Asn Val Thr Gln Arg Leu Pro Arg
                    275                 280                 285

Val Arg Phe Gly Gln Val His Ile Tyr Asn Asn Tyr Glu Phe Ser
        290                 295                 300

Asn Leu Ala Asp Tyr Asp Phe Gln Tyr Ala Trp Gly Val Gly Val Glu
    305                 310                 315                 320

Ser Lys Ile Tyr Ala Gln Asn Asn Tyr Phe Ser Phe Asp Trp Asp Ile
                    325                 330                 335

Asp Pro Ser Lys Ile Ile Lys Val Trp Ser Lys Asn Glu Glu Ser Met
                    340                 345                 350

Tyr Glu Ser Gly Thr Ile Val Asp Leu Pro Asn Gly Arg Arg Tyr Ile
                    355                 360                 365

Asp Leu Val Ala Ser Tyr Asn Glu Ser Asn Thr Leu Gln Leu Lys Lys
        370                 375                 380

Glu Val Gly Trp Lys Pro Met Phe Tyr His Val Ile His Pro Thr Pro
    385                 390                 395                 400

Ser Val Pro Ala Leu Val Lys Ala Lys Ala Gly Ala Gly Asn Leu His
                    405                 410                 415

<210> SEQ ID NO 7
<211> LENGTH: 416
<212> TYPE: PRT
<213> ORGANISM: Bacillus spec

<400> SEQUENCE: 7

Lys Glu Leu Gly His Asp Val Leu Lys Pro Tyr Asp Gly Trp Ala Ser
    1               5                   10                  15

Tyr Gly Glu Gly Thr Thr Gly Gly Ser Met Ala Ser Pro Gln Asn Val
                    20                  25                  30

Tyr Thr Val Thr Asn Lys Thr Glu Leu Val Gln Ala Leu Gly Gly Asn
                35                  40                  45

Asn His Thr Asn Gln Tyr Asn Ser Val Pro Lys Ile Ile Tyr Val Lys
    50                  55                  60
```

```
Gly Thr Ile Glu Leu Asn Val Asp Asp Asn Gln Pro Val Gly Pro
 65                  70                  75                  80

Glu Phe Tyr Lys Asp Pro His Tyr Asp Phe Glu Ala Tyr Leu Lys Glu
                 85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
        115                 120                 125

Asn Val Gly Ser Asn Thr Ser Ile Ile Gly Val Gly Lys Asp Ala Lys
130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Thr Ile Glu Gly Ser His His Ile Trp Ile Asp His Asn Thr Phe Thr
        195                 200                 205

Asp Gly Asp His Pro Asp Lys Ser Leu Gly Thr Tyr Phe Gly Arg Pro
210                 215                 220

Phe Gln Gln His Asp Gly Ala Leu Asp Ile Thr Asn Ser Ser Asp Phe
225                 230                 235                 240

Ile Thr Ile Ser Tyr Asn Val Phe Lys Asp His Asp Lys Val Thr Leu
                245                 250                 255

Ile Gly Ala Ser Asp Ser Arg Met Ala Asp Glu Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 8
<211> LENGTH: 416
<212> TYPE: PRT
<213> ORGANISM: Bacillus spec

<400> SEQUENCE: 8

Lys Glu Leu Gly His Asp Val Leu Lys Pro Tyr Asp Gly Trp Ala Ser
 1               5                  10                  15

Tyr Gly Glu Gly Thr Thr Gly Gly Ser Met Ala Ser Pro Gln Asn Val
                 20                  25                  30
```

Tyr Thr Val Thr Asn Lys Thr Glu Leu Val Gln Ala Leu Gly Gly Asn
            35                  40                  45

Asn His Thr Asn Gln Tyr Asn Ser Val Pro Lys Ile Ile Tyr Val Lys
 50                  55                  60

Gly Thr Ile Glu Leu Asn Val Asp Asp Asn Asn Gln Pro Val Gly Pro
 65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
                100                 105                 110

Glu Ala Arg Ala Arg Ser Gln Lys Lys Gln Lys Glu Arg Ile Val Val
            115                 120                 125

Asn Val Gly Ser Asn Thr Ser Ile Ile Gly Val Gly Lys Asp Ala Lys
130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
                180                 185                 190

Thr Ile Glu Gly Ser His His Ile Trp Ile Asp His Asn Thr Phe Thr
            195                 200                 205

Asp Gly Asp His Pro Asp Lys Ser Leu Gly Thr Tyr Phe Gly Arg Pro
210                 215                 220

Phe Gln Gln His Asp Gly Ala Leu Asp Ile Ser Asn Ser Ser Asp Phe
225                 230                 235                 240

Ile Thr Ile Ser Tyr Asn Val Phe Lys Asp His Asp Lys Val Thr Leu
                245                 250                 255

Ile Gly Ala Ser Asp Ser Arg Met Ala Asp Glu Gly His Leu Arg Val
            260                 265                 270

Thr Leu His His Asn Tyr Tyr Lys Asn Val Thr Gln Arg Leu Pro Arg
            275                 280                 285

Val Arg Phe Gly Gln Val His Ile Tyr Asn Asn Tyr Tyr Glu Phe Ser
            290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
                340                 345                 350

Tyr Glu Ser Gly Thr Ile Val Asp Leu Pro Asn Gly Arg Arg Tyr Ile
            355                 360                 365

Asp Leu Val Ala Ser Tyr Asn Glu Ser Asn Thr Leu Gln Leu Lys Lys
370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 9
<211> LENGTH: 416
<212> TYPE: PRT
<213> ORGANISM: Bacillus spec

```
<400> SEQUENCE: 9

Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
            20                  25                  30

Tyr Thr Val Thr Asn Lys Thr Glu Leu Val Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Glu Leu Asn Val Asp Asp Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Gln Lys Glu Arg Ile Val Val
            115                 120                 125

Asn Val Gly Ser Asn Thr Ser Ile Ile Gly Val Gly Lys Asp Ala Lys
    130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Thr Ile Glu Gly Ser His His Ile Trp Ile Asp His Asn Thr Phe Thr
        195                 200                 205

Asp Gly Asp His Pro Asp Lys Ser Leu Gly Thr Tyr Phe Gly Arg Pro
    210                 215                 220

Phe Gln Gln His Asp Gly Ala Leu Asp Ile Asn Asn Ser Ser Asp Phe
225                 230                 235                 240

Ile Thr Ile Ser Tyr Asn Val Phe Lys Asp His Asp Lys Val Thr Leu
                245                 250                 255

Ile Gly Ala Ser Asp Ser Arg Met Ala Asp Glu Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
    290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415
```

<210> SEQ ID NO 10
<211> LENGTH: 416
<212> TYPE: PRT
<213> ORGANISM: Bacillus spec

<400> SEQUENCE: 10

Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
            20                  25                  30

Tyr Thr Val Thr Asn Lys Thr Glu Leu Val Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Glu Leu Asn Val Asp Asp Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
        115                 120                 125

Asn Val Gly Ser Asn Thr Ser Ile Ile Gly Val Gly Lys Asp Ala Lys
    130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Thr Ile Glu Gly Ser His His Ile Trp Ile Asp His Asn Thr Phe Thr
        195                 200                 205

Asp Gly Asp His Pro Asp Lys Ser Leu Gly Thr Tyr Phe Gly Arg Pro
    210                 215                 220

Phe Gln Gln His Asp Gly Ala Leu Asp Ile Cys Asn Ser Ser Asp Phe
225                 230                 235                 240

Ile Thr Ile Ser Tyr Asn Val Phe Lys Asp His Asp Lys Val Thr Leu
                245                 250                 255

Ile Gly Ala Ser Asp Ser Arg Met Ala Asp Glu Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
    290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys

```
                  370                 375                 380
Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 11
<211> LENGTH: 416
<212> TYPE: PRT
<213> ORGANISM: Bacillus spec

<400> SEQUENCE: 11

Lys Glu Leu Gly His Asp Val Leu Lys Pro Asn Asp Gly Trp Ala Ser
1               5                   10                  15

Tyr Gly Glu Gly Thr Thr Gly Gly Ser Glu Ala Ser Pro Asp Asn Val
                20                  25                  30

Tyr Thr Val Thr Asn Lys Ser Glu Leu Val Gln Ala Leu Gly Gly Asn
            35                  40                  45

Asn His Thr Asn Gln Tyr Asn Ser Thr Pro Lys Ile Ile Tyr Val Lys
        50                  55                  60

Gly Thr Ile Glu Leu Asn Val Asp Asp Asn Asn Gln Pro Val Gly Pro
65                  70                  75                  80

Glu Tyr Tyr Asp Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
                100                 105                 110

Glu Ala Arg Ala Arg Ser Gln Lys Lys Gln Lys Glu Arg Ile Val Val
            115                 120                 125

Asn Val Gly Ser Asn Thr Ser Ile Ile Gly Val Gly Lys Asp Ala Lys
        130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Phe Phe Pro Glu Trp Asp
                165                 170                 175

Pro Thr Asp Gly Glu Tyr Gly Glu Trp Asn Ser Glu Tyr Asp Ser Ile
                180                 185                 190

Thr Ile Glu Ser Ser His His Ile Trp Ile Asp His Asn Thr Phe Thr
            195                 200                 205

Asp Gly Asp His Pro Asp Lys Ser Leu Gly Thr Tyr Phe Gly Arg Pro
        210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
                260                 265                 270

Thr Leu His His Asn Tyr Tyr Lys Asn Val Thr Gln Arg Leu Pro Arg
            275                 280                 285

Val Arg Phe Gly Gln Val His Ile Tyr Asn Asn Tyr Tyr Glu Phe Ser
        290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335
```

```
Asp Pro Ser Lys Ile Ile Lys Val Trp Ser Lys Asn Glu Glu Ser Met
                340                 345                 350

Tyr Glu Ser Gly Thr Ile Val Asp Leu Pro Asn Gly Arg Arg Tyr Ile
            355                 360                 365

Asp Leu Val Ala Ser Tyr Asn Glu Ser Asn Thr Leu Gln Leu Lys Lys
        370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 12
<211> LENGTH: 416
<212> TYPE: PRT
<213> ORGANISM: Bacillus spec

<400> SEQUENCE: 12

Lys Glu Leu Gly His Asp Val Leu Lys Pro Asn Asp Gly Trp Ala Ser
1               5                   10                  15

Tyr Gly Glu Gly Thr Thr Gly Gly Ser Glu Ala Ser Pro Asp Asn Val
                20                  25                  30

Tyr Thr Val Thr Asn Lys Ser Glu Leu Val Gln Ala Leu Gly Gly Asn
            35                  40                  45

Asn His Thr Asn Gln Tyr Asn Ser Thr Pro Lys Ile Ile Tyr Val Lys
50                  55                  60

Gly Thr Ile Glu Leu Asn Val Asp Asp Asn Gln Pro Val Gly Pro
65                  70                  75                  80

Glu Tyr Tyr Asp Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
        115                 120                 125

Asn Val Gly Ser Asn Thr Ser Ile Ile Gly Val Gly Lys Asp Ala Lys
130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Phe Phe Pro Glu Trp Asp
                165                 170                 175

Pro Thr Asp Gly Glu Tyr Gly Glu Trp Asn Ser Glu Tyr Asp Ser Ile
            180                 185                 190

Thr Ile Glu Ser Ser His His Ile Trp Ile Asp His Asn Thr Phe Thr
        195                 200                 205

Asp Gly Asp His Pro Asp Lys Ser Leu Gly Thr Tyr Phe Gly Arg Pro
210                 215                 220

Phe Gln Gln His Asp Gly Ala Leu Asp Ile Thr Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
290                 295                 300
```

```
Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
            325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
            355                 360                 365

Asp Leu Val Ala Ser Tyr Asn Glu Ser Asn Thr Leu Gln Leu Lys Lys
            370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
            405                 410                 415
```

<210> SEQ ID NO 13
<211> LENGTH: 416
<212> TYPE: PRT
<213> ORGANISM: Bacillus spec

<400> SEQUENCE: 13

```
Lys Glu Leu Gly His Asp Val Leu Lys Pro Asn Asp Gly Trp Ala Ser
1               5                   10                  15

Tyr Gly Glu Gly Thr Thr Gly Ser Glu Ala Ser Pro Asp Asn Val
            20                  25                  30

Tyr Thr Val Thr Asn Lys Ser Glu Leu Val Gln Ala Leu Gly Gly Asn
            35                  40                  45

Asn His Thr Asn Gln Tyr Asn Ser Thr Pro Lys Ile Ile Tyr Val Lys
    50                  55                  60

Gly Thr Ile Glu Leu Asn Val Asp Asp Asn Asn Gln Pro Val Gly Pro
65              70                  75                  80

Glu Tyr Tyr Asp Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
            115                 120                 125

Asn Val Gly Ser Asn Thr Ser Ile Ile Gly Val Gly Lys Asp Ala Lys
            130                 135                 140

Ile Val Gly Gly Gly Phe Leu Ile Leu Lys Asn Val Asp Asn Val Ile Ile
145                 150                 155                 160

Arg Asn Ile Glu Phe Glu Ala Pro Val Asp Phe Phe Pro Glu Trp Asp
                165                 170                 175

Pro Thr Asp Gly Glu Tyr Gly Glu Trp Asn Ser Glu Tyr Asp Ser Ile
            180                 185                 190

Thr Ile Glu Ser Ser His His Ile Trp Ile Asp His Asn Thr Phe Thr
            195                 200                 205

Asp Gly Asp His Pro Asp Lys Ser Leu Gly Thr Tyr Phe Gly Arg Pro
    210                 215                 220

Phe Gln Gln His Asp Gly Ala Leu Asp Ile Ser Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
```

```
                260                265                270
Thr Leu His His Asn Tyr Tyr Lys Asn Val Thr Gln Arg Leu Pro Arg
            275                280                285
Val Arg Phe Gly Gln Val His Ile Tyr Asn Asn Tyr Tyr Glu Phe Ser
290                295                300
Asn Leu Ala Asp Tyr Asp Phe Gln Tyr Ala Trp Gly Val Gly Val Glu
305                310                315                320
Ser Lys Ile Tyr Ala Gln Asn Asn Tyr Phe Ser Phe Asp Trp Asp Ile
                325                330                335
Asp Pro Ser Lys Ile Ile Lys Val Trp Ser Lys Asn Glu Glu Ser Met
                340                345                350
Tyr Glu Ser Gly Thr Ile Val Asp Leu Pro Asn Gly Arg Arg Tyr Ile
            355                360                365
Asp Leu Val Ala Ser Tyr Asn Glu Ser Asn Thr Leu Gln Leu Lys Lys
            370                375                380
Glu Val Gly Trp Lys Pro Met Phe Tyr His Val Ile His Pro Thr Pro
385                390                395                400
Ser Val Pro Ala Leu Val Lys Ala Lys Ala Gly Ala Gly Asn Leu His
                405                410                415

<210> SEQ ID NO 14
<211> LENGTH: 416
<212> TYPE: PRT
<213> ORGANISM: Bacillus spec

<400> SEQUENCE: 14

Lys Glu Leu Gly His Asp Val Leu Lys Pro Asn Asp Gly Trp Ala Ser
1               5                   10                  15
Tyr Gly Glu Gly Thr Thr Gly Gly Ser Glu Ala Ser Pro Asp Asn Val
                20                  25                  30
Tyr Thr Val Thr Asn Lys Ser Glu Leu Val Gln Ala Leu Gly Gly Asn
            35                  40                  45
Asn His Thr Asn Gln Tyr Asn Ser Thr Pro Lys Ile Ile Tyr Val Lys
        50                  55                  60
Gly Thr Ile Glu Leu Asn Val Asp Asp Asn Asn Gln Pro Val Gly Pro
65                  70                  75                  80
Glu Tyr Tyr Asp Asp Pro His Tyr Asp Phe Glu Ala Tyr Leu Lys Glu
                85                  90                  95
Tyr Asp Pro Lys Lys Trp Gly Lys Lys Glu Val Ser Gly Pro Leu Glu
                100                 105                 110
Glu Ala Arg Ala Arg Ser Gln Lys Gln Lys Glu Arg Ile Val Val
            115                 120                 125
Asn Val Gly Ser Asn Thr Ser Ile Ile Gly Val Gly Lys Asp Ala Lys
        130                 135                 140
Ile Val Gly Gly Gly Phe Leu Ile Lys Asn Val Asp Asn Val Ile Ile
145                 150                 155                 160
Arg Asn Ile Glu Phe Glu Ala Pro Val Asp Phe Phe Pro Glu Trp Asp
                165                 170                 175
Pro Thr Asp Gly Glu Tyr Gly Glu Trp Asn Ser Glu Tyr Asp Ser Ile
                180                 185                 190
Thr Ile Glu Ser Ser His His Ile Trp Ile Asp His Asn Thr Phe Thr
            195                 200                 205
Asp Gly Asp His Pro Asp Lys Ser Leu Gly Thr Tyr Phe Gly Arg Pro
        210                 215                 220
```

-continued

```
Phe Gln Gln His Asp Gly Ala Leu Asp Ile Asn Asn Ser Ser Asp Phe
225                 230                 235                 240

Ile Thr Ile Ser Tyr Asn Val Phe Lys Asp His Asp Lys Val Ser Leu
            245                 250                 255

Ile Gly Ser Ser Asp Ser Arg Lys Thr Asp Glu Gly His Leu Lys Val
        260                 265                 270

Thr Leu His His Asn Tyr Tyr Lys Asn Val Thr Gln Arg Leu Pro Arg
    275                 280                 285

Val Arg Phe Gly Gln Val His Ile Tyr Asn Asn Tyr Glu Phe Ser
290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
            325                 330                 335

Asp Pro Ser Lys Ile Ile Lys Val Trp Ser Lys Asn Glu Glu Ser Met
        340                 345                 350

Tyr Glu Ser Gly Thr Ile Val Asp Leu Pro Asn Gly Arg Arg Tyr Ile
    355                 360                 365

Asp Leu Val Ala Ser Tyr Asn Glu Ser Asn Thr Leu Gln Leu Lys Lys
370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
            405                 410                 415
```

<210> SEQ ID NO 15
<211> LENGTH: 416
<212> TYPE: PRT
<213> ORGANISM: Bacillus spec

<400> SEQUENCE: 15

```
Lys Glu Leu Gly His Asp Val Leu Lys Pro Asn Asp Gly Trp Ala Ser
1               5                   10                  15

Tyr Gly Glu Gly Thr Thr Gly Gly Ser Glu Ala Ser Pro Asp Asn Val
            20                  25                  30

Tyr Thr Val Thr Asn Lys Ser Glu Leu Val Gln Ala Leu Gly Gly Asn
        35                  40                  45

Asn His Thr Asn Gln Tyr Asn Ser Thr Pro Lys Ile Ile Tyr Val Lys
    50                  55                  60

Gly Thr Ile Glu Leu Asn Val Asp Asp Asn Gln Pro Val Gly Pro
65                  70                  75                  80

Glu Tyr Tyr Asp Asp Pro His Tyr Asp Phe Glu Ala Tyr Leu Lys Glu
            85                  90                  95

Tyr Asp Pro Lys Lys Trp Gly Lys Lys Glu Val Ser Gly Pro Leu Glu
        100                 105                 110

Glu Ala Arg Ala Arg Ser Gln Lys Lys Gln Lys Glu Arg Ile Val Val
    115                 120                 125

Asn Val Gly Ser Asn Thr Ser Ile Ile Gly Val Gly Lys Asp Ala Lys
130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Phe Phe Pro Glu Trp Asp
            165                 170                 175

Pro Thr Asp Gly Glu Tyr Gly Glu Trp Asn Ser Glu Tyr Asp Ser Ile
        180                 185                 190
```

```
Thr Ile Glu Ser Ser His His Ile Trp Ile Asp His Asn Thr Phe Thr
            195                 200                 205

Asp Gly Asp His Pro Asp Lys Ser Leu Gly Thr Tyr Phe Gly Arg Pro
210                 215                 220

Phe Gln Gln His Asp Gly Ala Leu Asp Ile Cys Asn Ser Ser Asp Phe
225                 230                 235                 240

Ile Thr Ile Ser Tyr Asn Val Phe Lys Asp His Asp Lys Val Ser Leu
            245                 250                 255

Ile Gly Ser Ser Asp Ser Arg Lys Thr Asp Glu Gly His Leu Lys Val
            260                 265                 270

Thr Leu His His Asn Tyr Tyr Lys Asn Val Thr Gln Arg Leu Pro Arg
            275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
            325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
            355                 360                 365

Asp Leu Val Ala Ser Tyr Asn Glu Ser Asn Thr Leu Gln Leu Lys Lys
            370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
            405                 410                 415

<210> SEQ ID NO 16
<211> LENGTH: 1248
<212> TYPE: DNA
<213> ORGANISM: Bacillus spec

<400> SEQUENCE: 16
aaagaactgg gtcatgaagt tctgaaaccg tatgatggtt gggcagcgta tggtgaaggt    60
acaaccggtg gtgcaatggc aagtccgcag aatgttttg ttgttaccaa tcgtaccgaa    120
ctgattcagg cactgggtgg taataatcat accaatcagt ataattccgt gccgaaaatc    180
atctatgtga aaggcaccat tgatctgaac gtggatgata taatcagcc ggttggtccg    240 gatttctata agatccgca ttttgatttt gaggcctatc tgcgtgaata tgatccggca    300
acctggggta aaaagaagt tgaaggtccg ctggaagaag cacgcgttcg tagccagaaa    360
aaacagaaag atcgtatcat ggtttatgtg ggtagcaaca ccagcattat tggtgttggt    420
aaagacgcga aaatcaaagg tggtggtttc ctgattaaaa acgtggataa tgtgatcatc    480
cgcaacatcg aatttgaagc accgctggat tattttccgg aatgggatcc gaccgatggc    540
accctgggtg aatggaatag cgaatatgat agcattagca ttgaaggcag cagccatatt    600
tggattgatc acaataccctt taccgatggc gatcatccgg atcgtagcct gggcacctat    660
tttggtcgtc cgtttcagca gcatgatggc gcactggata tcaaaaatag cagcgatttt    720
atcaccatca gctacaacgt gtttaccaac cacgataaag ttaccctgat ggtgcaagc    780 gatagccgta tggcagatag cggtcatctg cgtgttaccc tgcatcacaa ttattacaaa    840
```

| | |
|---|---|
| aatgttaccc agcgtctgcc tcgtgttcgt tttggtcagg ttcatatcta taacaactac | 900 |
| tatgagtttta gcaacctggc cgattatgat tttcagtatg catggggtgt tggtgtgttt | 960 |
| agccagattt atgcacagaa caactatttc agcttcgatt gggatattga tccgagcctg | 1020 |
| attatcaaag tttggagcaa aaatgaagaa agcatgtatg aaaccggcac catcgttgat | 1080 |
| ctgccgaatg gtcgtcgtta tattgatctg gttgcaagct ataatgaaag caatacccctg | 1140 |
| cagctgaaaa aagaggttac ctggaaaccg atgttctatc atgttattca tccgaccccg | 1200 |
| agcgttccgg cactggttaa agcaaaagcc ggtgcaggta atctgcat | 1248 |

<210> SEQ ID NO 17
<211> LENGTH: 1248
<212> TYPE: DNA
<213> ORGANISM: Bacillus spec

<400> SEQUENCE: 17

| | |
|---|---|
| aaagaactgg gtcatgaagt tctgaaaccg tatgatggtt gggcagcgta tggtgaaggt | 60 |
| acaaccggtg gtgcaatggc aagtccgcag aatgttttg ttgttaccaa tcgtaccgaa | 120 |
| ctgattcagg cactgggtgg taataatcat accaatcagt ataattccgt gccgaaaatc | 180 |
| atctatgtga aaggcaccat tgatctgaac gtggatgata ataatcagcc ggttggtccg | 240 |
| gatttctata agatccgca ttttgatttt gaggcctatc tgcgtgaata tgatccggca | 300 |
| acctggggta aaaagaagt tgaaggtccg ctggaagaag cacgcgttcg tagccagaaa | 360 |
| aaacagaaag atcgtatcat ggtttatgtg ggtagcaaca ccagcattat tggtgttggt | 420 |
| aaagacgcga aaatcaaagg tggtggtttc ctgattaaaa acgtggataa tgtgatcatc | 480 |
| cgcaacatcg aatttgaagc accgctggat tattttccgg aatgggatcc gaccgatggc | 540 |
| acctgggtg aatggaatag cgaatatgat agcattagca ttgaaggcag cagccatatt | 600 |
| tggattgatc acaataccct taccgatggc gatcatccgg atcgtagcct gggcacctat | 660 |
| tttggtcgtc cgtttcagca gcatgatggc gcactggata tcaccaatag cagcgattt | 720 |
| atcaccatca gctacaacgt gtttaccaac cacgataaag ttaccctgat tggtgcaagc | 780 |
| gatagccgta tggcagatag cggtcatctg cgtgttaccc tgcatcacaa ttattacaaa | 840 |
| aatgttaccc agcgtctgcc tcgtgttcgt tttggtcagg ttcatatcta taacaactac | 900 |
| tatgagtttta gcaacctggc cgattatgat tttcagtatg catggggtgt tggtgtgttt | 960 |
| agccagattt atgcacagaa caactatttc agcttcgatt gggatattga tccgagcctg | 1020 |
| attatcaaag tttggagcaa aaatgaagaa agcatgtatg aaaccggcac catcgttgat | 1080 |
| ctgccgaatg gtcgtcgtta tattgatctg gttgcaagct ataatgaaag caatacccctg | 1140 |
| cagctgaaaa aagaggttac ctggaaaccg atgttctatc atgttattca tccgaccccg | 1200 |
| agcgttccgg cactggttaa agcaaaagcc ggtgcaggta atctgcat | 1248 |

<210> SEQ ID NO 18
<211> LENGTH: 1248
<212> TYPE: DNA
<213> ORGANISM: Bacillus spec

<400> SEQUENCE: 18

| | |
|---|---|
| aaagaactgg gtcatgaagt tctgaaaccg tatgatggtt gggcagcgta tggtgaaggt | 60 |
| acaaccggtg gtgcaatggc aagtccgcag aatgttttg ttgttaccaa tcgtaccgaa | 120 |
| ctgattcagg cactgggtgg taataatcat accaatcagt ataattccgt gccgaaaatc | 180 |
| atctatgtga aaggcaccat tgatctgaac gtggatgata ataatcagcc ggttggtccg | 240 |

```
gatttctata aagatccgca ttttgatttt gaggcctatc tgcgtgaata tgatccggca      300
acctggggta aaaagaagt tgaaggtccg ctggaagaag cacgcgttcg tagccagaaa       360
aaacagaaag atcgtatcat ggtttatgtg ggtagcaaca ccagcattat tggtgttggt      420
aaagacgcga aaatcaaagg tggtggtttc ctgattaaaa cgtggataa tgtgatcatc       480 cgcaacatcg aatttgaagc accgctggat tattttccgg aatgggatcc gaccgatggc     540
accctgggtg aatggaatag cgaatatgat agcattagca ttgaaggcag cagccatatt    600
tggattgatc acaataccttt taccgatggc gatcatccgg atcgtagcct gggcacctat    660
tttggtcgtc cgtttcagca gcatgatggc gcactggata tcagcaatag cagcgatttt   720
atcaccatca gctacaacgt gtttaccaac cacgataaag ttaccctgat tggtgcaagc   780
gatagccgta tggcagatag cggtcatctg cgtgttaccc tgcatcacaa ttattacaaa   840
aatgttaccc agcgtctgcc tcgtgttcgt tttggtcagg ttcatatcta taacaactac   900 tatgagtttta gcaacctggc cgattatgat tttcagtatg catggggtgt tggtgtgttt  960
agccagattt atgcacagaa caactatttc agcttcgatt gggatattga tccgagcctg  1020
attatcaaag tttggagcaa aaatgaagaa agcatgtatg aaaccggcac catcgttgat  1080
ctgccgaatg gtcgtcgtta tattgatctg gttgcaagct ataatgaaag caatacccctg 1140 cagctgaaaa aagaggttac ctggaaaccg atgttctatc atgttattca tccgaccccg  1200
agcgttccgg cactggttaa agcaaaagcc ggtgcaggta atctgcat              1248

<210> SEQ ID NO 19
<211> LENGTH: 1248
<212> TYPE: DNA
<213> ORGANISM: Bacillus spec

<400> SEQUENCE: 19
aaagaactgg gtcatgaagt tctgaaaccg tatgatggtt gggcagcgta tggtgaaggt       60
acaaccggtg gtgcaatggc aagtccgcag aatgtttttg ttgttaccaa tcgtaccgaa    120
ctgattcagg cactgggtgg taataatcat accaatcagt ataattccgt gccgaaaatc     180
atctatgtga aaggcaccat tgatctgaac gtggatgata taatcagcc ggttggtccg      240 gatttctata aagatccgca ttttgatttt gaggcctatc tgcgtgaata tgatccggca      300
acctggggta aaaagaagt tgaaggtccg ctggaagaag cacgcgttcg tagccagaaa       360
aaacagaaag atcgtatcat ggtttatgtg ggtagcaaca ccagcattat tggtgttggt      420
aaagacgcga aaatcaaagg tggtggtttc ctgattaaaa cgtggataa tgtgatcatc       480 cgcaacatcg aatttgaagc accgctggat tattttccgg aatgggatcc gaccgatggc     540
accctgggtg aatggaatag cgaatatgat agcattagca ttgaaggcag cagccatatt    600
tggattgatc acaataccttt taccgatggc gatcatccgg atcgtagcct gggcacctat    660
tttggtcgtc cgtttcagca gcatgatggc gcactggata tcaacaatag cagcgatttt   720
atcaccatca gctacaacgt gtttaccaac cacgataaag ttaccctgat tggtgcaagc   780
gatagccgta tggcagatag cggtcatctg cgtgttaccc tgcatcacaa ttattacaaa   840
aatgttaccc agcgtctgcc tcgtgttcgt tttggtcagg ttcatatcta taacaactac   900 tatgagtttta gcaacctggc cgattatgat tttcagtatg catggggtgt tggtgtgttt  960
agccagattt atgcacagaa caactatttc agcttcgatt gggatattga tccgagcctg  1020
attatcaaag tttggagcaa aaatgaagaa agcatgtatg aaaccggcac catcgttgat  1080
```

| ctgccgaatg gtcgtcgtta tattgatctg gttgcaagct ataatgaaag caataccctg | 1140 |
| cagctgaaaa aagaggttac ctggaaaccg atgttctatc atgttattca tccgaccccg | 1200 |
| agcgttccgg cactggttaa agcaaaagcc ggtgcaggta atctgcat | 1248 |

<210> SEQ ID NO 20
<211> LENGTH: 1248
<212> TYPE: DNA
<213> ORGANISM: Bacillus spec

<400> SEQUENCE: 20

| aaagaactgg gtcatgaagt tctgaaaccg tatgatggtt gggcagcgta tggtgaaggt | 60 |
| acaaccggtg gtgcaatggc aagtccgcag aatgttttg ttgttaccaa tcgtaccgaa | 120 |
| ctgattcagg cactgggtgg taataatcat accaatcagt ataattccgt gccgaaaatc | 180 |
| atctatgtga aaggcaccat tgatctgaac gtggatgata taatcagcc ggttggtccg | 240 |
| gatttctata agatccgca ttttgatttt gaggcctatc tgcgtgaata tgatccggca | 300 |
| acctggggta aaaagaagt tgaaggtccg ctggaagaag cacgcgttcg tagccagaaa | 360 |
| aaacagaaag atcgtatcat ggtttatgtg ggtagcaaca ccagcattat tggtgttggt | 420 |
| aaagacgcga aaatcaaagg tggtggtttc ctgattaaaa acgtggataa tgtgatcatc | 480 |
| cgcaacatcg aatttgaagc accgctggat tattttccgg aatgggatcc gaccgatggc | 540 |
| accctgggtg aatggaatag cgaatatgat agcattagca ttgaaggcag cagccatatt | 600 |
| tggattgatc acaataccctt taccgatggc gatcatccgg atcgtagcct gggcacctat | 660 |
| tttggtcgtc cgtttcagca gcatgatggc gcactggata tctgcaatag cagcgatttt | 720 |
| atcaccatca gctacaacgt gtttaccaac cacgataaag ttaccctgat tggtgcaagc | 780 |
| gatagccgta tggcagatag cggtcatctg cgtgttaccc tgcatcacaa ttattacaaa | 840 |
| aatgttaccc agcgtctgcc tcgtgttcgt tttggtcagg ttcatatcta taacaactac | 900 |
| tatgagttta gcaacctggc cgattatgat tttcagtatg catggggtgt tggtgtgttt | 960 |
| agccagattt atgcacagaa caactatttc agcttcgatt gggatattga tccgagcctg | 1020 |
| attatcaaag tttggagcaa aaatgaagaa agcatgtatg aaaccggcac catcgttgat | 1080 |
| ctgccgaatg gtcgtcgtta tattgatctg gttgcaagct ataatgaaag caataccctg | 1140 |
| cagctgaaaa aagaggttac ctggaaaccg atgttctatc atgttattca tccgaccccg | 1200 |
| agcgttccgg cactggttaa agcaaaagcc ggtgcaggta atctgcat | 1248 |

<210> SEQ ID NO 21
<211> LENGTH: 1248
<212> TYPE: DNA
<213> ORGANISM: Bacillus spec

<400> SEQUENCE: 21

| aaagaactgg gtcatgatgt gctgaaaccg tatgatggtt gggcaagcta tggtgaaggt | 60 |
| acaaccggtg gtagcatggc aagtccgcag aatgtttata ccgttaccaa taaaaccgaa | 120 |
| ctggttcagg cactgggtgg taataatcat accaatcagt ataattccgt gccgaaaatc | 180 |
| atctatgtga aaggcaccat tgaactgaac gtggatgata taatcagcc ggttggtccg | 240 |
| gaattctata agatccgca ttatgatttt gaagcctatc tgaaagagta tgatccgaaa | 300 |
| aaatggggca aaaagaagt tagcggtccg ctggaagaag cacgcgcacg tagccagaaa | 360 |
| aaacagaaag aacgtattgt tgtgaatgtg ggtagcaaca ccagcattat tggtgttggt | 420 |
| aaagatgcca aaattgtggg tggtggtttc ctgattaaaa acgtggataa tgtgatcatc | 480 |

```
cgcaacatcg aatttgaagc accggtggat tattttccgg aatgggatcc gaccgatggc      540
accctgggtg aatggaatag cgaatatgat agcattacca ttgaaggcag ccatcatatt      600
tggatcgatc acaataccct taccgatggc gatcatccgg ataaaagcct gggcacctat      660
tttggtcgtc cgtttcagca gcatgatggc gcactggata tcaaaaatag cagcgatttt      720
atcaccatca gctacaacgt gtttaaagac catgataaag tgaccctgat tggtgcaagc      780
gatagccgta tggcagatga aggtcatctg cgtgttaccc tgcatcacaa ttattacaaa      840
aatgttaccc agcgtctgcc tcgtgttcgt tttggtcagg ttcatatcta taacaactac      900
tatgagttta gcaacctggc cgattatgac tttcagtatg catggggtgt tggtgttgaa      960
agcaaaatct atgcccagaa caactatttc agcttcgatt gggatattga cccgagcaaa     1020
attatcaaag tttggagcaa aaacgaagaa agcatgtatg aaagcggtac gattgttgat     1080
ctgccgaatg gtcgtcgtta tattgatctg gttgcaagct ataatgaaag caatacccctg    1140 cagctgaaaa aagaggttgg ttggaaaccg atgttctatc atgttattca tccgaccccg     1200
agcgttccgg cactggttaa agcaaaagcc ggtgcaggta atctgcat                  1248
```

<210> SEQ ID NO 22
<211> LENGTH: 1248
<212> TYPE: DNA
<213> ORGANISM: Bacillus spec

<400> SEQUENCE: 22

```
aaagaactgg gtcatgatgt gctgaaaccg tatgatggtt gggcaagcta tggtgaaggt       60
acaaccggtg gtagcatggc aagtccgcag aatgtttata ccgttaccaa taaaaccgaa      120
ctggttcagg cactgggtgg taataatcat accaatcagt ataattccgt gccgaaaatc      180
atctatgtga aaggcaccat tgaactgaac gtggatgata taatcagcc ggttggtccg       240 gaattctata aagatccgca ttatgatttt gaagcctatc tgaaagagta tgatccgaaa      300
aaatggggca aaaagaagt tagcggtccg ctggaagaag cacgcgcacg tagccagaaa      360
aaacagaaag aacgtattgt tgtgaatgtg ggtagcaaca ccagcattat tggtgttggt      420
aaagatgcca aaattgtggg tggtggttc ctgattaaaa acgtggataa tgtgatcatc      480
cgcaacatcg aatttgaagc accggtggat tattttccgg aatgggatcc gaccgatggc      540
accctgggtg aatggaatag cgaatatgat agcattacca ttgaaggcag ccatcatatt      600
tggatcgatc acaataccct taccgatggc gatcatccgg ataaaagcct gggcacctat      660
tttggtcgtc cgtttcagca gcatgatggc gcactggata tcaccaatag cagcgatttt      720
atcaccatca gctacaacgt gtttaaagac catgataaag tgaccctgat tggtgcaagc      780
gatagccgta tggcagatga aggtcatctg cgtgttaccc tgcatcacaa ttattacaaa      840
aatgttaccc agcgtctgcc tcgtgttcgt tttggtcagg ttcatatcta taacaactac      900
tatgagttta gcaacctggc cgattatgac tttcagtatg catggggtgt tggtgttgaa      960
agcaaaatct atgcccagaa caactatttc agcttcgatt gggatattga cccgagcaaa     1020
attatcaaag tttggagcaa aaacgaagaa agcatgtatg aaagcggtac gattgttgat     1080
ctgccgaatg gtcgtcgtta tattgatctg gttgcaagct ataatgaaag caatacccctg    1140 cagctgaaaa aagaggttgg ttggaaaccg atgttctatc atgttattca tccgaccccg     1200
agcgttccgg cactggttaa agcaaaagcc ggtgcaggta atctgcat                  1248
```

<210> SEQ ID NO 23

<211> LENGTH: 1248
<212> TYPE: DNA
<213> ORGANISM: Bacillus spec

<400> SEQUENCE: 23

```
aaagaactgg gtcatgatgt gctgaaaccg tatgatggtt gggcaagcta tggtgaaggt      60
acaaccggtg gtagcatggc aagtccgcag aatgtttata ccgttaccaa taaaaccgaa     120
ctggttcagg cactgggtgg taataatcat accaatcagt ataattccgt gccgaaaatc     180
atctatgtga aaggcaccat tgaactgaac gtggatgata ataatcagcc ggttggtccg     240
gaattctata agatccgca ttatgatttt gaagcctatc tgaaagagta tgatccgaaa     300
aaatggggca aaaagaagt tagcggtccg ctggaagaag cacgcgcacg tagccagaaa     360
aaacagaaag aacgtattgt tgtgaatgtg ggtagcaaca ccagcattat tggtgttggt     420
aaagatgcca aaattgtggg tggtggtttc ctgattaaaa acgtggataa tgtgatcatc     480
cgcaacatcg aatttgaagc accggtggat tattttccgg aatgggatcc gaccgatggc     540
acctgggtg aatggaatag cgaatatgat agcattacca ttgaaggcag ccatcatatt     600
tggatcgatc acaataccct taccgatggc gatcatccgg ataaaagcct gggcacctat     660
tttggtcgtc cgtttcagca gcatgatggc gcactggata tcagcaatag cagcgatttt     720
atcaccatca gctacaacgt gtttaaagac catgataaag tgaccctgat tggtgcaagc     780
gatagccgta tggcagatga aggtcatctg cgtgttaccc tgcatcacaa ttattacaaa     840
aatgttaccc agcgtctgcc tcgtgttcgt tttggtcagg ttcatatcta taacaactac     900
tatgagttta gcaacctggc cgattatgac tttcagtatg catggggtgt tggtgttgaa     960
agcaaaatct atgcccagaa caactatttc agcttcgatt gggatattga cccgagcaaa    1020
attatcaaag tttggagcaa aaacgaagaa agcatgtatg aaagcggtac gattgttgat    1080
ctgccgaatg gtcgtcgtta tattgatctg gttgcaagct ataatgaaag caataccctg    1140
cagctgaaaa aagaggttgg ttggaaaccg atgttctatc atgttattca tccgaccccg    1200
agcgttccgg cactggttaa agcaaaagcc ggtgcaggta atctgcat                 1248
```

<210> SEQ ID NO 24
<211> LENGTH: 1248
<212> TYPE: DNA
<213> ORGANISM: Bacillus spec

<400> SEQUENCE: 24

```
aaagaactgg gtcatgatgt gctgaaaccg tatgatggtt gggcaagcta tggtgaaggt      60
acaaccggtg gtagcatggc aagtccgcag aatgtttata ccgttaccaa taaaaccgaa     120
ctggttcagg cactgggtgg taataatcat accaatcagt ataattccgt gccgaaaatc     180
atctatgtga aaggcaccat tgaactgaac gtggatgata ataatcagcc ggttggtccg     240
gaattctata agatccgca ttatgatttt gaagcctatc tgaaagagta tgatccgaaa     300
aaatggggca aaaagaagt tagcggtccg ctggaagaag cacgcgcacg tagccagaaa     360
aaacagaaag aacgtattgt tgtgaatgtg ggtagcaaca ccagcattat tggtgttggt     420
aaagatgcca aaattgtggg tggtggtttc ctgattaaaa acgtggataa tgtgatcatc     480
cgcaacatcg aatttgaagc accggtggat tattttccgg aatgggatcc gaccgatggc     540
accctgggtg aatggaatag cgaatatgat agcattacca ttgaaggcag ccatcatatt     600
tggatcgatc acaataccct taccgatggc gatcatccgg ataaaagcct gggcacctat     660
tttggtcgtc cgtttcagca gcatgatggc gcactggata tcaacaatag cagcgatttt     720
```

```
atcaccatca gctacaacgt gtttaaagac catgataaag tgaccctgat tggtgcaagc      780
gatagccgta tggcagatga aggtcatctg cgtgttaccc tgcatcacaa ttattacaaa      840
aatgttaccc agcgtctgcc tcgtgttcgt tttggtcagg ttcatatcta taacaactac      900
tatgagttta gcaacctggc cgattatgac tttcagtatg catggggtgt tggtgttgaa      960
agcaaaatct atgcccagaa caactatttc agcttcgatt gggatattga cccgagcaaa     1020
attatcaaag tttggagcaa aaacgaagaa agcatgtatg aaagcggtac gattgttgat     1080
ctgccgaatg gtcgtcgtta tattgatctg gttgcaagct ataatgaaag caataccctg     1140
cagctgaaaa aagaggttgg ttggaaaccg atgttctatc atgttattca tccgaccccg     1200
agcgttccgg cactggttaa agcaaaagcc ggtgcaggta atctgcat                  1248
```

<210> SEQ ID NO 25
<211> LENGTH: 1248
<212> TYPE: DNA
<213> ORGANISM: Bacillus spec

<400> SEQUENCE: 25

```
aaagaactgg gtcatgatgt gctgaaaccg tatgatggtt gggcaagcta tggtgaaggt       60
acaaccggtg gtagcatggc aagtccgcag aatgtttata ccgttaccaa taaaaccgaa      120
ctggttcagg cactgggtgg taataatcat accaatcagt ataattccgt gccgaaaatc      180
atctatgtga aaggcaccat tgaactgaac gtggatgata taatcagcc ggttggtccg       240 gaattctata aagatccgca ttatgatttt gaagcctatc tgaaagagta tgatccgaaa      300
aaatggggca aaaagaagt tagcggtccg ctggaagaag cacgcgcacg tagccagaaa       360
aaacagaaag aacgtattgt tgtgaatgtg ggtagcaaca ccagcattat tggtgttggt      420
aaagatgcca aaattgtggg tggtggtttc ctgattaaaa acgtggataa tgtgatcatc      480
cgcaacatcg aatttgaagc accggtggat tattttccgg aatgggatcc gaccgatggc      540
accctgggtg aatggaatag cgaatatgat agcattacca ttgaaggcag ccatcatatt      600
tggatcgatc acaataccttt taccgatggc gatcatccgg ataaaagcct gggcacctat      660
tttggtcgtc cgtttcagca gcatgatggc gcactggata tctgcaatag cagcgatttt      720
atcaccatca gctacaacgt gtttaaagac catgataaag tgaccctgat tggtgcaagc      780
gatagccgta tggcagatga aggtcatctg cgtgttaccc tgcatcacaa ttattacaaa      840
aatgttaccc agcgtctgcc tcgtgttcgt tttggtcagg ttcatatcta taacaactac      900
tatgagttta gcaacctggc cgattatgac tttcagtatg catggggtgt tggtgttgaa      960
agcaaaatct atgcccagaa caactatttc agcttcgatt gggatattga cccgagcaaa     1020
attatcaaag tttggagcaa aaacgaagaa agcatgtatg aaagcggtac gattgttgat     1080
ctgccgaatg gtcgtcgtta tattgatctg gttgcaagct ataatgaaag caataccctg     1140
cagctgaaaa aagaggttgg ttggaaaccg atgttctatc atgttattca tccgaccccg     1200
agcgttccgg cactggttaa agcaaaagcc ggtgcaggta atctgcat                  1248
```

<210> SEQ ID NO 26
<211> LENGTH: 1248
<212> TYPE: DNA
<213> ORGANISM: Bacillus spec

<400> SEQUENCE: 26

```
aaagaactgg gtcatgatgt gctgaaaccg aatgatggtt gggcaagcta tggtgaaggt       60
```

```
acaaccggtg gtagcgaagc aagtccggat aatgtttata ccgttaccaa taaaagcgaa    120
ctggttcagg cactgggtgg taataatcat accaatcagt ataattccac cccgaaaatc    180
atctatgtga aaggcaccat tgaactgaac gtggatgata ataatcagcc ggttggtccg    240
gaatattatg atgatccgca ttatgatttt gaagcctatc tgaaagagta tgatccgaaa    300
aaatggggca aaaagaagt tagcggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggttgat ttttttccgg aatgggatcc gaccgatggt    540
gaatatggcg aatggaatag cgaatatgat agcattacca tcgaaagcag ccatcatatt    600
tggatcgatc acaatacctt taccgatggc gatcatccgg ataaaagcct gggcacctat    660
tttggtcgtc cgtttcagca gcatgatggc gcactggata tcaaaaatag cagcgatttt    720
atcaccatca gctacaacgt gtttaaagac catgataaag tgagcctgat tggttcaagc    780
gatagccgta aaaccgatga aggtcatctg aaagttaccc tgcatcacaa ctattacaaa    840
aatgttaccc agcgtctgcc tcgtgttcgt tttggtcagg ttcatatcta taacaactac    900
tatgagttta gcaacctggc cgattatgac tttcagtatg catggggtgt tggtgttgaa    960
agcaaaatct atgcccagaa caactatttc agcttcgatt gggatattga cccgagcaaa   1020
attatcaaag tttggagcaa aaacgaagaa agcatgtatg aaagcggtac gattgttgat   1080
ctgccgaatg gtcgtcgtta tattgatctg gttgcaagct ataatgaaag caataccctg   1140
cagctgaaaa aagaggttgg ttggaaaccg atgttctatc atgttattca tccgaccccg   1200
agcgttccgg cactggttaa agcaaaagcc ggtgcaggta atctgcat             1248

<210> SEQ ID NO 27
<211> LENGTH: 1248
<212> TYPE: DNA
<213> ORGANISM: Bacillus spec

<400> SEQUENCE: 27
aaagaactgg gtcatgatgt gctgaaaccg aatgatggtt gggcaagcta tggtgaaggt     60
acaaccggtg gtagcgaagc aagtccggat aatgtttata ccgttaccaa taaaagcgaa    120
ctggttcagg cactgggtgg taataatcat accaatcagt ataattccac cccgaaaatc    180
atctatgtga aaggcaccat tgaactgaac gtggatgata ataatcagcc ggttggtccg    240
gaatattatg atgatccgca ttatgatttt gaagcctatc tgaaagagta tgatccgaaa    300
aaatggggca aaaagaagt tagcggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggttgat ttttttccgg aatgggatcc gaccgatggt    540
gaatatggcg aatggaatag cgaatatgat agcattacca tcgaaagcag ccatcatatt    600
tggatcgatc acaatacctt taccgatggc gatcatccgg ataaaagcct gggcacctat    660
tttggtcgtc cgtttcagca gcatgatggc gcactggata tcaccaatag cagcgatttt    720
atcaccatca gctacaacgt gtttaaagac catgataaag tgagcctgat tggttcaagc    780
gatagccgta aaaccgatga aggtcatctg aaagttaccc tgcatcacaa ctattacaaa    840
aatgttaccc agcgtctgcc tcgtgttcgt tttggtcagg ttcatatcta taacaactac    900
tatgagttta gcaacctggc cgattatgac tttcagtatg catggggtgt tggtgttgaa    960
```

```
agcaaaatct atgcccagaa caactatttc agcttcgatt gggatattga cccgagcaaa    1020
attatcaaag tttggagcaa aaacgaagaa agcatgtatg aaagcggtac gattgttgat    1080
ctgccgaatg tcgtcgtta tattgatctg gttgcaagct ataatgaaag caataccctg    1140
cagctgaaaa aagaggttgg ttggaaaccg atgttctatc atgttattca tccgaccccg    1200
agcgttccgg cactggttaa agcaaaagcc ggtgcaggta atctgcat                 1248
```

<210> SEQ ID NO 28
<211> LENGTH: 1248
<212> TYPE: DNA
<213> ORGANISM: Bacillus spec

<400> SEQUENCE: 28

```
aaagaactgg gtcatgatgt gctgaaaccg aatgatggtt gggcaagcta tggtgaaggt     60
acaaccggtg gtagcgaagc aagtccggat aatgtttata ccgttaccaa taaaagcgaa    120
ctggttcagg cactgggtgg taataatcat accaatcagt ataattccac cccgaaaatc    180
atctatgtga aaggcaccat tgaactgaac gtggatgata taatcagcc ggttggtccg     240 gaatattatg atgatccgca ttatgatttt gaagcctatc tgaaagagta tgatccgaaa    300
aaatggggca aaaagaagt tagcggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggttgat ttttttccgg aatgggatcc gaccgatggt    540
gaatatggcg aatggaatag cgaatatgat agcattacca tcgaaagcag ccatcatatt    600
tggatcgatc acaataccct taccgatggc gatcatccgg ataaaagcct gggcaccat    660 tttggtcgtc cgtttcagca gcatgatggc gcactggata tcagcaatag cagcgatttt    720
atcaccatca gctacaacgt gtttaaagac catgataaag tgagcctgat tggttcaagc    780
gatagccgta aaaccgatga aggtcatctg aaagttaccc tgcatcacaa ctattacaaa    840
aatgttaccc agcgtctgcc tcgtgttcgt tttggtcagg ttcatatcta taacaactac    900
tatgagttta gcaacctggc cgattatgac tttcagtatg catggggtgt tggtgttgaa    960
agcaaaatct atgcccagaa caactatttc agcttcgatt gggatattga cccgagcaaa    1020
attatcaaag tttggagcaa aaacgaagaa agcatgtatg aaagcggtac gattgttgat    1080
ctgccgaatg tcgtcgtta tattgatctg gttgcaagct ataatgaaag caataccctg    1140
cagctgaaaa aagaggttgg ttggaaaccg atgttctatc atgttattca tccgaccccg    1200
agcgttccgg cactggttaa agcaaaagcc ggtgcaggta atctgcat                 1248
```

<210> SEQ ID NO 29
<211> LENGTH: 1248
<212> TYPE: DNA
<213> ORGANISM: Bacillus spec

<400> SEQUENCE: 29

```
aaagaactgg gtcatgatgt gctgaaaccg aatgatggtt gggcaagcta tggtgaaggt     60
acaaccggtg gtagcgaagc aagtccggat aatgtttata ccgttaccaa taaaagcgaa    120
ctggttcagg cactgggtgg taataatcat accaatcagt ataattccac cccgaaaatc    180
atctatgtga aaggcaccat tgaactgaac gtggatgata taatcagcc ggttggtccg     240 gaatattatg atgatccgca ttatgatttt gaagcctatc tgaaagagta tgatccgaaa    300
```

| | |
|---|---|
| aaatggggca aaaaagaagt tagcggtccg ctggaagaag cacgcgcacg tagccagaaa | 360 |
| aaacagaaag aacgtattgt tgtgaatgtg ggtagcaaca ccagcattat tggtgttggt | 420 |
| aaagatgcca aaattgtggg tggtggtttc ctgattaaaa acgtggataa tgtgatcatc | 480 |
| cgcaacatcg aatttgaagc accggttgat ttttttccgg aatgggatcc gaccgatggt | 540 |
| gaatatggcg aatggaatag cgaatatgat agcattacca tcgaaagcag ccatcatatt | 600 |
| tggatcgatc acaataccttt taccgatggc gatcatccgg ataaaagcct gggcaccctat | 660 |
| tttggtcgtc cgtttcagca gcatgatggc gcactggata tcaacaatag cagcgatttt | 720 |
| atcaccatca gctacaacgt gtttaaagac catgataaag tgagcctgat tggttcaagc | 780 |
| gatagccgta aaaccgatga aggtcatctg aaagttaccc tgcatcacaa ctattacaaa | 840 |
| aatgttaccc agcgtctgcc tcgtgttcgt tttggtcagg ttcatatcta taacaactac | 900 |
| tatgagttta gcaacctggc cgattatgac tttcagtatg catggggtgt tggtgttgaa | 960 |
| agcaaaatct atgcccagaa caactatttc agcttcgatt gggatattga cccgagcaaa | 1020 |
| attatcaaag tttggagcaa aaacgaagaa agcatgtatg aaagcggtac gattgttgat | 1080 |
| ctgccgaatg gtcgtcgtta tattgatctg gttgcaagct ataatgaaag caatacccctg | 1140 |
| cagctgaaaa aagaggttgg ttggaaaccg atgttctatc atgttattca tccgaccccg | 1200 |
| agcgttccgg cactggttaa agcaaaagcc ggtgcaggta atctgcat | 1248 |

<210> SEQ ID NO 30
<211> LENGTH: 1248
<212> TYPE: DNA
<213> ORGANISM: Bacillus spec

<400> SEQUENCE: 30

| | |
|---|---|
| aaagaactgg gtcatgatgt gctgaaaccg aatgatggtt gggcaagcta tggtgaaggt | 60 |
| acaaccggtg gtagcgaagc aagtccggat aatgttttata ccgttaccaa taaaagcgaa | 120 |
| ctggttcagg cactgggtgg taataatcat accaatcagt ataattccac cccgaaaatc | 180 |
| atctatgtga aaggcaccat tgaactgaac gtggatgata taatcagcc ggttggtccg | 240 |
| gaatattatg atgatccgca ttatgatttt gaagcctatc tgaaagagta tgatccgaaa | 300 |
| aaatggggca aaaagaagt tagcggtccg ctggaagaag cacgcgcacg tagccagaaa | 360 |
| aaacagaaag aacgtattgt tgtgaatgtg ggtagcaaca ccagcattat tggtgttggt | 420 |
| aaagatgcca aaattgtggg tggtggtttc ctgattaaaa acgtggataa tgtgatcatc | 480 |
| cgcaacatcg aatttgaagc accggttgat ttttttccgg aatgggatcc gaccgatggt | 540 |
| gaatatggcg aatggaatag cgaatatgat agcattacca tcgaaagcag ccatcatatt | 600 |
| tggatcgatc acaataccttt taccgatggc gatcatccgg ataaaagcct gggcaccctat | 660 |
| tttggtcgtc cgtttcagca gcatgatggc gcactggata tctgcaatag cagcgatttt | 720 |
| atcaccatca gctacaacgt gtttaaagac catgataaag tgagcctgat tggttcaagc | 780 |
| gatagccgta aaaccgatga aggtcatctg aaagttaccc tgcatcacaa ctattacaaa | 840 |
| aatgttaccc agcgtctgcc tcgtgttcgt tttggtcagg ttcatatcta taacaactac | 900 |
| tatgagttta gcaacctggc cgattatgac tttcagtatg catggggtgt tggtgttgaa | 960 |
| agcaaaatct atgcccagaa caactatttc agcttcgatt gggatattga cccgagcaaa | 1020 |
| attatcaaag tttggagcaa aaacgaagaa agcatgtatg aaagcggtac gattgttgat | 1080 |
| ctgccgaatg gtcgtcgtta tattgatctg gttgcaagct ataatgaaag caatacccctg | 1140 |
| cagctgaaaa aagaggttgg ttggaaaccg atgttctatc atgttattca tccgaccccg | 1200 |

```
agcgttccgg cactggttaa agcaaaagcc ggtgcaggta atctgcat          1248
```

<210> SEQ ID NO 31
<211> LENGTH: 24
<212> TYPE: DNA
<213> ORGANISM: Bacillus spec

<400> SEQUENCE: 31

```
gaaattaata cgactcacta tagg                                     24
```

<210> SEQ ID NO 32
<211> LENGTH: 27
<212> TYPE: DNA
<213> ORGANISM: Bacillus spec

<400> SEQUENCE: 32

```
ggttatgcta gttattgctc agcggtg                                  27
```

<210> SEQ ID NO 33
<211> LENGTH: 39
<212> TYPE: DNA
<213> ORGANISM: Bacillus spec

<400> SEQUENCE: 33

```
gctgatggtg ataaaatcgc tgctattggt gatatccag                     39
```

<210> SEQ ID NO 34
<211> LENGTH: 39
<212> TYPE: DNA
<213> ORGANISM: Bacillus spec

<400> SEQUENCE: 34

```
gctgatggtg ataaaatcgc tgctattgct gatatccag                     39
```

<210> SEQ ID NO 35
<211> LENGTH: 39
<212> TYPE: DNA
<213> ORGANISM: Bacillus spec

<400> SEQUENCE: 35

```
gctgatggtg ataaaatcgc tgctattgtt gatatccag                     39
```

<210> SEQ ID NO 36
<211> LENGTH: 39
<212> TYPE: DNA
<213> ORGANISM: Bacillus spec

<400> SEQUENCE: 36

```
gctgatggtg ataaaatcgc tgctattgca gatatccag                     39
```

<210> SEQ ID NO 37
<211> LENGTH: 40
<212> TYPE: DNA
<213> ORGANISM: Bacillus spec

<400> SEQUENCE: 37

```
aatagcagcg attttatcac catcagctac aacgtgttta                    40
```

<210> SEQ ID NO 38
<211> LENGTH: 37
<212> TYPE: DNA
<213> ORGANISM: Bacillus spec

<400> SEQUENCE: 38
gccatcatgc tgctgaaacg gacgaccaaa ataggtg                37

<210> SEQ ID NO 39
<211> LENGTH: 40
<212> TYPE: DNA
<213> ORGANISM: Bacillus spec

<400> SEQUENCE: 39
ggtcgtccgt ttcagcagca tgatggcctg ctggatatca            40

<210> SEQ ID NO 40
<211> LENGTH: 416
<212> TYPE: PRT
<213> ORGANISM: Bacillus spec

<400> SEQUENCE: 40

```
Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Leu Leu Asp Ile Thr Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
    290                 295                 300
```

```
Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
            325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
        370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
            405                 410                 415
```

<210> SEQ ID NO 41
<211> LENGTH: 416
<212> TYPE: PRT
<213> ORGANISM: Bacillus spec

<400> SEQUENCE: 41

```
Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
            35                  40                  45

Asn His Thr Asn Gln Tyr Asn Ser Val Pro Lys Ile Tyr Val Lys
50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
            85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
            115                 120                 125

Tyr Val Gly Ser Asn Thr Ser Ile Ile Gly Val Gly Lys Asp Ala Lys
        130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
            165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
            195                 200                 205

Asp Gly Asp His Pro Asp Arg Ser Leu Gly Thr Tyr Phe Gly Arg Pro
        210                 215                 220

Phe Gln Gln His Asp Gly Leu Leu Asp Ile Ser Asn Ser Ser Asp Phe
225                 230                 235                 240

Ile Thr Ile Ser Tyr Asn Val Phe Thr Asn His Asp Lys Val Thr Leu
            245                 250                 255

Ile Gly Ala Ser Asp Ser Arg Met Ala Asp Ser Gly His Leu Arg Val
            260                 265                 270
```

```
Thr Leu His His Asn Tyr Tyr Lys Asn Val Thr Gln Arg Leu Pro Arg
            275                 280                 285

Val Arg Phe Gly Gln Val His Ile Tyr Asn Asn Tyr Tyr Glu Phe Ser
    290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
            325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
            355                 360                 365

Asp Leu Val Ala Ser Tyr Asn Glu Ser Asn Thr Leu Gln Leu Lys Lys
370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
            405                 410                 415

<210> SEQ ID NO 42
<211> LENGTH: 416
<212> TYPE: PRT
<213> ORGANISM: Bacillus spec

<400> SEQUENCE: 42

Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
            20                  25                  30

Tyr Thr Val Thr Asn Lys Thr Glu Leu Val Gln Ala Leu Gly Gly Asn
            35                  40                  45

Asn His Thr Asn Gln Tyr Asn Ser Val Pro Lys Ile Ile Tyr Val Lys
    50                  55                  60

Gly Thr Ile Glu Leu Asn Val Asp Asp Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
            115                 120                 125

Asn Val Gly Ser Asn Thr Ser Ile Ile Gly Val Gly Lys Asp Ala Lys
    130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Thr Ile Glu Gly Ser His His Ile Trp Ile Asp His Asn Thr Phe Thr
            195                 200                 205

Asp Gly Asp His Pro Asp Lys Ser Leu Gly Thr Tyr Phe Gly Arg Pro
    210                 215                 220

Phe Gln Gln His Asp Gly Leu Leu Asp Ile Asn Asn Ser Ser Asp Phe
```

```
                225                 230                 235                 240
        Ile Thr Ile Ser Tyr Asn Val Phe Lys Asp His Asp Lys Val Thr Leu
                        245                 250                 255

Ile Gly Ala Ser Asp Ser Arg Met Ala Asp Glu Gly His Leu Arg Val
                        260                 265                 270

Thr Leu His His Asn Tyr Tyr Lys Asn Val Thr Gln Arg Leu Pro Arg
                        275                 280                 285

Val Arg Phe Gly Gln Val His Ile Tyr Asn Asn Tyr Glu Phe Ser
            290                 295                 300

Asn Leu Ala Asp Tyr Asp Phe Gln Tyr Ala Trp Gly Val Gly Val Glu
        305                 310                 315                 320

Ser Lys Ile Tyr Ala Gln Asn Asn Tyr Phe Ser Phe Asp Trp Asp Ile
                        325                 330                 335

Asp Pro Ser Lys Ile Ile Lys Val Trp Ser Lys Asn Glu Glu Ser Met
                        340                 345                 350

Tyr Glu Ser Gly Thr Ile Val Asp Leu Pro Asn Gly Arg Arg Tyr Ile
                        355                 360                 365

Asp Leu Val Ala Ser Tyr Asn Glu Ser Asn Thr Leu Gln Leu Lys Lys
                370                 375                 380

Glu Val Gly Trp Lys Pro Met Phe Tyr His Val Ile His Pro Thr Pro
        385                 390                 395                 400

Ser Val Pro Ala Leu Val Lys Ala Lys Ala Gly Ala Gly Asn Leu His
                        405                 410                 415

<210> SEQ ID NO 43
        <211> LENGTH: 416
        <212> TYPE: PRT
        <213> ORGANISM: Bacillus spec

<400> SEQUENCE: 43

Lys Glu Leu Gly His Asp Val Leu Lys Pro Asn Asp Gly Trp Ala Ser
        1               5                   10                  15

Tyr Gly Glu Gly Thr Thr Gly Gly Ser Glu Ala Ser Pro Asp Asn Val
                        20                  25                  30

Tyr Thr Val Thr Asn Lys Ser Glu Leu Val Gln Ala Leu Gly Gly Asn
                        35                  40                  45

Asn His Thr Asn Gln Tyr Asn Ser Thr Pro Lys Ile Ile Tyr Val Lys
                50                  55                  60

Gly Thr Ile Glu Leu Asn Val Asp Asp Asn Gln Pro Val Gly Pro
        65                  70                  75                  80

Glu Tyr Tyr Asp Asp Pro His Tyr Asp Phe Glu Ala Tyr Leu Lys Glu
                        85                  90                  95

Tyr Asp Pro Lys Lys Trp Gly Lys Lys Glu Val Ser Gly Pro Leu Glu
                        100                 105                 110

Glu Ala Arg Ala Arg Ser Gln Lys Lys Gln Lys Glu Arg Ile Val Val
                        115                 120                 125

Asn Val Gly Ser Asn Thr Ser Ile Ile Gly Val Gly Lys Asp Ala Lys
                130                 135                 140

Ile Val Gly Gly Gly Phe Leu Ile Lys Asn Val Asp Asn Val Ile Ile
        145                 150                 155                 160

Arg Asn Ile Glu Phe Glu Ala Pro Val Asp Phe Phe Pro Glu Trp Asp
                        165                 170                 175

Pro Thr Asp Gly Glu Tyr Gly Glu Trp Asn Ser Glu Tyr Asp Ser Ile
                        180                 185                 190
```

```
Thr Ile Glu Ser Ser His His Ile Trp Ile Asp His Asn Thr Phe Thr
            195                 200                 205

Asp Gly Asp His Pro Asp Lys Ser Leu Gly Thr Tyr Phe Gly Arg Pro
        210                 215                 220

Phe Gln Gln His Asp Gly Leu Leu Asp Ile Cys Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
    290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 44
<211> LENGTH: 1248
<212> TYPE: DNA
<213> ORGANISM: Bacillus spec

<400> SEQUENCE: 44
aaagaactgg gtcatgaagt tctgaaaccg tatgatggtt gggcagcgta tggtgaaggt      60
acaaccggtg gtgcaatggc aagtccgcag aatgtttttg ttgttaccaa tcgtaccgaa     120
ctgattcagg cactgggtgg taataatcat accaatcagt ataattccgt gccgaaaatc     180
atctatgtga aaggcaccat tgatctgaac gtggatgata taatcagcc ggttggtccg      240 gatttctata agatccgca ttttgatttt gaggcctatc tgcgtgaata tgatccggca      300
acctggggta aaaagaagt tgaaggtccg ctggaagaag cacgcgttcg tagccagaaa      360
aaacagaaag atcgtatcat ggtttatgtg ggtagcaaca ccagcattat tggtgttggt     420
aaagacgcga aaatcaaagg tggtggtttc ctgattaaaa acgtggataa tgtgatcatc     480
cgcaacatcg aatttgaagc accgctggat tattttccgg aatgggatcc gaccgatggc     540
accctgggtg aatggaatag cgaatatgat agcattagca ttgaaggcag cagccatatt     600
tggattgatc acaataccct taccgatggc gatcatccgg atcgtagcct gggcaccctat    660 tttggtcgtc cgtttcagca gcatgatggc ctgctggata tcaccaatag cagcgatttt     720
atcaccatca gctacaacgt gtttaaggcc cacgataaag ttaccctgat tggtgcaagc     780
gatagccgta tggcagatag cggtcatctg cgtgttaccc tgcatcacaa ttattacaaa     840
aatgttaccc agcgtctgcc tcgtgttcgt tttggtcagg ttcatatcta taacaactac     900
```

```
tatgagttta gcaacctggc cgattatgat tttcagtatg catggggtgt tggtgtgttt      960
agccagattt atgcacagaa caactatttc agcttcgatt gggatattga tccgagcctg     1020
attatcaaag tttggagcaa aaatgaagaa agcatgtatg aaaccggcac catcgttgat     1080
ctgccgaatg gtcgtcgtta tattgatctg gttgcaagct ataatgaaag cataccctg     1140 cagctgaaaa aagaggttac ctggaaaccg atgttctatc atgttattca tccgaccccg     1200
agcgttccgg cactggttaa agcaaaagcc ggtgcaggta atctgcat                  1248

<210> SEQ ID NO 45
<211> LENGTH: 1248
<212> TYPE: DNA
<213> ORGANISM: Bacillus spec

<400> SEQUENCE: 45
aaagaactgg gtcatgaagt tctgaaaccg tatgatggtt gggcagcgta tggtgaaggt       60
acaaccggtg gtgcaatggc aagtccgcag aatgttttg ttgttaccaa tcgtaccgaa      120
ctgattcagg cactgggtgg taataatcat accaatcagt ataattccgt gccgaaaatc     180
atctatgtga aaggcaccat tgatctgaac gtggatgata taatcagcc ggttggtccg      240 gatttctata agatccgca ttttgatttt gaggcctatc tgcgtgaata tgatccggca      300
acctggggta aaaagaagt tgaaggtccg ctggaagaag cacgcgttcg tagccagaaa      360
aaacagaaag atcgtatcat ggtttatgtg ggtagcaaca ccagcattat tggtgttggt     420
aaagacgcga aaatcaaagg tggtggtttc ctgattaaaa acgtggataa tgtgatcatc     480
cgcaacatcg aatttgaagc accgctggat tattttccgg aatgggatcc gaccgatggc     540
accctgggtg aatggaatag cgaatatgat agcattagca ttgaaggcag cagccatatt     600
tggattgatc acaataccctt taccgatggc gatcatccgg atcgtagcct gggcacctat     660
tttggtcgtc cgtttcagca gcatgatggc ctgctggata tcagcaatag cagcgatttt     720
atcaccatca gctacaacgt gtttaccaac cacgataaag ttaccctgat tggtgcaagc     780
gatagccgta tggcagatag cggtcatctg cgtgttaccc tgcatcacaa ttattacaaa     840
aatgttaccc agcgtctgcc tcgtgttcgt tttggtcagg ttcatatcta taacaactac     900
tatgagttta gcaacctggc cgattatgat tttcagtatg catggggtgt tggtgtgttt     960
agccagattt atgcacagaa caactatttc agcttcgatt gggatattga tccgagcctg    1020
attatcaaag tttggagcaa aaatgaagaa agcatgtatg aaaccggcac catcgttgat    1080
ctgccgaatg gtcgtcgtta tattgatctg gttgcaagct ataatgaaag cataccctg     1140 cagctgaaaa aagaggttac ctggaaaccg atgttctatc atgttattca tccgaccccg    1200
agcgttccgg cactggttaa agcaaaagcc ggtgcaggta atctgcat                 1248

<210> SEQ ID NO 46
<211> LENGTH: 1248
<212> TYPE: DNA
<213> ORGANISM: Bacillus spec

<400> SEQUENCE: 46
aaagaactgg gtcatgatgt gctgaaaccg tatgatggtt gggcaagcta tggtgaaggt       60
acaaccggtg gtagcatggc aagtccgcag aatgtttata ccgttaccaa taaaaccgaa      120
ctggttcagg cactgggtgg taataatcat accaatcagt ataattccgt gccgaaaatc     180
atctatgtga aaggcaccat tgaactgaac gtggatgata taatcagcc ggttggtccg      240
```

```
gaattctata aagatccgca ttatgatttt gaagcctatc tgaaagagta tgatccgaaa    300
aaatggggca aaaagaagt tagcggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggtggat tattttccgg aatgggatcc gaccgatggc    540
accctgggtg aatggaatag cgaatatgat agcattacca ttgaaggcag ccatcatatt    600
tggatcgatc acaataccct taccgatggc gatcatccgg ataaaagcct gggcacctat    660
tttggtcgtc cgtttcagca gcatgatggc ctgctggata tcaacaatag cagcgatttt    720
atcaccatca gctacaacgt gtttaaagac catgataaag tgaccctgat tggtgcaagc    780
gatagccgta tggcagatga aggtcatctg cgtgttaccc tgcatcacaa ttattacaaa    840
aatgttaccc agcgtctgcc tcgtgttcgt tttggtcagg ttcatatcta taacaactac    900
tatgagttta gcaacctggc cgattatgac tttcagtatg catggggtgt tggtgttgaa    960
agcaaaatct atgcccagaa caactatttc agcttcgatt gggatattga cccgagcaaa    1020
attatcaaag tttggagcaa aaacgaagaa agcatgtatg aaagcggtac gattgttgat    1080
ctgccgaatg gtcgtcgtta tattgatctg gttgcaagct ataatgaaag caataccctg    1140
cagctgaaaa aagaggttgg ttggaaaccg atgttctatc atgttattca tccgaccccg    1200
agcgttccgg cactggttaa agcaaaagcc ggtgcaggta atctgcat             1248
```

<210> SEQ ID NO 47
<211> LENGTH: 1248
<212> TYPE: DNA
<213> ORGANISM: Bacillus spec

<400> SEQUENCE: 47

```
aaagaactgg gtcatgatgt gctgaaaccg aatgatggtt gggcaagcta tggtgaaggt    60
acaaccggtg gtagcgaagc aagtccggat aatgtttata ccgttaccaa taaaagcgaa    120
ctggttcagg cactgggtgg taataatcat accaatcagt ataattccac cccgaaaatc    180
atctatgtga aaggcaccat tgaactgaac gtggatgata taatcagcc ggttggtccg    240 gaatattatg atgatccgca ttatgatttt gaagcctatc tgaaagagta tgatccgaaa    300
aaatggggca aaaagaagt tagcggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggttgat ttttttccgg aatgggatcc gaccgatggt    540
gaatatggcg aatggaatag cgaatatgat agcattacca tcgaaagcag ccatcatatt    600
tggatcgatc acaataccct taccgatggc gatcatccgg ataaaagcct gggcacctat    660
tttggtcgtc cgtttcagca gcatgatggc ctgctggata tctgcaatag cagcgatttt    720
atcaccatca gctacaacgt gtttaaagac catgataaag tgagcctgat tggttcaagc    780
gatagccgta aaccgatga aggtcatctg aaagttaccc tgcatcacaa ctattacaaa    840
aatgttaccc agcgtctgcc tcgtgttcgt tttggtcagg ttcatatcta taacaactac    900
tatgagttta gcaacctggc cgattatgac tttcagtatg catggggtgt tggtgttgaa    960
agcaaaatct atgcccagaa caactatttc agcttcgatt gggatattga cccgagcaaa    1020
attatcaaag tttggagcaa aaacgaagaa agcatgtatg aaagcggtac gattgttgat    1080
ctgccgaatg gtcgtcgtta tattgatctg gttgcaagct ataatgaaag caataccctg    1140
```

```
cagctgaaaa aagaggttgg ttggaaaccg atgttctatc atgttattca tccgaccccg    1200
agcgttccgg cactggttaa agcaaaagcc ggtgcaggta atctgcat                1248
```

<210> SEQ ID NO 48
<211> LENGTH: 416
<212> TYPE: PRT
<213> ORGANISM: Bacillus spec

<400> SEQUENCE: 48

```
Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Leu Leu Asp Ile Lys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Glu Phe Ser
    290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
            340                 345                 350
```

```
Tyr Glu Thr Gly Thr Ile Val Asp Leu Pro Asn Gly Arg Tyr Ile
            355                 360                 365

Asp Leu Val Ala Ser Tyr Asn Glu Ser Asn Thr Leu Gln Leu Lys Lys
370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 49
<211> LENGTH: 416
<212> TYPE: PRT
<213> ORGANISM: Bacillus spec

<400> SEQUENCE: 49

Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
                20                  25                  30

Tyr Thr Val Thr Asn Lys Thr Glu Leu Val Gln Ala Leu Gly Gly Asn
            35                  40                  45

Asn His Thr Asn Gln Tyr Asn Ser Val Pro Lys Ile Ile Tyr Val Lys
    50                  55                  60

Gly Thr Ile Glu Leu Asn Val Asp Asp Asn Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
        115                 120                 125

Asn Val Gly Ser Asn Thr Ser Ile Ile Gly Val Gly Lys Asp Ala Lys
    130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Gly Trp Asn Ser Glu Tyr Asp Ser Ile
            180                 185                 190

Thr Ile Glu Gly Ser His His Ile Trp Ile Asp His Asn Thr Phe Thr
        195                 200                 205

Asp Gly Asp His Pro Asp Lys Ser Leu Gly Thr Tyr Phe Gly Arg Pro
    210                 215                 220

Phe Gln Gln His Asp Gly Leu Leu Asp Ile Lys Asn Ser Ser Asp Phe
225                 230                 235                 240

Ile Thr Ile Ser Tyr Asn Val Phe Lys Asp His Asp Lys Val Thr Leu
                245                 250                 255

Ile Gly Ala Ser Asp Ser Arg Met Ala Asp Glu Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
    290                 295                 300

Asn Leu Ala Asp Tyr Asp Phe Gln Tyr Ala Trp Gly Val Gly Val Glu
305                 310                 315                 320
```

```
Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
            405                 410                 415

<210> SEQ ID NO 50
<211> LENGTH: 416
<212> TYPE: PRT
<213> ORGANISM: Bacillus spec

<400> SEQUENCE: 50

Lys Glu Leu Gly His Asp Val Leu Lys Pro Asn Asp Gly Trp Ala Ser
1               5                   10                  15

Tyr Gly Glu Gly Thr Thr Gly Gly Ser Glu Ala Ser Pro Asp Asn Val
            20                  25                  30

Tyr Thr Val Thr Asn Lys Ser Glu Leu Val Gln Ala Leu Gly Gly Asn
        35                  40                  45

Asn His Thr Asn Gln Tyr Asn Ser Thr Pro Lys Ile Ile Tyr Val Lys
    50                  55                  60

Gly Thr Ile Glu Leu Asn Val Asp Asp Asn Asn Gln Pro Val Gly Pro
65                  70                  75                  80

Glu Tyr Tyr Asp Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
        115                 120                 125

Asn Val Gly Ser Asn Thr Ser Ile Ile Gly Val Gly Lys Asp Ala Lys
    130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Phe Phe Pro Glu Trp Asp
                165                 170                 175

Pro Thr Asp Gly Glu Tyr Gly Glu Trp Asn Ser Glu Tyr Asp Ser Ile
            180                 185                 190

Thr Ile Glu Ser Ser His His Ile Trp Ile Asp His Asn Thr Phe Thr
        195                 200                 205

Asp Gly Asp His Pro Asp Lys Ser Leu Gly Thr Tyr Phe Gly Arg Pro
    210                 215                 220

Phe Gln Gln His Asp Gly Leu Leu Asp Ile Lys Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
            260                 265                 270

Thr Leu His His Asn Tyr Tyr Lys Asn Val Thr Gln Arg Leu Pro Arg
```

|     |     |     |     | 275 |     |     |     | 280 |     |     |     | 285 |     |     |
| --- | --- | --- | --- | --- | --- | --- | --- | --- | --- | --- | --- | --- | --- | --- |
| Val | Arg | Phe | Gly | Gln | Val | His | Ile | Tyr | Asn | Asn | Tyr | Tyr | Glu | Phe | Ser |
|     |     |     |     | 290 |     |     |     | 295 |     |     |     | 300 |     |     |     |

Asn Leu Ala Asp Tyr Asp Phe Gln Tyr Ala Trp Gly Val Gly Val Glu
305               310               315               320

Ser Lys Ile Tyr Ala Gln Asn Asn Tyr Phe Ser Phe Asp Trp Asp Ile
              325               330               335

Asp Pro Ser Lys Ile Ile Lys Val Trp Ser Lys Asn Glu Glu Ser Met
              340               345               350

Tyr Glu Ser Gly Thr Ile Val Asp Leu Pro Asn Gly Arg Arg Tyr Ile
              355               360               365

Asp Leu Val Ala Ser Tyr Asn Glu Ser Asn Thr Leu Gln Leu Lys Lys
              370               375               380

Glu Val Gly Trp Lys Pro Met Phe Tyr His Val Ile His Pro Thr Pro
385               390               395               400

Ser Val Pro Ala Leu Val Lys Ala Lys Ala Gly Ala Gly Asn Leu His
              405               410               415

<210> SEQ ID NO 51
<211> LENGTH: 1248
<212> TYPE: DNA
<213> ORGANISM: Bacillus spec

<400> SEQUENCE: 51

```
aaagaactgg gtcatgaagt tctgaaaccg tatgatggtt gggcagcgta tggtgaaggt      60
acaaccggtg gtgcaatggc aagtccgcag aatgtttttg ttgttaccaa tcgtaccgaa     120
ctgattcagg cactgggtgg taataatcat accaatcagt ataattccgt gccgaaaatc     180
atctatgtga aaggcaccat tgatctgaac gtggatgata taatcagcc ggttggtccg      240
gatttctata agatccgca ttttgatttt gaggcctatc tgcgtgaata tgatccggca      300
acctggggta aaaagaagt tgaaggtccg ctggaagaag cacgcgttcg tagccagaaa      360
aaacagaaag atcgtatcat ggtttatgtg ggtagcaaca ccagcattat tggtgttggt     420
aaagacgcga aaatcaaagg tggtggtttc ctgattaaaa acgtggataa tgtgatcatc     480
cgcaacatcg aatttgaagc accgctggat tattttccgg aatgggatcc gaccgatggc     540
accctgggtg aatggaatag cgaatatgat agcattagca ttgaaggcag cagccatatt     600
tggattgatc acaataccct taccgatggc gatcatccgg atcgtagcct gggcacctat     660
tttggtcgtc cgtttcagca gcatgatggc ctgctggata tcaaaaatag cagcgatttt     720
atcaccatca gctacaacgt gtttaccaac cacgataaag ttaccctgat tggtgcaagc     780
gatagccgta tggcagatag cggtcatctg cgtgttaccc tgcatcacaa ttattacaaa     840
aatgttaccc agcgtctgcc tcgtgttcgt tttggtcagg ttcatatcta taacaactac     900
tatgagttta gcaacctggc cgattatgat tttcagtatg catggggtgt tggtgtgttt     960
agccagattt atgcacagaa caactatttc agcttcgatt gggatattga tccgagcctg    1020
attatcaaag tttggagcaa aaatgaagaa agcatgtatg aaaccggcac catcgttgat    1080
ctgccgaatg gtcgtcgtta tattgatctg gttgcaagct ataatgaaag caataccctg    1140
cagctgaaaa aagaggttac ctggaaaccg atgttctatc atgttattca tccgaccccg    1200
agcgttccgg cactggttaa agcaaaagcc ggtgcaggta atctgcat                 1248
```

<210> SEQ ID NO 52
<211> LENGTH: 1248

<212> TYPE: DNA
<213> ORGANISM: Bacillus spec

<400> SEQUENCE: 52

```
aaagaactgg gtcatgatgt gctgaaaccg tatgatggtt gggcaagcta tggtgaaggt    60
acaaccggtg gtagcatggc aagtccgcag aatgtttata ccgttaccaa taaaaccgaa   120
ctggttcagg cactgggtgg taataatcat accaatcagt ataattccgt gccgaaaatc   180
atctatgtga aaggcaccat tgaactgaac gtggatgata taatcagcc ggttggtccg    240
gaattctata agatccgca ttatgatttt gaagcctatc tgaaagagta tgatccgaaa    300
aaatggggca aaaagaagt tagccggtccg ctggaagaag cacgcgcacg tagccagaaa   360
aaacagaaag aacgtattgt tgtgaatgtg ggtagcaaca ccagcattat tggtgttggt   420
aaagatgcca aaattgtggg tggtggttc ctgattaaaa acgtggataa tgtgatcatc     480
cgcaacatcg aatttgaagc accggtggat tattttccgg aatgggatcc gaccgatggc   540
accctgggtg aatggaatag cgaatatgat agcattacca ttgaaggcag ccatcatatt   600
tggatcgatc acaatacctt taccgatggc gatcatccgg ataaaagcct gggcacctat   660
tttggtcgtc cgtttcagca gcatgatggc ctgctggata tcaaaaatag cagcgatttt   720
atcaccatca gctacaacgt gtttaaagac catgataaag tgaccctgat tggtgcaagc   780
gatagccgta tggcagatga aggtcatctg cgtgttaccc tgcatcacaa ttattacaaa   840
aatgttaccc agcgtctgcc tcgtgttcgt tttggtcagg ttcatatcta taacaactac   900
tatgagttta gcaacctggc cgattatgac tttcagtatg catggggtgt tggtgttgaa   960
agcaaaatct atgcccagaa caactatttc agcttcgatt gggatattga cccgagcaaa  1020
attatcaaag tttggagcaa aaacgaagaa agcatgtatg aaagcggtac gattgttgat  1080
ctgccgaatg gtcgtcgtta tattgatctg gttgcaagct ataatgaaag caataccctg  1140
cagctgaaaa aagaggttgg ttggaaaccg atgttctatc atgttattca tccgaccccg  1200
agcgttccgg cactggttaa agcaaaagcc ggtgcaggta atctgcat                1248
```

<210> SEQ ID NO 53
<211> LENGTH: 1248
<212> TYPE: DNA
<213> ORGANISM: Bacillus spec

<400> SEQUENCE: 53

```
aaagaactgg gtcatgatgt gctgaaaccg aatgatggtt gggcaagcta tggtgaaggt    60
acaaccggtg gtagcgaagc aagtccggat aatgtttata ccgttaccaa taaaagcgaa   120
ctggttcagg cactgggtgg taataatcat accaatcagt ataattccac cccgaaaatc   180
atctatgtga aaggcaccat tgaactgaac gtggatgata taatcagcc ggttggtccg    240
gaatattatg atgatccgca ttatgatttt gaagcctatc tgaaagagta tgatccgaaa    300
aaatggggca aaaagaagt tagccggtccg ctggaagaag cacgcgcacg tagccagaaa   360
aaacagaaag aacgtattgt tgtgaatgtg ggtagcaaca ccagcattat tggtgttggt   420
aaagatgcca aaattgtggg tggtggttc ctgattaaaa acgtggataa tgtgatcatc     480
cgcaacatcg aatttgaagc accggttgat tttttccgg aatgggatcc gaccgatggt   540
gaatatggcg aatggaatag cgaatatgat agcattacca tcgaaagcag ccatcatatt   600
tggatcgatc acaatacctt taccgatggc gatcatccgg ataaaagcct gggcacctat   660
tttggtcgtc cgtttcagca gcatgatggc ctgctggata tcaaaaatag cagcgatttt   720
```

-continued

| | | | | | |
|---|---|---|---|---|---|
| atcaccatca | gctacaacgt | gtttaaagac | catgataaag | tgagcctgat | tggttcaagc | 780 |
| gatagccgta | aaaccgatga | aggtcatctg | aaagttaccc | tgcatcacaa | ctattacaaa | 840 |
| aatgttaccc | agcgtctgcc | tcgtgttcgt | tttggtcagg | ttcatatcta | taacaactac | 900 |
| tatgagttta | gcaacctggc | cgattatgac | tttcagtatg | catggggtgt | tggtgttgaa | 960 |
| agcaaaatct | atgcccagaa | caactatttc | agcttcgatt | gggatattga | cccgagcaaa | 1020 |
| attatcaaag | tttggagcaa | aaacgaagaa | agcatgtatg | aaagcggtac | gattgttgat | 1080 |
| ctgccgaatg | gtcgtcgtta | tattgatctg | gttgcaagct | ataatgaaag | caatacccctg | 1140 |
| cagctgaaaa | aagaggttgg | ttggaaaccg | atgttctatc | atgttattca | tccgaccccg | 1200 |
| agcgttccgg | cactggttaa | agcaaaagcc | ggtgcaggta | atctgcat | | 1248 |

The invention claimed is:

1. A polypeptide with pectate lyase activity, the polypeptide comprising:
an amino acid sequence that is at least 70% identical to the amino acid according to SEQ ID NO: 1, and a small, polar, non-charged amino acid residue at an amino acid position corresponding to position 235 in SEQ ID NO: 1, and wherein the polypeptide has an improved thermostability compared to an identical polypeptide not having said substitution.

2. The polypeptide of claim 1, wherein the small, polar, non-charged amino acid residue is selected from the group consisting of amino acids Threonine, Serine, Asparagine and Cysteine.

3. The polypeptide of claim 1, wherein the small, polar, non-charged amino acid residue is Threonine.

4. The polypeptide of claim 1, wherein the polypeptide comprises an amino acid sequence that is at least 75% identical to the amino acid according to SEQ ID NO: 1.

5. The polypeptide of claim 1, wherein the polypeptide comprises a leucine residue at an amino acid position corresponding to position 231 in SEQ ID NO: 1.

6. A composition comprising the polypeptide of claim 1.

7. A nucleic acid encoding the polypeptide of claim 1.

8. A vector comprising the nucleic acid of claim 7.

9. A composition comprising the nucleic acid of claim 7.

10. A recombinant host cell comprising the nucleic acid of claim 7.

11. The recombinant host cell of claim 10, wherein the host cell is selected from the group consisting of *Escherichia coli, Bacillus, Corynebacterium, Pseudomonas, Pichia pastoris, Saccharomyces cerevisiae, Yarrowia lipolytica*, filamentous fungi, yeast and insect cells.

12. A method for producing the polypeptide of claim 1, the method comprising:

culturing the recombinant host cell of claim 10 under conditions suitable for the production of the polypeptide, and
recovering the polypeptide obtained, and
optionally purifying said polypeptide.

13. A method for improving the thermostability of a polypeptide with pectate lyase activity comprising an amino acid sequence that is at least 70% identical to the amino acid according to SEQ ID NO: 1, the method comprising:
altering the amino acid at a position corresponding to position 235 in SEQ ID NO: 1 to a small, polar, non-charged amino acid residue, and
optionally altering the amino acid at a position corresponding to position 231 in SEQ ID NO: 1 to a leucine residue.

14. The polypeptide of claim 1, wherein the polypeptide comprises an amino acid sequence that is at least 80% identical to the amino acid according to SEQ ID NO: 1.

15. The polypeptide of claim 1, wherein the polypeptide comprises an amino acid sequence that is at least 85% identical to the amino acid according to SEQ ID NO: 1.

16. The polypeptide of claim 1, wherein the polypeptide comprises an amino acid sequence that is at least 90% identical to the amino acid according to SEQ ID NO: 1.

17. The polypeptide of claim 1, wherein the polypeptide comprises an amino acid sequence that is at least 95% identical to the amino acid according to SEQ ID NO: 1.

18. The polypeptide of claim 1, wherein the polypeptide comprises an amino acid sequence that is identical to the amino acid according to SEQ ID NO: 1.

19. A composition comprising the vector of claim 8.

20. A recombinant host cell comprising the vector of claim 8.

* * * * *